(12) United States Patent
Samuelson et al.

(10) Patent No.: US 9,446,072 B2
(45) Date of Patent: *Sep. 20, 2016

(54) METHODS OF AMELIORATING OXIDATIVE STRESS BY INCREASING THE EFFICIENCY OF GPX AND SOD ACTIVITY

(71) Applicant: Reoxcyn Discoveries Group, INC., Salt Lake City, UT (US)

(72) Inventors: Gary Samuelson, Sandy, UT (US); Verdis Norton, Sandy, UT (US)

(73) Assignee: Reoxcyn Discoveries Group, Inc., Salt Lake City, UT (US)

( * ) Notice: Subject to any disclaimer, the term of this patent is extended or adjusted under 35 U.S.C. 154(b) by 108 days.

This patent is subject to a terminal disclaimer.

(21) Appl. No.: 13/857,225

(22) Filed: Apr. 5, 2013

(65) Prior Publication Data
US 2013/0236563 A1    Sep. 12, 2013

Related U.S. Application Data

(63) Continuation-in-part of application No. 12/592,402, filed on Nov. 24, 2009, now Pat. No. 8,455,010, which is a continuation-in-part of application No. 12/383,212, filed on Mar. 20, 2009, now Pat. No. 8,367,120, which is a continuation-in-part of application No. 12/290,398, filed on Oct. 30, 2008, now abandoned.

(60) Provisional application No. 61/001,010, filed on Oct. 30, 2007.

(51) Int. Cl.
*A61K 33/00* (2006.01)
*A61K 33/14* (2006.01)
*A61K 33/40* (2006.01)
*A61K 45/06* (2006.01)
*A61K 33/20* (2006.01)

(52) U.S. Cl.
CPC ............... *A61K 33/40* (2013.01); *A61K 33/00* (2013.01); *A61K 33/14* (2013.01); *A61K 33/20* (2013.01); *A61K 45/06* (2013.01)

(58) Field of Classification Search
None
See application file for complete search history.

(56) References Cited

U.S. PATENT DOCUMENTS

2006/0076248 A1*  4/2006  Kindred ................... 205/743

OTHER PUBLICATIONS

Hanaoka (Journal of Applied Electrochemistry 2001, 31, 1307-1313).*

* cited by examiner

*Primary Examiner* — Abigail Fisher
*Assistant Examiner* — Jessica Kassa
(74) *Attorney, Agent, or Firm* — David R. Conklin; Kirton McConkie

(57) ABSTRACT

Methods of ameliorating cellular oxidative stress are disclosed. The methods include contacting at least one cell with a composition comprising a mixture of reduced species (RS) and reactive oxygen species (ROS). The mixture of reduced species (RS) and reactive oxygen species (ROS) mirrors a target mixture where the target mixture is the reduced species (RS) and reactive oxygen species (ROS) found in a known biological system.

17 Claims, 27 Drawing Sheets

| Anode | | | | Cathode | | | |
|---|---|---|---|---|---|---|---|
| + | | e-↑ | | e-↓ | | | − |

| Anode | | | Cathode | | | |
|---|---|---|---|---|---|---|
| −1.23 V: $O_2$ :$4H^+$ | 4e ↑ | $2H_2O$ | $2H^+$ | 2e ↓ | $H_2$ | :−0.00V | 1st Generation |
| −0.40V: $O_2$ | 4e ↑ | $4OH^-$ | $2H_2O$ | 2e ↓ | $H_2$ $2OH^-$ | :−0.83V | |
| −.89V: $ClO^-$ :$H_2O$ | 2e ↑ | $2OH^-$ $Cl^-$ | $2H_2O$ | 2e ↓ | $2H^+$ $H_2O_2$ | :1.76V | |
| −1.36 V: $Cl_2$ | 2e ↑ | $2Cl^-$ | $Na^+$ | 1e ↓ | $Na_{(s)}$ | :−2.71V | |
| −1.63V :$2HClO$ :$2H^+$ | 2e ↑ | $Cl_2$ $2H_2O$ | $O_2$ | 1e ↓ | $O_2^{*-}$ | :−0.33V | 2nd Generation |
| −1.67V :$HClO_2$ :$2H^+$ | 2e ↑ | $HClO$ $H_2O$ | $O_2$ $H^+$ | 1e ↓ | $HO_2^*$ | :−0.13V | |
| −2.07V :$O_3$ :$2H^+$ | 2e ↑ | $O_2$ $H_2O$ | $O_2$ $H^+$ | 2e ↓ | $H_2O_2$ | :0.70V | |
| −1.18V :$2ClO_3^-$ $12H^+$ | 10e ↑ | $ICl_2$ $6H_2O$ | $2HClO$ $2H^+$ | 2e ↓ | $Cl_2$ $2H_2O$ | :1.63V | |
| −1.19V :$ClO_2$ :$H^+$ | 1e ↑ | $HClO_2$ $H_2O$ | $HO_2^*$ | 1e ↓ | $H_2O_2$ | :1.51V | 3rd Generation+ |
| −1.18V :$ClO_3^-$ :$2H^+$ | 1e ↑ | $ClO_2$ $H_2O$ | $H_2$ | 2e ↓ | $2H^-$ | :−2.25V | |

*FIG. 2*

FIG. 9
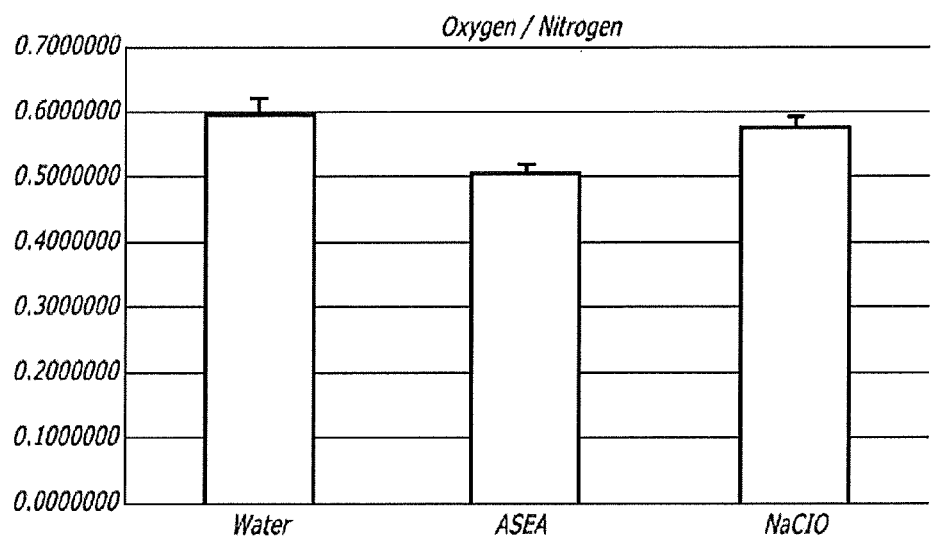
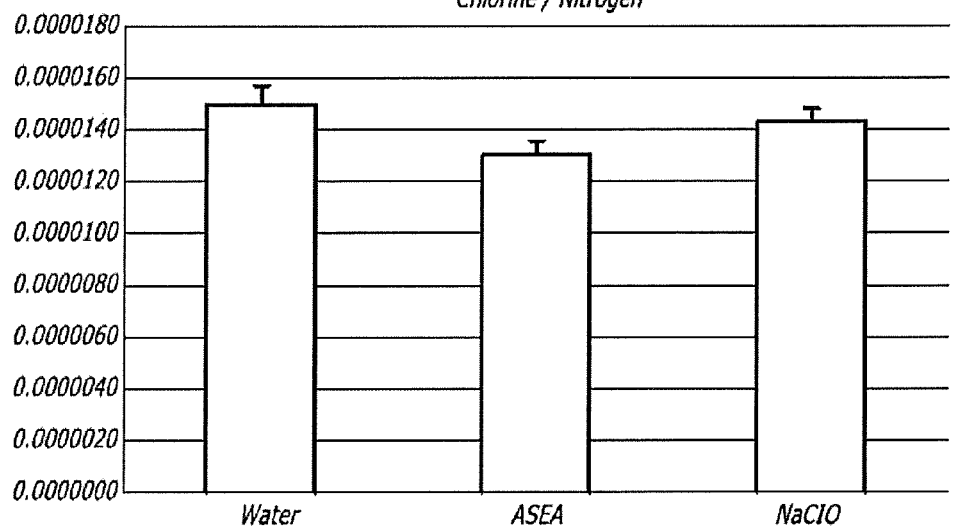
FIG. 10

*FIG. 11*
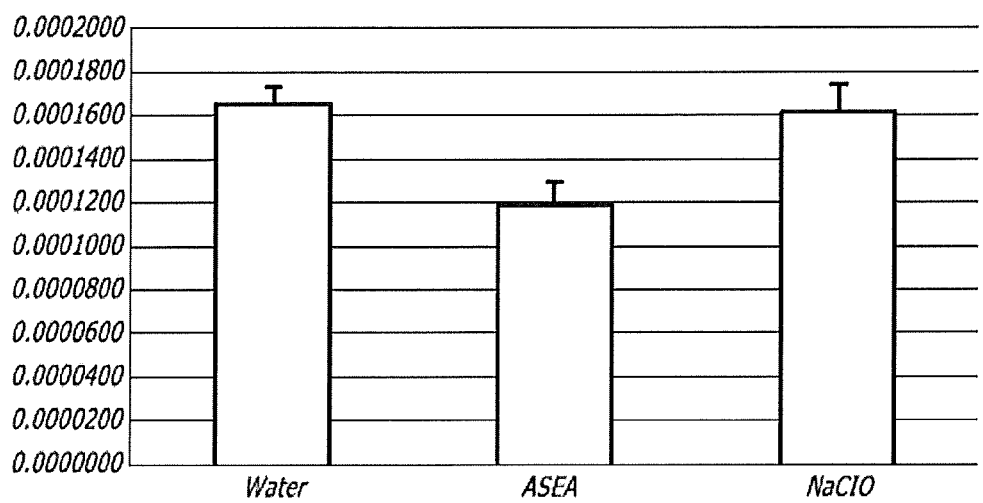
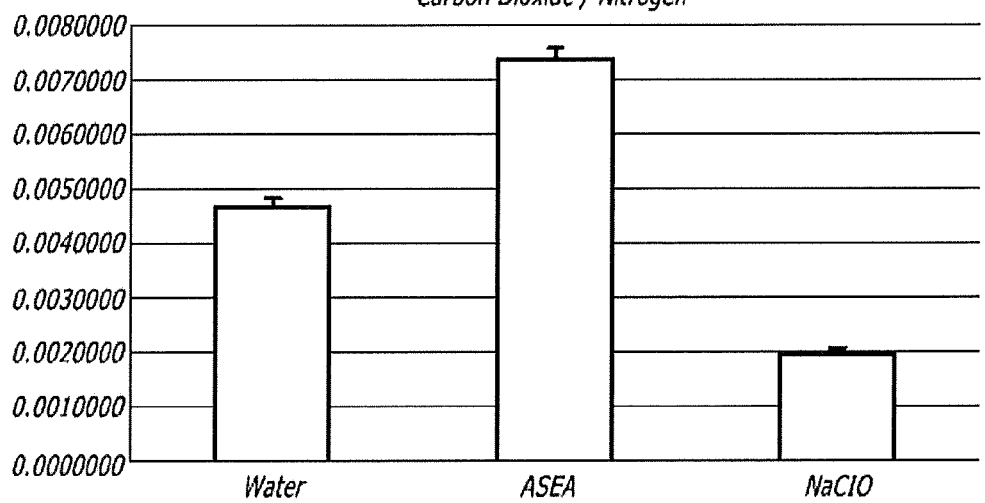
*FIG. 12*

Nuclear NRF2 staining profiles in randomly cycling and serum-starved HMVEC-L cells.

HMVEC-L counts indicate reduced proliferation for high-concentration ASEA after 72 hours

METHODS OF AMELIORATING OXIDATIVE STRESS BY INCREASING THE EFFICIENCY OF GPX AND SOD ACTIVITY

CROSS-REFERENCE TO RELATED APPLICATIONS

This application is a Continuation-in-part of, and claims the benefit of, U.S. patent application Ser. No. 12/592,402, filed Nov. 24, 2009, which is a Continuation-in-part of U.S. patent application Ser. No. 12/383,212, filed Mar. 20, 2009, now U.S. Pat. No. 8,367,120 B1, which is a Continuation-in-Part of U.S. patent application Ser. No. 12/290,398, filed Oct. 30, 2008, now abandoned, which claims priority to U.S. Provisional Patent Application Ser. No. 61/001,010, filed Oct. 30, 2007, the entire contents all of which are herein incorporated by reference in their entirety.

TECHNICAL FIELD

Methods of ameliorating cellular oxidative stress are disclosed.

BACKGROUND

The invention comprises a method to ameliorate cellular oxidative stress comprising a balanced composition of stabilized redox-signaling molecules that is particularly safe and suited for oral consumption. This composition is similar to that of a target composition of redox-signaling molecules that exists naturally inside a healthy human cell. The composition acts to enhance proper immune system function, to enhance the efficiency and production of the body's native antioxidants as well as to enhance the performance of intercellular communications involved in the maintenance of healthy tissues.

Redox signaling deals with the action of a set of several simple reactive signaling molecules that are mostly produced by the mitochondria residing inside human cells during the metabolism of sugars. These reactive signaling molecules are categorized into two general groups, Reactive Oxygen Species (ROS), which contain oxidants, and Reduced Species (RS), which contain reductants. These fundamental universal signaling molecules in the body are the simple but extremely important reactive signaling molecules that are formed from combinations of the atoms (Na, Cl, H, O, N) that are readily found in the saline bath that fills the inside of the cells (cytosol). All of the molecular mechanisms inside healthy cells float around in this saline bath and are surrounded by a balanced mixture of such reactive signaling molecules. A few examples of the more than 20 reactive molecules formed from these atoms inside the cell, some of which are discussed herein, are superoxide, hydrogen peroxide, hypochlorous acid and nitric oxide.

Such reactive signaling molecules are chemically broken down by specialized enzymes placed at strategic locations inside the cell. Some of these protective enzymes are classified as antioxidants such as Glutathione Peroxidase and Superoxide Dismutase. In a healthy cell, the mixtures of these reactive signaling molecules are broken down by the antioxidant enzymes at the same rate that they are produced by the mitochondria. As long as this homeostatic balance is maintained, the cell's chemistry is in balance and all is well.

When damage occurs to the cell, for any number of reasons, including bacterial or viral invasion, DNA damage, physical damage or toxins, this homeostatic balance is disturbed and a build-up of oxidants or reductants occurs in the cell. This condition is known as oxidative stress and it acts as a clear signal to the cell that something is wrong. The cell reacts to this signal by producing the enzymes and repair molecules necessary to attempt repairs to the damage and it also can send messengers to activate the immune system to identify and eliminate threats. If oxidative stress persists in the cell for more than a few hours, then the cell's repair attempts are considered unsuccessful and the cell kills and dismantles itself and is replaced by the natural cellular division of healthy neighboring cells.

On a cellular level, this is essentially the healthy tissue maintenance process: damaged cells are detected and repaired or replaced by healthy cells. This cellular repair and regeneration process is constantly taking place, millions of times an hour, in all parts of the body.

It has long been known that the electrolysis of fluids can result in useful products. Thus, various apparatus and methods have been proposed for electrolyzing saline solution, however, all of the previously available schemes present one or more drawbacks.

For example U.S. Pat. No. 7,691,249 teaches a method an apparatus for making electrolyzed water comprising an insulating end cap for a cylindrical electrolysis cell and is incorporated herein by reference in its entirety.

For example, U.S. Pat. Nos. 4,236,992 and 4,316,787 to Themy disclose an electrode, method and apparatus for electrolyzing dilute saline solutions to produce effective amounts of disinfecting agents such as chlorine, ozone and hydroxide ions. Both of these references are incorporated herein by reference in their entireties U.S. Pat. No. 5,674,537, U.S. Pat. No. 6,117,285 and U.S. Pat. No. 6,007,686 also teach electrolyzed fluids and are now incorporated herein by reference in their entireties.

U.S. Pat. No. 4,810,344 teaches a water electrolyzing apparatus including a plurality of electrolysis devices, each comprising an electrolysis vessel having a cathode and an anode oppose to each other and an electrolysis diaphragm partitioning the space between both of the electrodes wherein the plurality of devices are connected in a series such that only one of the two ionized water discharge channels of the devices constitutes a water supply channel to the device a the succeeding stage and is incorporated herein by reference in its entirety.

U.S. Pat. No. 7,691,249 is now incorporated herein by reference in its entirety and is directed to a method and apparatus for making electrolyzed water.

U.S. Pat. No. 8,062,501 B2 is directed to a method for producing neutral electrolytic water containing OH, D2, HD and HDO as active elements and is incorporated herein by reference in its entirety.

Methods for treatment of physiological fluids using electrolyzed solutions are set forth in U.S. Pat. No. 5,334,383 which is now incorporated herein by reference in its entirety teaches an electrolyzed saline solution, properly made and administered in vivo, as effective in the treatment of various infections brought on by invading antigens and particularly viral infections.

U.S. Pat. No. 5,507,932 which is now incorporated herein by reference in its entirety teaches an apparatus for electrolyzing fluids.

In sum, the art teaches various methods of making electrolyzed fluids but none teaches a stabilized fluid which can ameliorate cellular oxidative stress.

SUMMARY

One method for producing a balanced foundational product to allow the body and immune system to better function, comprises first determining a balanced target mixture of redox-signaling molecules inherent to healthy cells and measuring the concentrations of the reactive molecules contained therein, usually with fluorescent indicators.

This target mixture is then replicated by the electrochemical method of the parent patent application in a process starting with a combination of pure water and salt (NaCl) that undergoes a specific electrochemical processing where the process parameters (temperature, flow, pH, power-source modulation and salt homogeneity and concentration) are varied to produce the ultimate specific target formulation.

The resulting formulation typically has less than about 10% of the recommended daily allowance (RDA) of sodium (usually between 115 mg to 131 mg of sodium per 4 fl. oz. serving) and a pH of between 7.0 and 8.5 with total chlorine less than 40 ppm. These ranges also make the product palatable (won't cause nausea) when taken in 8 oz or larger quantities. The sodium chloride concentration is a variable parameter that can be upwardly adjusted and still produce the desired target composition of the final composition mixture at the expense, of course, of becoming less palatable.

During the electrochemical process, to insure that the saline solution is well mixed, usually homogenizing means are included, such as a fluid circulation device to maintain flow aging stratification and homogeneity of the saline solution during electrolysis.

Next, the temperature and flow of the circulating saline is adjusted to a level to prevent production of chlorates and produce the desired relative concentrations of resulting chemical redox specie components during electrolysis using the apparatus and method disclosed in the parent application. The resultant redox specie components are then measured with the same indicators used to measure the balance of ROS and RS and the other chemical characteristics of the target mixture mentioned above. This process may involve an iterative process where the temperature, flow and other parameters are adjusted until a composition similar to that of the target mixture is achieved.

The resultant composition of reactive signaling molecules is stable with many of its components measurable using standard analytic methods. As discussed above, such signaling molecules are the same as those that are naturally produced inside of living cells and are measured using standard laboratory methods, such as the employment of certain fluorescent dyes that act as indicators. The concentration of some of the individual components of the composition is thus tested and verified in the laboratory.

For example, by regularly utilizing three standard fluorescent indicators, namely R-Phycoerythrin (R-PE), Aminophenyl fluorescein (APF) and Hydroxyphenyl fluorescein (HPF) their corresponding redox specie components can be tracked. Such fluorescent indicator molecules change brightness when they come into contact with specific redox specie. These indicator dyes are very resistant to false positives and are well studied. Such change in fluorescence is then measured using a fluorospectrometer. The change in fluorescence of these indicators quantifies the existence and relative concentration of their corresponding redox specie.

A combination of measurements from these indicators can be utilized to measure the concentration of reactive redox signaling molecules in the test composition and thereby the relative concentration of its major reactive molecular components. Several types of laboratory equipment and methods can also be employed to determine the composition of the proper target solution and that of the resultant electrolyzed composition. One such method is by the proper employment of a Nanodrop™ 3300 fluorospectrometer, made by Thermo Fischer Scientific, along with the R-PE, APF and HPF fluorescent dyes to measure the relative concentrations of reactive signaling molecules inside test compositions. Such measurements can then be compared to measurements taken from a desired target solution. Typically the test RSO Compound is measured along-side the desired target solution.

In one such method, the concentration and presence of such reactive molecules is verified when the three indicators, R-PE, APF and HPF show 1) that a 2 micro molar concentration of R-PE loses 5%-50% of its fluorescence 6 hours after a 1:1000 solution of the RS and ROS is added; 2) and R-PE measurements indicate the same fluorescence levels as a standard ROS generating solution of 0.2 to 1.0 mM AAPH, and 3) the APF measurements indicate the same relative amount as the target compound and 4) HPF measurements indicate a negligibly small reading and 5) the pH is between 7.2 and 7.5 and 6) the total chlorine is less that 35 ppm by weight.

Once the required electrolytic operating parameters are determined for producing the desired composition, the electrochemical device is then activated and adjusted to oxidize and reduce the saline solution in such a way as to produce a composition with similar concentration and mixture of reactive molecules as those present in the healthy target living cells.

The resultant composition is then administered orally or topically to a human as a supplement for the natural redox-signaling compounds formed inside the cells to enhance proper immune system function, to enhance the efficiency and production of the body's native antioxidants as well as to enhance the performance of intercellular communications involved in healthy tissue maintenance and athletic performance.

In summary, the composition of the redox-signaling composition is produced by utilizing an electrochemical process wherein the process parameters (temperature, flow, pH, power-source modulation and salt homogeneity and concentration) are varied until certain chemical indicators measure the same relative composition as compared to a target composition similar to that produced in the cells. The method and composition produced therefrom, thus provides a redox-signaling compound with reactive molecules that mimic those naturally occurring inside one's cells.

The resultant composition produced by the above method was tested to determine its efficacy by independent research. An in-vitro scientific investigation was done in conjunction with a prominent national laboratory to determine the bio-activity of this redox-signaling composition on eukaryotic cells in a controlled environment.

The following is a summary and explanation of the experimental results related to the action of the composition in contact with living human cells. The first part of this investigation was designed to determine if there was a possible toxic response due to contact of the composition with the cells.

When a cell is stressed by a toxin, the cell responds by sending a certain set of transcription factors into the nucleus. Once inside the nucleus, these transcription factors activate the genes responsible for cellular defense and protection against toxins (such as the inflammatory response). The translocation of certain transcription factors into the nucleus can be seen under a fluorescent microscope when the cells are stained by specific indicator dyes.

If the cell undergoes a toxic response, the fluorescent dye is pulled into the nucleus along with the transcription factor. In this experiment two transcription factors, the p65 subunit of NF-kappaB and P-Jun, were monitored. These two transcription factors are known to be activated in all toxic responses. In the photographs from the fluorescent microscopic images of the cells, a toxic response is registered if the green dye is seen to move into the nucleus.

Experimental Procedure: The target eukaryotic cells were cultured in dishes and exposed respectively to (1) Phosphate Buffered Saline (PBS)—the negative control (no toxic response expected), (2) 5% of the RS and ROS-Equivalent to replacing 5% of the nutrient solution (blood plasma) with the composition, (3) 20% of the RS and ROS-Equivalent to replacing 20% of the nutrient solution with the composition, and (4) A known toxin—the positive control (toxic response expected).

The response of the transcription factors, the p65 subunit of NF-kappaB and P-Jun, were photographed under a microscope after exposure to the four solutions listed above. A DAPI stain was also applied to the nuclei in order to help computer software to find the nucleus in the pictures. The software automatically tallied the amount of dye in the nuclei. In the case of P-Jun, measurements of over one hundreds cells were made in order to compile the summary data.

Results for P65/NF-kappaB: In the images cells with stained for the p65 subunit 'of NF-kappaB, it is visually evident that no toxic response is registered for exposure of the cells to the composition compared to the clear positive response is seen in the positive control. The p65 subunit remains on the outside of the nuclei in images of cells with the composition, indicating that no NF-kappaB translocation is detected. There was no toxic response registered by the cells.

Results for P-Jun: As reinforcement of the NF-kappaB results, the P-Jun data also shows visual evidence of no toxic response. It was necessary for the P-Jun data to be averaged over more than 100 cells in order to get statistically significant numerical results. The results clearly show that no significant toxicity exists for the 5% composition and only marginal response for the 20% the composition. Blood concentration for oral doses, however, will never get anywhere near even 1%.

These results are especially interesting considering that large concentrations of almost any compound (including pure water) are known to cause a toxic response in these same kinds of experiments. The non-toxic nature of the composition might be explained by the fact that protective enzymes found in eukaryotic cells are able to neutralize a redox-balanced mixture of reactive signaling molecules, such as that which is found natively inside the cells. The composition contains such a balanced mixture. These observations reinforce the zero-toxicity results of over 10 years of comprehensive toxicity testing done on previous formulations which were produced by similar electrochemical methods.

In the second part of this in-vitro investigation, live cells in culture dishes were exposed to the composition and the bioactivity regarding antioxidant activity of Glutathione Peroxidase (GPx) and Superoxide Dismutase (SOD) as well as the increase in the native production of these antioxidants inside cells was measured.

Experimental Methods for Antioxidant Activity: cells were cultured in several dishes with a bovine serum growth medium. As a primary measure, mouse epithelial-like cells were cultured (these cells react similarly to human cells in most cases) and later human endothelial cells were used to obtain relevant quantitative results.

In the antioxidant enhancement tests, some of the cell cultures were exposed to the composition and others cultures to the same amount of an inert phosphate buffered saline solution (PBS). The antioxidant activity of the cells in each was measured by a purchased kit, Array Design Stressgen kit (#900-158 for GPx activity and #900-157 for SOD activity). The chemical reagents inside these kits measure the ability of the antioxidants in the cell extracts to reduce oxidant activity that occurs naturally when certain oxidizing biological-chemicals are added.

Results of Antioxidant Activity Tests: The first results obtained showed large, well-defined effects. The cell extracts exposed to the composition exhibited eight (8) times the antioxidant efficiency for GPx that those exposed to the inert PBS.

The SOD antioxidant efficiency was slightly less, with about 3 to 5 times enhancements in efficiency. Of note, this efficiency was evident especially at low level concentrations of the composition, tested down to 2.5% of full strength. Increasing the concentration of the composition at high concentrations did not notably increase the antioxidant efficiency; thus there appears to be a very low saturation threshold at low concentrations of GPx. There was some variability in the SOD efficiency tests with SOD concentration that made the confidence level for the accuracy of these tests lower.

It is safe to say that at least a 500% improvement in the overall antioxidant efficiency was seen during these preliminary in vitro tests due to exposure to the composition.

Experimental Methods for Antioxidant Up-regulation: in these experiments, some cultured human endothelial cells were exposed to the composition and others only to an inert phosphate buffer solution (PBS). Standard Western Blot analysis on all cells was done to determine if exposure to the composition activated the nucleus to call for increased production of antioxidants, such as GPx. The concentrations of transcription factors (messengers) in the nucleus that call for up-regulation of antioxidants were also measured in hwnan endothelial cells and compared to cells that had not been exposed to the composition. Results for Antioxidant Production: The results for these tests were extraordinary in several regards. First, there was a slight, 5 to 10%, but real, up-regulation of anti-oxidant production in cells exposed to the composition. This effect was temporary, lasting only about 120 minutes but was clearly visible. The most interesting result, however, is that exposure to the composition at any concentration did not invoke the normal inflammatory transcription factor (NF-kappaB) and yet did invoke the antioxidant transcription factor (NRF2). Stimulating the production of antioxidants without stimulation of low-level inflammation is very rare and has stirred some interest in the scientific community. With the antioxidant up-regulation transcription factor NRF2, positive movement of this transcription factor was seen in both the cells exposed to the composition and in the positive control. Averages over hundreds of cells were observed in order to obtain these results. These results were also verified by the Western Blot analysis showing clear responses in the increase of antioxidants upon exposure to the composition relative to the PBS saline control. It is generally established that such increased efficiency in antioxidant action and production as well as activation of the cell's innate protective responses (especially without inflammatory responses) slows down the tissue aging process and results in more efficient healthy cellular maintenance processes.

Mammalian cells utilize RS/ROS in a variety of biological processes. RS/ROS are produced in large amounts in the cell during the metabolism of sugar, specifically by the oxidative phosphorylation process in the mitochondria.

RS are electron acceptors and include for example HOCl, NaClO, O2, H2, $H^+$, ClO, $Cl_2$, $H_2O_2$ and ROS are electron donors and include for example $O_2^-$, $HO_2$, $Cl^-$, $H^-$, *OCl, $O_3$, $*O_2^-$ and $OH^-$.

Embodiments include a method of treating an oxidative stress related disorder, such method including administering a composition including at least one species selected from $O_2$, $H_2$, $Cl_2$, $OCl^-$, HOCl, NaOCl, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O$, $OH^{*-}$, $HOCl-O_2^{*-}$, $HOCl-O_3$, $O_2^{*-}$, $HO_2^*$, NaCl, HCl, NaOH, water clusters, or a combination thereof to a patient experiencing oxidative stress; and treating the oxidative stress related disorder.

In one embodiment, the invention is directed to a method of reducing or ameliorating cellular oxidative stress comprising contacting at least one cell with a composition comprising a mixture of reduced species (RS) and reactive oxygen species (ROS) wherein the mixture of reduced species (RS) and reactive oxygen species (ROS) mirrors a target mixture wherein the target mixture is the reduced species (RS) and reactive oxygen species (ROS) found in a known biological system.

In another embodiment, the reactive oxygen species (ROS) comprises a superoxide.

In a further embodiment, the superoxide is *O2–.

In one instance, the reduced species (RS) comprises at least one hypochlorite.

In another instance, the reduced species (RS) include HOCl, NaClO, O2, H2, H+, ClO, Cl2, and H2O2 and the reactive oxygen species (ROS) include O2–, HO2, Cl–, H–, *OCl, O3, *O2– and OH–.

In a further instance, the concentration and presence of the reactive oxygen species (ROS) is verified when the three indicators, R-PE, APF and HPF show 1) that a 2 micro molar concentration of R-PE loses 5%-50% of its fluorescence 6 hours after a 1:1000 solution of the RS and ROS is added; 2) and R-PE measurements indicate the same fluorescence levels as a standard ROS generating solution of 0.2 to 1.0 mM AAPH, and 3) the APF measurements indicate the same relative amount as the target mixture and 4) HPF measurements indicate a negligibly small reading.

In one embodiment, the mixture of reduced species (RS) and reactive oxygen species (ROS) is made by electrolyzing a homogenous and well mixed solution of saline and water.

In another embodiment, the temperature, flow and electrical current are adjusted until a composition similar to that of the target mixture is achieved.

In a further embodiment, the temperature is between 30-100° F.

In one embodiment, the invention is directed to a method further comprising increasing the efficiency of at least one enzyme.

In one instance, the invention is directed to a method wherein the enzyme is glutathione peroxidase or superoxide dismutase.

In another instance, the invention is directed to a method wherein the enzyme is glutathione peroxidase and superoxide dismutase.

In one embodiment, the invention is directed to a method wherein there is an improvement in antioxidant efficiency of at least 500%.

In one embodiment, the invention is directed to a method further comprising inhibiting the translocation of NFkB or pJUN.

In one embodiment, the invention is directed to a method further comprising inhibiting the translocation of NFkB and pJUN.

In one embodiment, the invention is directed to a method further comprising decreasing or reducing cellular oxidative damage done by oxidants.

In one embodiment, the invention is directed to a method further comprising restoring a healthy concentration of reduced species (RS) and reactive oxygen species (ROS) to a damaged or stressed cell.

In one embodiment, the invention is directed to a method further comprising administering to a subject a serving of the composition wherein the serving is 4 fl oz.

In one embodiment, the invention is directed to a method further comprising decreasing oxidants in a cell wherein there is no corresponding change in nuclear transcription factors wherein the nuclear transcription factors are selected from the group consisting of NF-kBeta, NRF2 and combinations thereof.

BRIEF DESCRIPTION OF THE DRAWINGS

FIG. 2 illustrates an example diagram of the generation of various molecules at the electrodes. The molecules written between the electrodes depict the initial reactants and those on the outside of the electrodes depict the molecules/ions produced at the electrodes and their electrode potentials.

FIG. 9 illustrates oxygen/nitrogen ratios for a composition described herein compared to water and NaClO (the composition is labeled "ASEA").

FIG. 10 illustrates chlorine/nitrogen ratios for a composition described herein compared to water and NaClO (the composition is labeled "ASEA").

FIG. 11 illustrates ozone/nitrogen ratios for a composition described herein compared to water and NaClO (the composition is labeled "ASEA").

FIG. 12 illustrates the carbon dioxide to nitrogen ratio of a composition as described herein compared to water and NaClO (the composition is labeled "ASEA").

DETAILED DESCRIPTION

Figure 1:
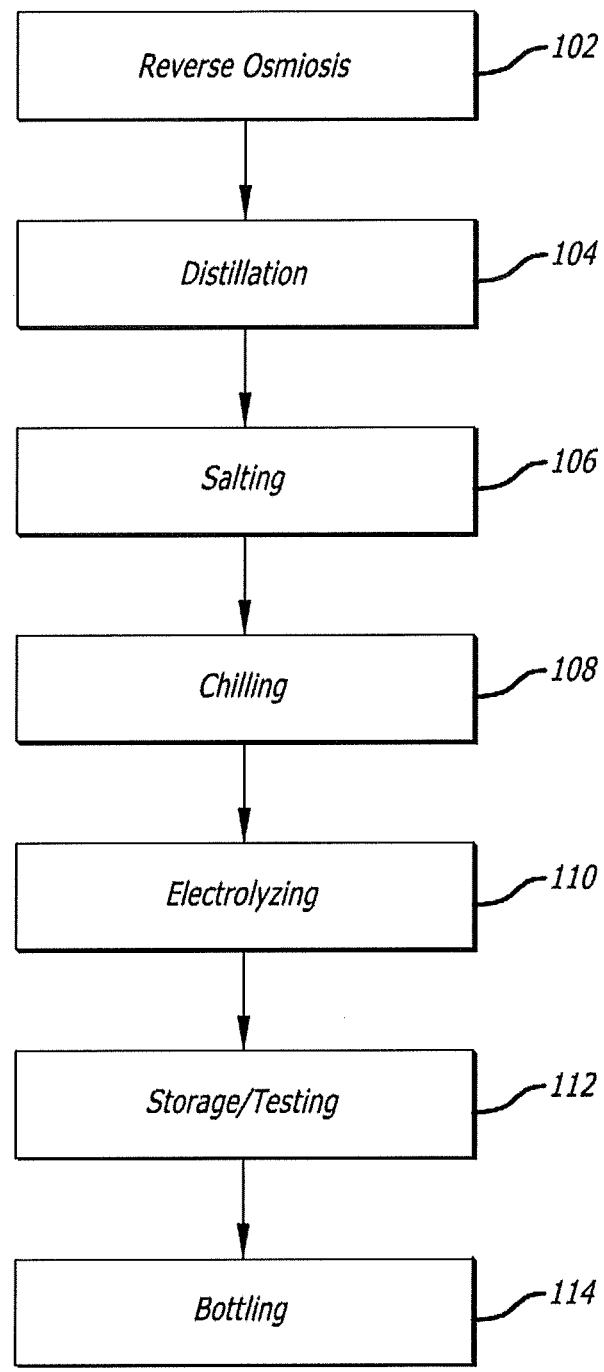
FIG. 1 is a flow chart of a process as described herein.

Described herein are compositions including fluids that can be administered to a subject, that generally include at least one redox signaling agent (RXN). RXNs can include, but are not limited to superoxides: $O_2^{*-}$, $HO_2^*$; hypochlorites: $OCl^-$, $HOCl$, $NaOCl$; hypochlorates: $HClO_2$, $ClO_2$, $HClO_3$, $HClO_4$; oxygen derivatives: $O_2$, $O_3$, $O_4^{*-}$, $1O$; hydrogen derivatives: $H_2$, $H^-$; hydrogen peroxide: $H_2O_2$; hydroxyl free Radical: $OH^{*-}$; ionic compounds: $Na^+$, $Cl^-$, $H^+$, $OH^-$, $NaCl$, $HCl$, $NaOH$; chlorine: $Cl_2$; water clusters: n*$H_2O$-induced dipolar layers around ions and combinations thereof. Some RXNs are electron acceptors (RS) and include $HOCl$, $NaClO$, $O2$, $H2$, $H^+$, $ClO$, $Cl_2$, $H_2O_2$ and some are electron donors (ROS) and include $O_2^-$, $HO_2$, $Cl^-$, $H^-$, $*OCl$, $O_3$, $*O2^-$ and $OH^-$.

Methods of making therapeutic compositions are described comprising: electrolyzing salinated water having a salt concentration of about 10 g NaCl/gal, such as 10.75 g NaCl/gal using a set of electrodes with an amperage of about 50-60 amps, such as 56 amps to form a life enhancing composition, wherein the water is chilled below room temperature and the water is circulated during electrolyzing.

A method of producing the disclosed compositions can include one or more of the steps of (1) preparation of an ultra-pure homogeneous solution of sodium chloride in water, (2) temperature control and flow regulation through a set of inert catalytic electrodes and (3) a modulated electrolytic process that results in the formation of such stable molecular moieties and complexes. In one embodiment, such a process includes all these steps.

The saline generally should be free from contaminants, both organic and inorganic, and homogeneous down to the molecular level. In particular, metal ions can interfere with the electro-catalytic surface reactions, and thus it may be helpful for metals to be avoided. In one embodiment, a brine solution is used to salinate the water. The brine solution can have a NaCl concentration of about 540 g NaCl/gal, such as 537.5 g NaCl/gal. In one embodiment, the composition can include at least one species such as $O_2$, $H_2$, $Cl_2$, $OCl^-$, $HOCl$, $NaOCl$, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O$, $OH^{*-}$, $HOCl—O_2^{*-}$, $HOCl—O_3$, $O_2^{*-}$, $HO_2^*$, $NaCl$, $HCl$, $NaOH$, water clusters, or a combination thereof.

In one embodiment, the composition can include at least one species such as $H_2$, $Cl_2$, $OCl^-$, $HOCl$, $NaOCl$, $HClO_2$, $ClO_2$, $HClO_3$, $HClO_4$, $H_2O_2$, $O_3$, $O_4^{*-}$, $^1O_2$, $OH^{*-}$, $HOCl—O_2^{*-}$, $HOCl—O_3$, $O_2^{*-}$, $HO_2^*$, water clusters, or a combination thereof.

In one embodiment, the composition can include at least one species such as $HClO_3$, $HClO_4$, $H_2O_2$, $O_3$, $O_4^{*-}$, $^1O_2$, $OH^{*-}$, $HOCl—O_2^{*-}$, $HOCl—O_3$, $O_2^{*-}$, $HO_2^*$, water clusters, or a combination thereof.

In one embodiment, the composition can include at least $O_2^{*-}$ and $HOCl$.

In one embodiment, the composition can include $O_2$. In one embodiment, the composition can include $H_2$. In one embodiment, the composition can include $Cl_2$. In one embodiment, the composition can include $OCl^-$. In one embodiment, the composition can include $HOCl$. In one embodiment, the composition can include $NaOCl$. In one embodiment, the composition can include $HClO_2$. In one embodiment, the composition can include $ClO_2$. In one embodiment, the composition can include $HClO_3$. In one embodiment, the composition can include $HClO_4$. In one embodiment, the composition can include $H_2O_2$. In one embodiment, the composition can include $Na^+$. In one embodiment, the composition can include $Cl^-$. In one embodiment, the composition can include $H^+$. In one embodiment, the composition can include $H^-$. In one embodiment, the composition can include $OH^-$. In one embodiment, the composition can include $O_3$. In one embodiment, the composition can include $O_4^{*-}$. In one embodiment, the composition can include $^1O_2$. In one embodiment, the composition can include $OH^{*-}$. In one embodiment, the composition can include $HOCl—O_2^{*-}$. In one embodiment, the composition can include $HOCl—O_3$. In one embodiment, the composition can include $O_2^{*-}$. In one embodiment, the composition can include $HO_2^*$. In one embodiment, the composition can include $NaCl$. In one embodiment, the composition can include $HCl$. In one embodiment, the composition can include NaOH. In one embodiment, the composition can include water clusters. Embodiments can include combinations thereof.

With this in mind, a step in such a process is shown in FIG. 1. 100 is an optional reverse osmosis procedure 102. Water can be supplied from a variety of sources, including but not limited to municipal water, filtered water, nanopure water, or the like.

The reverse osmosis process can vary, but can provide water having a total dissolved solids content of less than about 10 ppm, about 9 ppm, about 8 ppm, about 7 ppm, about 6 ppm, about 5 ppm, about 4 ppm, about 3 ppm, about 2 ppm, about 1 ppm, or the like.

The reverse osmosis process can be performed at a temperature of about 5° C., about 10° C., about 15° C., about 20° C., about 25° C., about 30° C., about 35° C., or the like. The reverse osmosis step can be repeated as needed to achieve a particular total dissolved solids level. Whether the optional reverse osmosis step is utilized, an optional distillation step 104 can be performed.

Other means of reducing contaminants include filtration and/or purification such as by utilizing deionization, carbon filtration, double-distillation, electrodeionization, resin filtration such as with Milli-Q purification, microfiltration, ultrafiltration, ultraviolet oxidation, electrodialysis, or combinations thereof.

The distillation process can vary, but can provide water having a total dissolved solids content of less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or the like. The temperature of the distillation process can be performed at a temperature of about 5° C., about 10° C., about 15° C., about 20° C., about 25° C., about 30° C., about 35° C., or the like.

The distillation step can be repeated as needed to achieve a particular total dissolved solids level. After water has been subjected to reverse osmosis, distillation, both, or neither, the level of total dissolved solids in the water can be less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or the like.

The reverse osmosis, distillation, both, or neither, can be preceded by a carbon filtration step.

Purified water can be used directly with the systems and methods described herein.

In one embodiment, contaminants can be removed from a commercial source of water by the following procedure: water flows through an activated carbon filter to remove the aromatic and volatile contaminants and then undergoes Reverse Osmosis (RO) filtration to remove dissolved solids and most organic and inorganic contaminants. The resulting filtered RO water can contain less than about 8 ppm of dissolved solids. Most of the remaining contaminants can be removed through a distillation process, resulting in dissolved solid measurements less than 1 ppm. In addition to removing contaminants, distillation may also serve to condition the water with the correct structure and Oxidation Reduction Potential (ORP) to facilitate the oxidative and reductive reaction potentials on the platinum electrodes in the subsequent electro-catalytic process.

After water has been subjected to reverse osmosis, distillation, both or neither, a salt is added to the water in a salting step 106. The salt can be unrefined, refined, caked, de-caked, or the like. In one embodiment, the salt is sodium chloride (NaCl). In some embodiments, the salt can include an additive. Salt additives can include, but are not limited to potassium iodide, sodium iodidie, sodium iodate, dextrose, sodium fluoride, sodium ferrocyanide, tricalcium phosphate, calcium carbonate, magnesium carbonate, fatty acids, magnesium oxide, silicone dioxide, calcium silicate, sodium aluminosilicate, calcium aluminosilicate, ferrous fumarate, iron, or folic acid. Any of these additives can be added at this point or at any point during the described process. For example, the above additives can be added just prior to bottling.

In another embodiment, the process can be applied to any ionic, soluble salt mixture, especially with those containing chlorides. In addition to NaCl, other non-limiting examples include LiCl, HCl, CuCl2, CuSO4, KCl, MgCl, CaCl2, sulfates and phosphates. For example, strong acids such as sulfuric acid (H2SO4), and strong bases such as potassium hydroxide (KOH), and sodium hydroxide (NaOH) are frequently used as electrolytes due to their strong conducting abilities. Preferably the salt is sodium chloride (NaCl). A brine solution can be used to introduce the salt into the water. The amount of brine or salt needs will be apparent to one of ordinary skill in the art.

Salt can be added to water in the form of a brine solution. To mix the brine solution, a physical mixing apparatus can be used or a circulation or recirculation can be used. In one embodiment, pure pharmaceutical grade sodium chloride is dissolved in the prepared distilled water to form a 15 wt % sub-saturated brine solution and continuously re-circulated and filtered until the salt has completely dissolved and all particles >0.1 microns are removed. This step can take several days. The filtered, dissolved brine solution is then injected into tanks of distilled water in about a 1:352 ratio (salt:water) in order to form a 0.3% saline solution. In one embodiment, a ratio 10.75 g of salt per 1 gallon of water can be used to form the composition. In another embodiment, 10.75 g of salt in about 3-4 g of water, such as 3,787.5 g of water can be used to form the composition. This solution then can be allowed to re-circulate and diffuse until homogeneity at the molecular scale has been achieved.

In one embodiment, the homogenous saline solution is chilled to about 4.8±0.5° C. Temperature regulation during the entire electro-catalytic process is typically required as thermal energy generated from the electrolysis process itself may cause heating. In one embodiment, process temperatures at the electrodes can be constantly cooled and maintained at about 4.8° C. throughout electrolysis.

Brine can then be added to the previously treated water or to fresh untreated water to achieve a NaCl concentration of between about 1 g NaCl/gal water and about 25 g NaCl/gal water, between about 8 g NaCl/gal water and about 12 g NaCl/gal water, or between about 4 g NaCl/gal water and about 16 g NaCl/gal water. Once brine is added to water at an appropriate amount, the solution can be thoroughly mixed. The temperature of the liquid during mixing can be at room temperature or controlled to a desired temperature or temperature range.

To mix the solution, a physical mixing apparatus can be used or a circulation or recirculation can be used. The salt solution can then be chilled in a chilling step 108.

For large amounts of composition, various chilling and cooling methods can be employed. For example cryogenic cooling using liquid nitrogen cooling lines can be used. Likewise, the solution can be run through propylene glycol heat exchangers to achieve the desired temperature. The chilling time can vary depending on the amount of liquid, the starting temperature and the desired chilled temperature.

Products from the anodic reactions can be effectively transported to the cathode to provide the reactants necessary to form the stable complexes on the cathode surfaces. Maintaining a high degree of homogeneity in the fluids circulated between the catalytic surfaces can also be helpful. A constant flow of about 2-8 mL/cm² per sec can be used, with typical mesh electrode distances 2 cm apart in large tanks. This flow can be maintained, in part, by the convective flow of gasses released from the electrodes during electrolysis.

The mixed solution, chilled or not, can then undergo electrochemical processing through the use of at least one electrode in an electrolyzing step 110. Each electrode can be or include a conductive metal. Metals can include, but are not limited to copper, aluminum, titanium, rhodium, platinum, silver, gold, iron, a combination thereof or an alloy such as steel or brass. The electrode can be coated or plated with a different metal such as, but not limited to aluminum, gold, platinum or silver. In an embodiment, each electrode is formed of titanium and plated with platinum. The platinum surfaces on the electrodes by themselves can be optimal to catalyze the required reactions. Rough, double layered platinum plating can assure that local "reaction centers" (sharply pointed extrusions) are active and that the reactants not make contact with the underlying electrode titanium substrate.

In one embodiment, rough platinum-plated mesh electrodes in a vertical, coaxial, cylindrical geometry can be optimal, with, for example, not more than 2.5 cm, not more than 5 cm, not more than 10 cm, not more than 20 cm, or not more than 50 cm separation between the anode and cathode. The amperage run through each electrode can be between about 2 amps and about 15 amps, between about 4 amps and about 14 amps, at least about 2 amps, at least about 4 amps, at least about 6 amps, or any range created using any of these values. In one embodiment, 7 amps is used with each electrode.

The amperage can be running through the electrodes for a sufficient time to electrolyze the saline solution. The solution can be chilled during the electrochemical process. The solution can also be mixed during the electrochemical process. This mixing can be performed to ensure substantially complete electrolysis.

Electric fields between the electrodes can cause movement of ions. Negative ions can move toward the anode and positive ions toward the cathode. This can enable exchange of reactants and products between the electrodes. In some embodiments, no barriers are needed between the electrodes.

After amperage has been run through the solution for a sufficient time, an electrolyzed solution is created. The solution can be stored and or tested for particular properties in storage/testing step 112.

The end products of this electrolytic process can react within the saline solution to produce many different chemical entities. The compositions and composition described herein can include one or more of these chemical entities, known as redox signaling agents or RXNs.

The chlorine concentration of the electrolyzed solution can be between about 5 ppm and about 34 ppm, between about 10 ppm and about 34 ppm, or between about 15 ppm and about 34 ppm. In one embodiment, the chlorine concentration is about 32 ppm.

The saline concentration in the electrolyzed solution can be, for example, between about 0.10% w/v and about 0.20% w/v, between about 0.11% w/v and about 0.19% w/v, between about 0.12% w/v and about 0.18% w/v, between about 0.13% w/v and about 0.17% w/v, or between about 0.14% w/v and about 0.16% w/v.

The composition generally can include electrolytic and/or catalytic products of pure saline that mimic redox signaling molecular compositions of the native salt water compounds found in and around human cells. The composition can be fine tuned to mimic or mirror molecular compositions of different biological media. The composition can have reactive species other than chlorine present. As described, species present in the compositions described herein can include, but are not limited to $O_2$, $H_2$, $Cl_2$, $OCl^-$, $HOCl$, $NaOCl$, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O_2$, $OH^{*-}$, $HOCl-O_2^{*-}$, $HOCl-O_3$, $O_2^{*-}$, $HO_2^*$, $NaCl$, $HCl$, $NaOH$, and water clusters: $n*H_2O$-induced dipolar layers around ions, and the like.

The life enhancing beverage can then be bottled in a bottling step 114. The beverage can be bottled in plastic bottles having volumes of about 4 oz, about 8 oz, about 16 oz, about 32 oz, about 48 oz, about 64 oz, about 80 oz, about 96 oz, about 112 oz, about 128 oz, about 144 oz, about 160 oz, or any range created using any of these values. The plastic bottles can also be plastic squeezable pouches having similar volumes. In one embodiment, plastic squeezable pouches can have one way valves to prevent leakage of the life enhancing beverage, for example, during athletic activity.

During bottling, solution from an approved batch can be pumped through a 10 micron filter (e.g., polypropylene) to remove any larger particles from tanks, dust, hair, etc. that might have found their way into the batch. In other embodiments, this filter need not be used. Then, the solution can be pumped into the bottles, the overflow going back into the batch.

Bottles generally may not contain any dyes, metal specks or chemicals that can be dissolved by acids or oxidating agents. The bottles, caps, bottling filters, valves, lines and heads used can be specifically be rated for acids and oxidating agents. Caps and with organic glues, seals or other components sensitive to oxidation may be avoided, as these could neutralize and weaken the product over time.

The bottles and pouches used herein can aid in preventing decay of free radical species found within the beverages. In other embodiments, the bottles and pouches described do not further the decay process. In other words, the bottles and pouches used can be inert with respect to the radical species in the beverages. In one embodiment, a container (e.g., bottle and/or pouch) can allow less than about 10% decay/month, less than about 9% decay/month, less than about 8% decay/month, less than about 7% decay/month, less than about 6% decay/month, less than about 5% decay/month, less than about 4% decay/month, less than about 3% decay/month, less than about 2% decay/month, less than about 1% decay/month, between about 10% decay/month and about 1% decay/month, between about 5% decay/month and about 1% decay/month, about 10% decay/month, about 9% decay/month, about 8% decay/month, about 7% decay/month, about 6% decay/month, about 5% decay/month, about 4% decay/month, about 3% decay/month, about 2% decay/month, or about 1% decay/month of free radicals in the beverage. In one embodiment, a bottle can only result in about 3% decay/month of superoxide. In another embodiment, a pouch can only result in about 4% decay/month of superoxide.

In the mitochondria, fluctuations of the mitochondrial potential, specifically pulsing of the potentials have been seen to take place. Pulsing potentials in the power supply of the production units can also be built in. Lack of filter capacitors in the rectified power supply can cause the voltages to drop to zero 120 times per second, resulting in a hard spike when the alternating current in the house power lines changes polarity. This hard spike, under Fourier transform, can emit a large bandwidth of frequencies. In essence, the voltage is varying from high potential to zero 120 times a second. In other embodiments, the voltage can vary from high potential to zero about 1,000 times a second, about 500 times a second, about 200 times a second, about 150 times a second, about 120 times a second, about 100 times a second, about 80 times a second, about 50 times a second, about 40 times a second, about 20 times a second, between about 200 times a second and about 20 times a second, between about 150 times a second and about 100 times a second, at least about 100 times a second, at least about 50 times a second, or at least about 120 times a second. This power modulation can allow the electrodes sample all voltages and also provides enough frequency bandwidth to excite resonances in the forming molecules themselves. The time at very low voltages can also provide an environment of low electric fields where ions of similar charge can come within close proximity to the electrodes. All of these factors together can provide a possibility for the formation of stable complexes capable of generating and preserving ROS free radicals.

Waveforms with an alternating current (AC) ripple can be used to provide power to the electrodes. Such an AC ripple can also be referred to as pulse or spiking waveforms and include: any positive pulsing currents such as pulsed waves, pulse train, square wave, sawtooth wave, pulse-width modulation (PWM), pulse duration modulation (PDM), single phase half wave rectified AC, single phase full wave rectified AC or three phase full wave rectified for example.

A bridge rectifier may be used. Other types of rectifiers can be used such as Single-phase rectifiers, Full-wave rectifiers, Three-phase rectifiers, Twelve-pulse bridge, Voltage-multiplying rectifiers, filter rectifier, a silicon rectifier, an SCR type rectifier, a high-frequency (RF) rectifier, an inverter digital-controller rectifier, vacuum tube diodes, mercury-arc valves, solid-state diodes, silicon-controlled rectifiers and the like. Pulsed waveforms can be made with a transistor regulated power supply, a dropper type power supply, a switching power supply and the like.

This pulsing waveform model can be used to stabilize superoxides, hydroxyl radicals and OOH* from many different components and is not limited to any particular variable such as voltage, amps, frequency, flux (current density) or current. The variables are specific to the components used. For example, water and NaCl can be combined which provide molecules and ions in solution. A 60 Hz current can be used, meaning that there are 60 cycles/120 spikes in the voltage (V) per second or 120 times wherein the V is 0 each second. When the V goes down to 0 it is believe that the 0 V allows for ions to drift apart/migrate and reorganize before the next increase in V. It is theorized that this spiking in V allows for and promotes a variable range of frequencies influencing many different types of compounds and/or ions so that this process occurs.

Diodes may also be used. The V may drop to 0 as many times per second as the frequency is adjusted. As the frequency is increased the number of times the V drops is increased.

When the ions are affected by the electricity from the electrodes, they change. Without being bound by theory, it is believed that the electricity alters the state of some of the ions/compounds. This alteration results in the pushing of electrons out of their original orbit and/or spin state into a higher energy state and/or a single spin state. This electrolysis provides the energy to form free radicals which are ultimately formed during a multi-generational cycling of reactants and products during the electrolysis process. In other words, compounds and/or ions are initially electrolyzed so that the products that are formed are then themselves reacted with other compounds and/or ions and/or gas to form a second generation of reactants and products. This generational process then happens again so that the products from the second generation react with other compounds and/or ions in solution when the voltage spikes again.

The redox potential can be about 840 mV.

The frequency can be from about 1 Hz to infinity or to about 100 MHz.

Again referencing FIG. 2, FIG. 2 illustrates an example diagram of the generation of various molecules at the electrodes, the molecules written between the electrodes depict the initial reactants and those on the outside of the electrodes depict the molecules/ions produced at the electrodes and their electrode potentials. The diagram is broken into generations where each generation relies on the products of the subsequent generations.

The end products of this electrolytic process can react within the saline solution to produce many different chemical entities. The compositions and beverage described herein can include one or more of these chemical entities. These end products can include, but are not limited to superoxides: $O_2^{*-}$, $HO_2^*$; hypochlorites: $OCl-$, $HOCl$, $NaOCl$; hypochlorates: $HClO2$, $ClO2$, $HClO3$, $HClO4$; oxygen derivatives: $O2$, $O3$, $O4^{*-}$, $1O$; hydrogen derivatives: $H2$, $H-$; hydrogen peroxide: $H2O2$; hydroxyl free Radical: $OH^{*-}$; ionic compounds: $Na+$, $Cl-$, $H+$, $OH-$, $NaCl$, $HCl$, $NaOH$; chlorine: $Cl2$; and water clusters: $n*H2O$-induced dipolar layers around ions, several variations.

In order to determine the relative concentrations and rates of production of each of these during electrolysis, certain general chemical principles can be helpful:

1) A certain amount of Gibbs free energy is required for construction of the molecules; Gibbs free energy is proportional to the differences in electrode potentials listed in FIG. 2. Reactions with large energy requirements are less likely to happen, for example an electrode potential of −2.71V (compared to Hydrogen reduction at 0.00V) is required to make sodium metal:

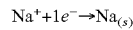
$Na^+ + 1e^- \rightarrow Na_{(s)}$

Such a large energy difference requirement makes this reaction less likely to happen compared to other reactions with smaller energy requirements. Electron(s) from the electrodes may be preferentially used in the reactions that require lesser amounts of energy, such as the production of hydrogen gas.

2) Electrons and reactants are required to be at the same micro-locality on the electrodes. Reactions that require several reactants may be less likely to happen, for example:

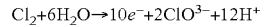
$Cl_2 + 6H_2O \rightarrow 10e^- + 2ClO_3^- + 12H^+$ requires that 6 water molecules and a Cl2 molecule to be at the electrode at the same point at the same time and a release of 10 electrons to simultaneously occur. The probability of this happening generally is smaller than other reactions requiring fewer and more concentrated reactants to coincide, but such a reaction may still occur.

3) Reactants generated in preceding generations can be transported or diffuse to the electrode where reactions happen. For example, dissolved oxygen (O2) produced on the anode from the first generation can be transported to the cathode in order to produce superoxides and hydrogen peroxide in the second generation. Ions can be more readily transported: they can be pulled along by the electric field due to their electric charge. In order for chlorates, to be generated, for example, HClO2 can first be produced to start the cascade, restrictions for HClO2 production can also restrict any subsequent chlorate production. Lower temperatures can prevent HClO2 production.

Stability and concentration of the above products can depend, in some cases substantially, on the surrounding environment. The formation of complexes and water clusters can affect the lifetime of the moieties, especially the free radicals.

In a pH-neutral aqueous solution (pH around 7.0) at room temperature, superoxide free radicals (O2*−) have a half-life of 10's of milliseconds and dissolved ozone (O3) has a half-life of about 20 min. Hydrogen peroxide (H2O2) is relatively long-lived in neutral aqueous environments, but this can depend on redox potentials and UV light. Other entities such as HCl and NaOH rely on acidic or basic environments, respectively, in order to survive. In pH-neutral solutions, H+ and OH− ions have concentrations of approximately 1 part in 10,000,000 in the bulk aqueous solution away from the electrodes. H− and 1O can react quickly. The stability of most of these moieties mentioned above can depend on their microenvironment.

Superoxides and ozone can form stable Van de Waals molecular complexes with hypochlorites. Clustering of polarized water clusters around charged ions can also have the effect of preserving hypochlorite-superoxide and hypochlorite-ozone complexes. Such complexes can be built through electrolysis on the molecular level on catalytic substrates, and may not occur spontaneously by mixing together components. Hypochlorites can also be produced spontaneously by the reaction of dissolved chlorine gas (Cl2) and water. As such, in a neutral saline solution the formation of on or more of the stable molecules and complexes may exist: dissolved gases: O2, H2, Cl2; hypochlorites: OCl−, HOCl, NaOCl; hypochlorates: HClO2, ClO2, HClO3, HClO4; hydrogen peroxide: H2O2; ions: Na+, Cl−, H+, H−, OH−; ozone: O3, O4*−; singlet oxygen: 1O; hydroxyl free radical: OH*−; superoxide complexes: HOCl—O2*−; and ozone complexes: HOCl—O3. One or more of the above molecules can be found within the compositions and beverages described herein.

A complete quantum chemical theory can be helpful because production is complicated by the fact that different temperatures, electrode geometries, flows and ion transport mechanisms and electrical current modulations can materially change the relative/absolute concentrations of these components, which could result in producing different distinct compositions. As such, the selection of production parameters can be critical. The amount of time it would take to check all the variations experimentally may be prohibitive.

After amperage has been run through the solution for a sufficient time, an electrolyzed solution is created with beneficial properties, such as a life enhancing beverage. The solution can have a pH of about 7.4. In some embodiments, the pH is greater than 7.3. In some embodiments, the pH is not acidic. In other embodiments, the solution can have a pH less than about 7.5. The pH may not be basic. The solution can be stored and or tested for particular properties in a storage/testing step 112.

The chlorine concentration of the electrolyzed solution can be about 5 ppm, about 10 ppm, about 15 ppm, about 20 ppm, about 21 ppm, about 22 ppm, about 23 ppm, about 24 ppm, about 25 ppm, about 26 ppm, about 27 ppm, about 28 ppm, about 29 ppm, about 30 ppm, about 31 ppm, about 32 ppm, about 33 ppm, about 34 ppm, about 35 ppm, about 36 ppm, about 37 ppm, about 38 ppm, less than about 38 ppm, less than about 35 ppm, less than about 32 ppm, less than about 28 ppm, less than about 24 ppm, less than about 20 ppm, less than about 16 ppm, less than about 12 ppm, less than about 5 ppm, between about 30 ppm and about 34 ppm, between about 28 ppm and about 36 ppm, between about 26 ppm and about 38 ppm, between about 20 ppm and about 38 ppm, between about 5 ppm and about 34 ppm, between about 10 ppm and about 34 ppm, or between about 15 ppm and about 34 ppm. In one embodiment, the chlorine concentration is about 32 ppm. In another embodiment, the chlorine concentration is less than about 41 ppm.

The saline concentration in the electrolyzed solution can be about 0.10% w/v, about 0.11% w/v, about 0.12% w/v, about 0.13% w/v, about 0.14% w/v, about 0.15% w/v, about 0.16% w/v, about 0.17% w/v, about 0.18% w/v, about 0.19% w/v, about 0.20% w/v, about 0.30% w/v, about 0.40% w/v, about 0.50% w/v, about 0.60% w/v, about 0.70% w/v, between about 0.10% w/v and about 0.20% w/v, between about 0.11% w/v and about 0.19% w/v, between about 0.12% w/v and about 0.18% w/v, between about 0.13% w/v and about 0.17% w/v, or between about 0.14% w/v and about 0.16% w/v.

The beverage generally can include electrolytic and/or catalytic products of pure saline that mimic redox signaling molecular compositions of the native salt water compounds found in and around human cells. The beverage can be fine tuned to mimic or mirror molecular compositions of different biological media. The life enhancing beverage can have reactive species other than chlorine present. As described, species present in the compositions and beverages described herein can include, but are not limited to O2, H2, Cl2, OCl−, HOCl, NaOCl, HClO2, ClO2, HClO3, HClO4, H2O2, Na+, Cl−, H+, H−, OH−, O3, O4*−, 1O, OH*−, HOCl—O2*−, HOCl—O3, O2*, HO2*, NaCl, HCl, NaOH, and water clusters: n*H2O-induced dipolar layers around ions, several variations.

Depending on the parameters used to produce the beverage, different components can be present at different concentrations. In one embodiment, the beverage can include about 0.1 ppt, about 0.5 ppt, about 1 ppt, about 1.5 ppt, about 2 ppt, about 2.5 ppt, about 3 ppt, about 3.5 ppt, about 4 ppt, about 4.5 ppt, about 5 ppt, about 6 ppt, about 7 ppt, about 8 ppt, about 9 ppt, about 10 ppt, about 20 ppt, about 50 ppt, about 100 ppt, about 200 ppt, about 400 ppt, about 1,000 ppt, between about 0.1 ppt and about 1,000 ppt, between about 0.1 ppt and about 100 ppt, between about 0.1 ppt and about 10 ppt, between about 2 ppt and about 4 ppt, at least about 0.1 ppt, at least about 2 ppt, at least about 3 ppt, at most about 10 ppt, or at most about 100 ppt of OCl−. In some embodiments, OCl− can be present at about 3 ppt. In other embodiments, OCl− can be the predominant chlorine containing species in the beverage.

In some embodiments, hydroxyl radicals can be stabilized in the beverage by the formation of radical complexes. The radical complexes can be held together by hydrogen bonding. Another radical that can be present in the beverage is an OOH* radical. Still other radical complexes can include a nitroxyl-peroxide radical (HNO—HOO*) and/or a hypochlorite-peroxide radical (HOCl—HOO*).

Reactive species' concentrations in the life enhancing solutions, detected by fluorescence photo spectroscopy, may not significantly decrease in time. Mathematical models show that bound HOCl—*O2− complexes are possible at room temperature. Molecular complexes can preserve volatile components of reactive species. For example, reactive species concentrations in whole blood as a result of molecular complexes may prevent reactive species degradation over time.

Reactive species can be further divided into "reduced species" (RS) and "reactive oxygen species" (ROS). Reactive species can be formed from water molecules and sodium chloride ions when restructured through a process of forced electron donation. Electrons from lower molecular energy configurations in the salinated water may be forced into higher, more reactive molecular configurations. The species from which the electron was taken can be "electron hungry" and is called the RS and can readily become an electron acceptor (or proton donor) under the right conditions. The species that obtains the high-energy electron can be an electron donor and is called the ROS and may energetically release these electrons under the right conditions.

When an energetic electron in ROS is unpaired it is called a "radical". ROS and RS can recombine to neutralize each other by the use of a catalytic enzyme. Three elements, (1) enzymes, (2) electron acceptors, and (3) electron donors can all be present at the same time and location for neutralization to occur.

In some embodiments, substantially no organic material is present in the beverages described. Substantially no organic material can be less than about 0.1 ppt, less than about 0.01 ppt, less than about 0.001 ppt or less than about 0.0001 ppt of total organic material.

The life enhancing beverage can be stored and bottled as needed to ship to consumers. The life enhancing beverage can have a shelf life of about 5 days, about 30 days, about 3 months, about 6 months, about 9 months, about 1 year, about 1.5 years, about 2 years, about 3 years, about 5 years, about 10 years, at least about 5 days, at least about 30 days, at least about 3 months, at least about 6 months, at least about 9 months, at least about 1 year, at least about 1.5 years, at least about 2 years, at least about 3 years, at least about 5 years, at least about 10 years, between about 5 days and about 1 year, between about 5 days and about 2 years, between about 1 year and about 5 years, between about 90 days and about 3 years, between about 90 days and about 5 year, or between about 1 year and about 3 years.

Quality Assurance testing can be done on every batch before the batch can be approved for bottling or can be performed during or after bottling. A 16 oz. sample bottle can be taken from each complete batch and analyzed. Determinations for presence of contaminants such as heavy metals or chlorates can be performed. Then pH, Free and Total Chlorine concentrations and reactive molecule concentrations of the active ingredients can be analyzed by fluorospectroscopy methods. These results can be compared to those of a standard solution which is also tested along side every sample. If the results for the batch fall within a certain range relative to the standard solution, it can be approved. A chemical chromospectroscopic MS analysis can also be run on random samples to determine if contaminants from the production process are present.

The beverage can be consumed by ingestion. In other embodiments, the beverage can be provided as a solution for injection. In some embodiments, injection can be subcutaneous, intra-luminal, site specific (e.g., injected into a cancer or internal lesion), or intramuscular. Intravenous injection can also be desirable. The life enhancing solution can be packaged in plastic medical solution pouches having volumes of about 4 oz, about 8 oz, about 16 oz, about 32 oz, about 48 oz, about 64 oz, about 80 oz, about 96 oz, about 112 oz, about 128 oz, about 144 oz, about 160 oz, or any range created using any of these values, and these pouches can be used with common intravenous administration systems.

Flavors can be added to the life enhancing beverages. Flavor additives introduced into the life enhancing beverages may not substantially degrade any of the beneficial components of the beverage. In one embodiment, a flavor does not substantially degrade more than about 5%, more than about 4%, more than about 3%, more than about 2%, more than about 1%, more than about 0.5%, more than about 0.1%, more than about 0.05%, more than about 0.01%, more than about 0.005%, more than about 0.001%, more than about 0.0005%, or more than about 0.0001% of the life enhancing beverage. Flavors can include chocolate, fruit flavors, coffee flavor, mint, and the like.

When administered as a liquid beverage, it can be taken once, twice, three times, four times or more a day. Each administration can be about 1 oz, about 2 oz, about 3 oz, about 4 oz, about 5 oz, about 6 oz, about 7 oz, about 8 oz, about 9 oz, about 10 oz, about 11 oz, about 12 oz, about 16 oz, about 20 oz, about 24 oz, about 28 oz, about 32 oz, about 34 oz, about 36 oz, about 38 oz, about 40 oz, about 46 oz, between about 1 oz and about 32 oz, between about 1 oz and about 16 oz, between about 1 oz and about 8 oz, at least about 2 oz, at least about 4 oz, or at least about 8 oz. In one embodiment, the beverage can be administered at a rate of about 4 oz twice a day.

In other embodiments, the administration can be acute or long term. For example, the beverage can be consumed for a day, a week, a month, a year or longer. In other embodiments, the beverage can simply be taken as needed such as for exercise.

The beverages described herein when administered can be used to treat a condition or a disease or can enhance a life condition or a condition associated with a disease. For example, when administered alongside exercise, the beverages described herein can increase the density of mitochondrial DNA. For example, an increase in mitochondrial DNA of about 1%, about 5%, about 10%, about 15%, about 20%, about 21%, about 22%, about 23%, about 24%, about 25%, about 26%, about 27%, about 28%, about 29%, about 30%, about 32%, about 34%, about 36%, about 38%, about 40%, about 45%, between about 1% and about 40%, between about 1% and about 10%, between about 20% and about 30%, at least about 5%, at least about 10%, or at least about 20% when compared to an individual who has not taken the beverage. An increase in mitochondrial DNA can result in a lower level of free radicals in the blood which can in turn lead to a reduced amount of oxidative stress.

A direct current, DC, power source is used to electrolyze water.

The variables of voltage, amps, frequency, time and current required depend on the compound and/or ion themselves and their respective bond strengths. To that end, the variables of voltage, amps, frequency, time and current are compound and/or ion dependent and are not limiting factors. That notwithstanding, the voltage used can be less than 40V, such as 30V or 20V or 10V or any voltage in between. The voltage can also modulate and at any time vary within a range of from 1 to 40V or from 10 to 30V or from 20 to 30V. These ranges are non-limiting but are shown as examples.

Waveforms with an AC ripple also referred to as pulse or spiking waveforms include: any positive pulsing currents such as pulsed waves, pulse train, square wave, sawtooth wave, spiked waveforms, pulse-width modulation (PWM), pulse duration modulation (PDM), single phase half wave rectified AC, single phase full wave rectified AC or three phase full wave rectified for example.

A bridge rectifier may be used. Other types of rectifiers can be used such as Single-phase rectifiers, Full-wave rectifiers, Three-phase rectifiers, Twelve-pulse bridge, Voltage-multiplying rectifiers, filter rectifier, a silicon rectifier, an SCR type rectifier, a high-frequency (RF) rectifier, an inverter digital-controller rectifier, vacuum tube diodes, mercury-arc valves, solid-state diodes, silicon-controlled rectifiers and the like. Pulsed waveforms can be made with a transistor regulated power supply, a dropper type power supply, a switching power supply and the like.

A transformer may be used. Examples of transformers that can be used include center tapped transformers, Auto-transformer, Capacitor voltage transformer, Distribution transformer, power transformer, Phase angle regulating transformer, Scott-T transformer, Polyphase transformer, Grounding transformer, Leakage transformer, Resonant transformer, Audio transformer, Output transformer, Laminated core Toroidal Autotransformer, Variable autotransformer, Induction regulator, Stray field transformer, Polyphase transformer, Grounding transformer, Leakage transformers, Resonant transformer, Constant voltage transformer, Ferrite core Planar transformer Oil cooled transformer, Cast resin transformer, Isolating transformer, Instrument transformer, Current transformer, Potential transformer Pulse transformer transformer Air-core transformer, Ferrite-core transformer, Transmission-line transformer, Balun Audio transformer, Loudspeaker transformer, Output transformer, Small signal transformer, Interstage coupling transformers, Hedgehog or Variocoupler.

Compositions of the invention can be formulated into any suitable aspect, such as, for example, aerosols, liquids, elixirs, syrups, tinctures and the like.

When administered as a liquid composition, it can be taken once, twice, three times, four times or more a day. Each administration can be about 1 oz, about 2 oz, about 3 oz, about 4 oz, about 5 oz, about 6 oz, about 7 oz, about 8 oz, about 9 oz, about 10 oz, about 11 oz, about 12 oz, about 16 oz, about 20 oz, about 24 oz, about 28 oz, about 32 oz, about 34 oz, about 36 oz, about 38 oz, about 40 oz, about 46 oz, between about 1 oz and about 32 oz, between about 1 oz and about 16 oz, between about 1 oz and about 8 oz, at least about 2 oz, at least about 4 oz, or at least about 8 oz. In one embodiment, the composition can be administered at a rate of about 4 oz twice a day.

In other embodiments, the administration can be acute or long term. For example, the composition can be administered for a day, a week, a month, a year or longer.

In other embodiments, methods of treating oxidative are described comprising: administering a composition including at least one species selected from $O_2$, $H_2$, $Cl_2$, $OCl^-$, $HOCl$, $NaOCl$, $HClO_2$, $ClO_2$, $HClO_3$, $HClO_4$, $H_2O_2$, $Na^+$, $Cl^-$, $H^+$, $H^-$, $OH^-$, $O_3$, $O_4^{*-}$, $^1O$, $OH^{*-}$, $HOCl$—$O_2^{*-}$, $HOCl$—$O_3$, $O_2^{*-}$, $HO_2^*$, $NaCl$, $HCl$, $NaOH$, water clusters, or a combination thereof to a subject experiencing oxidative stress. In some embodiments, the administration occurs twice a day or once a day. Each administration can include between about 1 oz to about 16 oz per day.

Example 1

Figure 3:
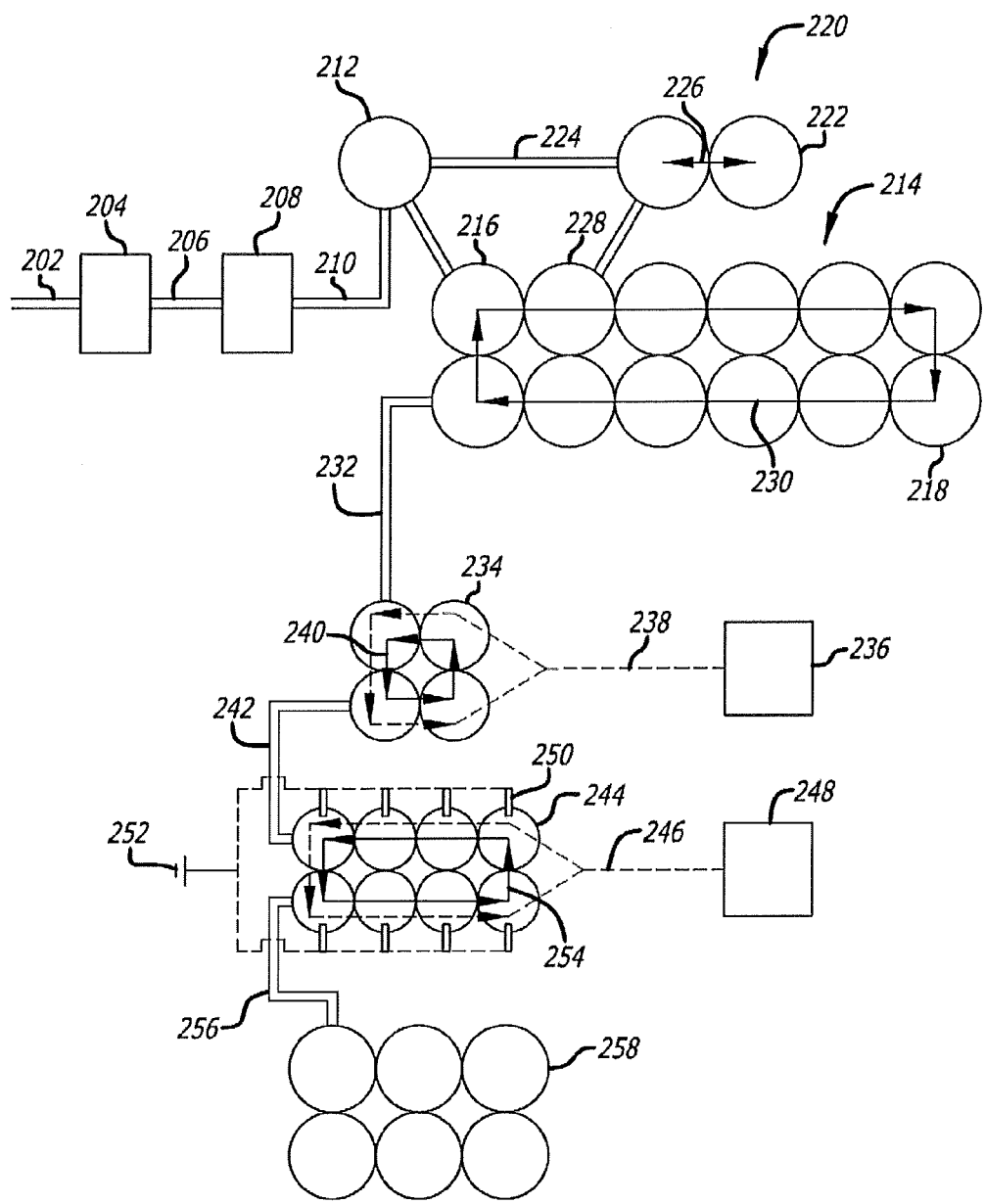
FIG. 3 illustrates a plan view of a process and system for producing a composition according to the present description.

FIG. 3 illustrates a plan view of a process and system for producing a life enhancing composition according to the present description. One skilled in the art understands that changes can be made to the system to alter the life enhancing composition, and these changes are within the scope of the present description.

Incoming water 202 can be subjected to reverse osmosis system 204 at a temperature of about 15-20° C. to achieve purified water 206 with about 8 ppm of total dissolved solids. Purified water 206, is then fed at a temperature of about 15-20° C. into distiller 208 and processed to achieve distilled water 210 with about 0.5 ppm of total dissolved solids. Distilled water 210 can then be stored in tank 212.

Figure 4:
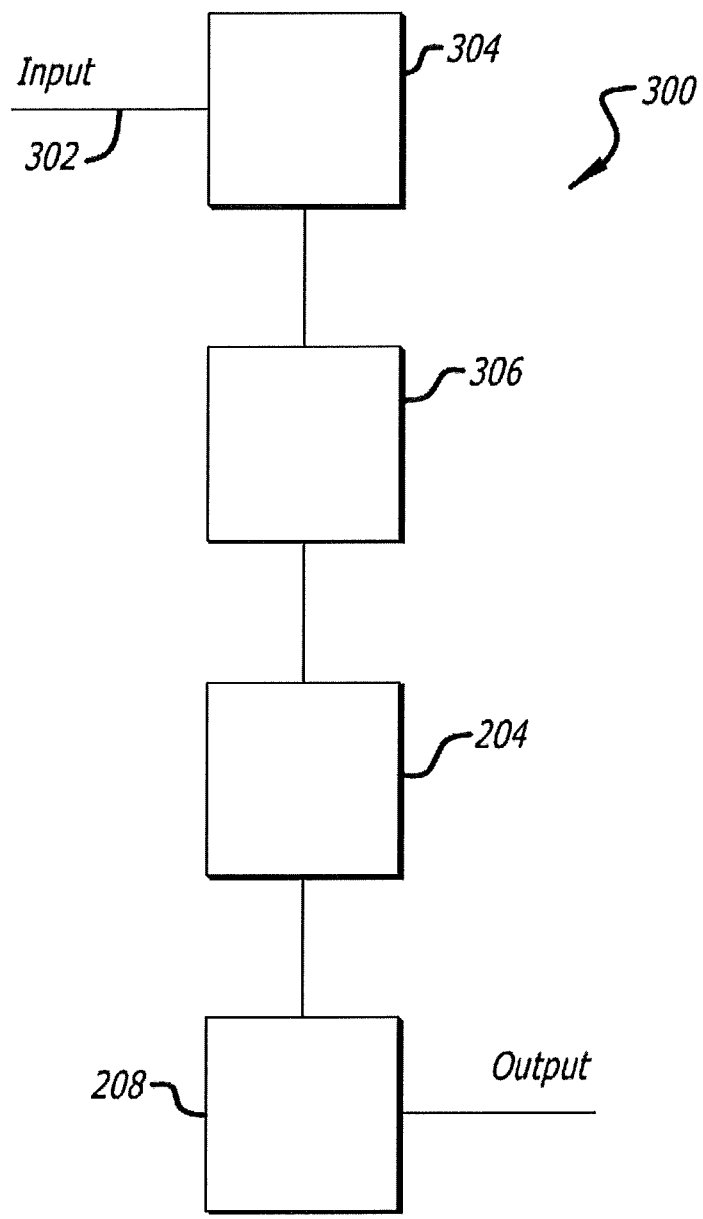
FIG. 4 illustrates an example system for preparing water for further processing into a composition described herein.

FIG. 4 illustrates an example system for preparing water for further processing into a therapeutic beverage. System 300 can include a water source 302 which can feed directly into a carbon filter 304. After oils, alcohols, and other volatile chemical residuals and particulates are removed by carbon filter 304, the water can be directed to resin beds within a water softener 306 which can remove dissolved minerals. Then, as described above, the water can pass through reverse osmosis system 204 and distiller 208.

Referring again to FIG. 3, distilled water 210 can be gravity fed as needed from tank 212 into saline storage tank cluster 214 using line 216. Saline storage tank cluster 214 in one embodiment can include twelve tanks 218. Each tank 218 can be filled to about 1,300 gallons with distilled water 210. A handheld meter can be used to test distilled water 210 for salinity.

Saline storage tank cluster 214 is then salted using a brine system 220. Brine system 220 can include two brine tanks 222. Each tank can have a capacity of about 500 gallons. Brine tanks 222 are filled to 475 gallons with distilled water 210 using line 224 and then NaCl is added to the brine tanks 222 at a ratio of about 537.5 g/gal of liquid. At this point, the water is circulated 226 in the brine tanks 222 at a rate of about 2,000 gal/hr for about 4 days.

Prior to addition of brine to tanks 218, the salinity of the water in tanks 218 can be tested using a handheld conductivity meter such as an YSI ECOSENSE® ecp300 (YSI Inc., Yellow Springs, Ohio). Any corrections based on the salinity measurements can be made at this point. Brine solution 228 is then added to tanks 218 to achieve a salt concentration of about 10.75 g/gal. The salted water is circulated 230 in tanks 218 at a rate of about 2,000 gal/hr for no less than about 72 hours. This circulation is performed at room temperature. A handheld probe can again be used to test salinity of the salinated solution. In one embodiment, the salinity is about 2.8 ppth.

In one method for filling and mixing the salt water in the brine holding tanks, the amount of liquid remaining in the tanks is measured. The amount of liquid remaining in a tank is measured by recording the height that the liquid level is from the floor that sustains the tank, in centimeters, and referencing the number of gallons this height represents. This can be done from the outside of the tank if the tank is semi-transparent. The initial liquid height in both tied tanks can also be measured. Then, after ensuring that the output valve is closed, distilled water can be pumped in. The amount of distilled water that is being pumped into a holding tank can then be calculated by measuring the rise in liquid level: subtracting the initial height from the filled height and then multiplying this difference by a known factor.

The amount of salt to be added to the tank is then calculated by multiplying 11 grams of salt for every gallon of distilled water that has been added to the tank. The salt can be carefully weighed out and dumped into the tank.

The tank is then agitated by turning on the recirculation pump and then opening the top and bottom valves on the tank. Liquid is pumped from the bottom of the tank to the top. The tank can be agitated for three days before it may be ready to be processed.

After agitating the tank for more than 6 hours, the salinity is checked with a salinity meter by taking a sample from the tank and testing it. Salt or water can be added to adjust the salinity within the tanks. If either more water or more salt is added then the tanks are agitated for 6 more hours and tested again. After about three days of agitation, the tank is ready to be processed.

Salinated water 232 is then transferred to cold saline tanks 234. In one embodiment, four 250 gal tanks are used. The amount of salinated water 232 moved is about 1,000 gal. A chiller 236 such as a 16 ton chiller is used to cool heat exchangers 238 to about 0-5° C. The salinated water is circulated 240 through the heat exchangers which are circulated with propylene glycol until the temperature of the salinated water is about 4.5-5.8° C. Chilling the 1,000 gal of salinated water generally takes about 6-8 hr.

Cold salinated water 242 is then transferred to processing tanks 244. In one embodiment, eight tanks are used and each can have a capacity of about 180 gal. Each processing tank 244 is filled to about 125 gal for a total of 1,000 gal. Heat exchangers 246 are again used to chill the cold salinated water 242 added to processing tanks 244. Each processing tank can include a cylinder of chilling tubes and propylene glycol can be circulated. The heat exchangers can be powered by a 4-5 ton chiller 248. The temperature of cold salinated water 242 can remain at 4.5-5.8° C. during processing.

Prior to transferring aged salt water to processing tanks, the aged salt water can be agitated for about 30 minutes to sufficiently mix the aged salt water. Then, the recirculation valves can then be closed, the appropriate inlet valve on the production tank is opened, and the tank filled so that the salt water covers the cooling coils and comes up to the fill mark (approximately 125 gallons).

Once the aged salt water has reached production temperature, the pump is turned off but the chiller left on. The tank should be adequately agitated or re-circulated during the whole duration of electrochemical processing and the temperature should remain constant throughout.

Each processing tank 244 includes electrode 250. Electrodes 250 can be 3 inches tall circular structures formed of titanium and plated with platinum. Electrochemical processing of the cold salinated water can be run for 8 hr. A power supply 252 is used to power the eight electrodes (one in each processing tank 244) to 7 amps each for a total of 56 amps. The cold salinated water is circulated 254 during electrochemical processing at a rate of about 1,000 gal/hr.

An independent current meter can be used to set the current to around 7.0 Amps. Attention can be paid to ensure that the voltage does not exceed 12V and does not go lower than 9V. Normal operation can be about 10V.

A run timer can be set for a prescribed time (about 4.5 to 5 hours). Each production tank can have its own timer and/or power supply. Electrodes should be turned off after the timer has expired.

The production tanks can be checked periodically. The temperature and/or electrical current can be kept substantially constant. At the beginning, the electrodes can be visible from the top, emitting visible bubbles. After about 3 hours, small bubbles of un-dissolved oxygen can start building up in the tank as oxygen saturation occurs, obscuring the view of the electrodes. A slight chlorine smell can be normal.

After the 8 hour electrochemical processing is complete, life enhancing water 256 has been created with a pH of about 6.8-8.2, 32 ppm of chlorine, 100% OCl⁻ and 100% $O^{-2}$ of a known standard for measuring OCl⁻ and 100% $O^{-2}$ as described herein. The composition 256 is transferred to storage tanks 258.

Example 2

Characterization of a Beverage Produced as Described in Example 1

A composition produced as described in Example 1 and marketed under the trade name ASEA® was analyzed using a variety of different characterization techniques. ICP/MS and $^{35}$Cl NMR were used to analyze and quantify chlorine content. Headspace mass spectrometry analysis was used to analyze adsorbed gas content in the beverage. $^1$H NMR was used to verify the organic matter content in the beverage. $^{31}$P NMR and EPR experiments utilizing spin trap molecules were used to explore the beverage for free radicals.

The composition was received and stored at about 4° C. when not being used.

Chlorine NMR

Sodium hypochlorite solutions were prepared at different pH values. 5% sodium hypochlorite solution had a pH of 12.48. Concentrated nitric acid was added to 5% sodium hypochlorite solution to create solutions that were at pH of 9.99, 6.99, 5.32, and 3.28. These solutions were then analyzed by NMR spectroscopy. The beverage had a measured pH of 8.01 and was analyzed directly by NMR with no dilutions.

NMR spectroscopy experiments were performed using a 400 MHz Bruker spectrometer equipped with a BBO probe. $^{35}$Cl NMR experiments were performed at a frequency of 39.2 MHz using single pulse experiments. A recycle delay of 10 seconds was used, and 128 scans were acquired per sample. A solution of NaCl in water was used as an external chemical shift reference. All experiments were performed at room temperature.

Figure 5:
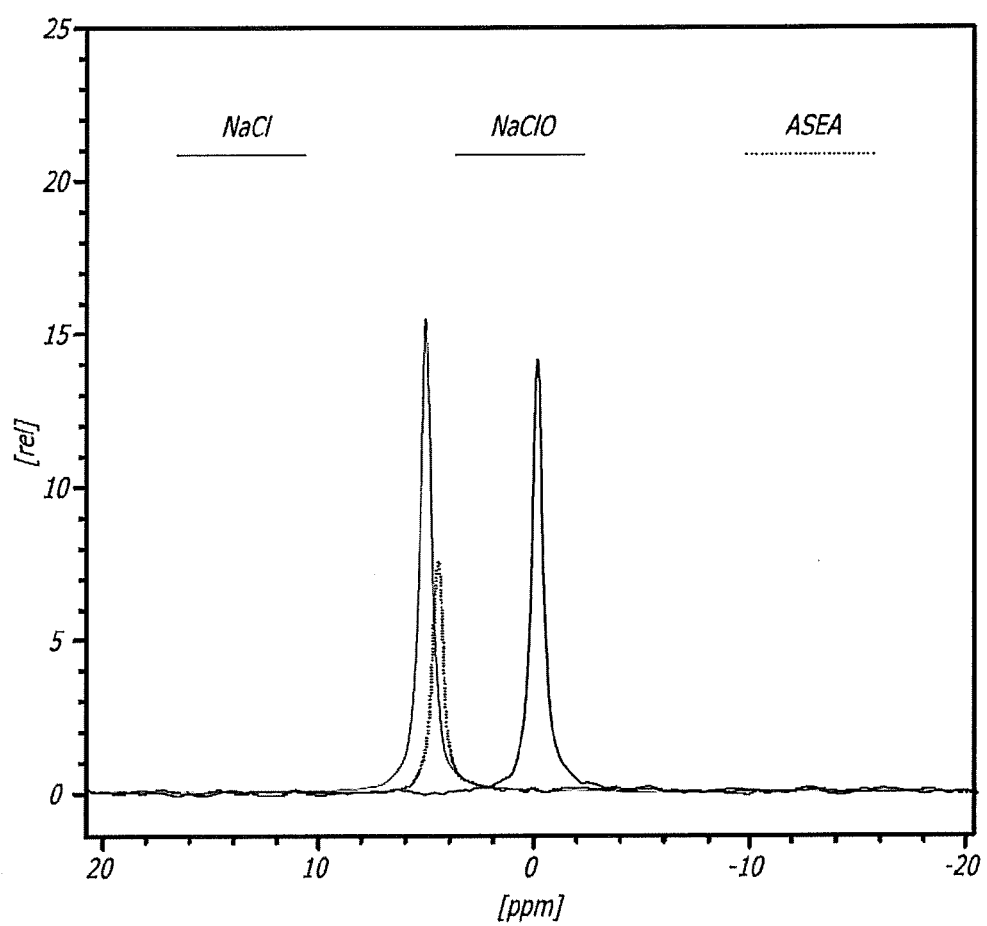
FIG. 5 illustrates a Cl35 spectrum of NaCl, NaClO solution at a pH of 12.48, and a composition described herein (the composition is labeled "ASEA").

$^{35}$Cl NMR spectra were collected for NaCl solution, NaClO solutions adjusted to different pH values, and the composition. FIG. 5 illustrates a Cl135 spectrum of NaCl, NaClO solution at a pH of 12.48, and the composition. The chemical shift scale was referenced by setting the Cl⁻ peak to 0 ppm. NaClO solutions above a pH=7 had identical spectra with a peak at approximately 5.1 ppm. Below pH of 7.0, the ClO⁻ peak disappeared and was replaced by much broader, less easily identifiable peaks. The composition was presented with one peak at approximately 4.7 ppm, from ClO⁻ in the composition. This peak was integrated to estimate the concentration of ClO⁻ in the composition, which was determined to be 2.99 ppt or 0.17 M of ClO⁻ in the composition.

Proton NMR

An ASEA sample was prepared by adding 550 μL of ASEA and 50 μL of $D_2O$ (Cambridge Isotope Laboratories) to an NMR tube and vortexing the sample for 10 seconds. $^1$H NMR experiments were performed on a 700 MHz Bruker spectrometer equipped with a QNP cryogenically cooled probe. Experiments used a single pulse with pre-saturation on the water resonance experiment. A total of 1024 scans were taken. All experiments were performed at room temperature.

Figure 6:
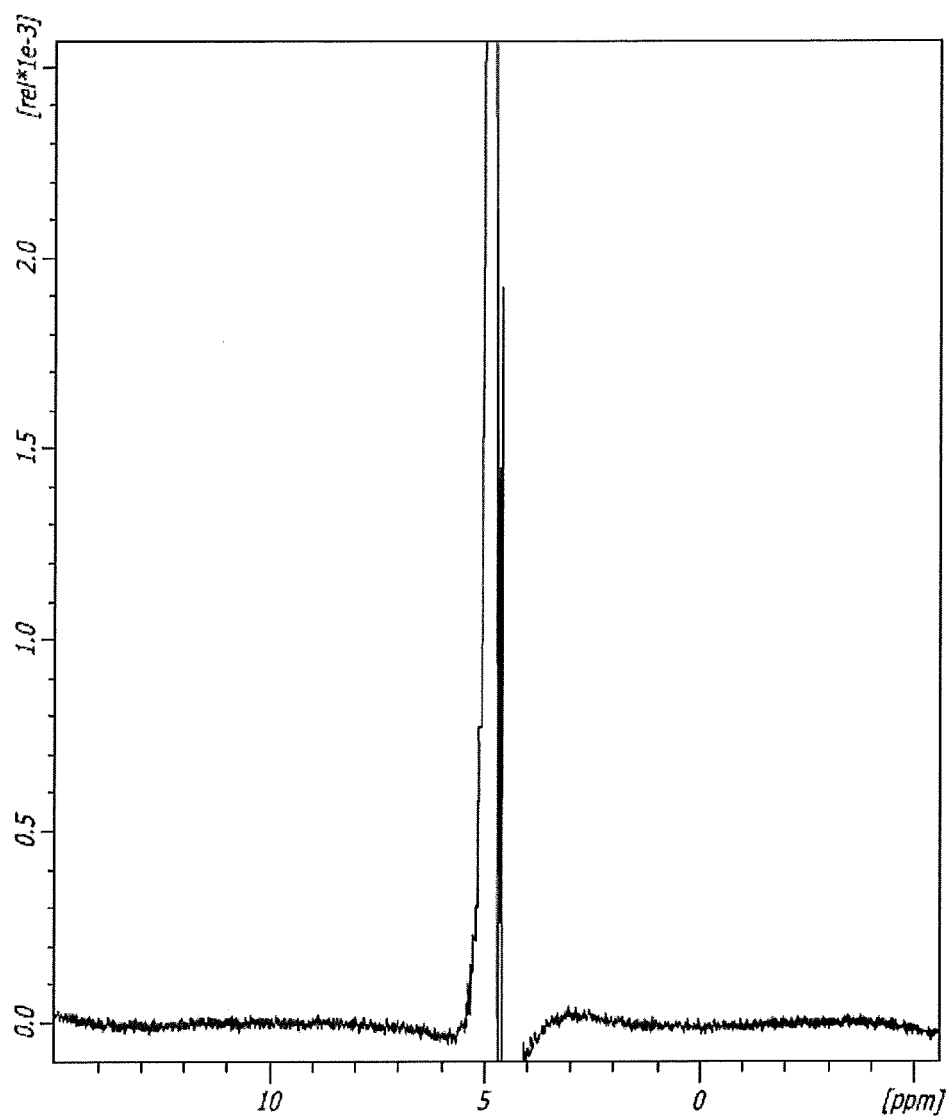
FIG. 6 illustrates a $^1H$ NMR spectrum of a composition of the present disclosure.

A $^1$H NMR spectrum of the composition was determined and is presented in FIG. 6. Only peaks associated with water were able to be distinguished from this spectrum. This spectrum show that very little if any organic material can be detected in the composition using this method.

Phosphorous NMR and Mass Spectrometry

DIPPMPO (5-(Diisopropoxyphosphoryl)-5-1-pyrroline-N-oxide) (VWR) samples were prepared by measuring about 5 mg of DIPPMPO into a 2 mL centrifuge tube. This tube then had 550 μL of either the composition or water added to it, followed by 50 μL of $D_2O$. A solution was also prepared with the composition but without DIPPMPO. These solutions were vortexed and transferred to NMR tubes for analysis. Samples for mass spectrometry analysis were prepared by dissolving about 5 mg of DIPPMPO in 600 μL of the composition and vortexing, then diluting the sample by adding 100 μL of sample and 900 μL of water to a vial and vortexing.

NMR experiments were performed using a 700 MHz Bruker spectrometer equipped with a QNP cryogenically cooled probe. Experiments performed were a single 30° pulse at a $^{31}P$ frequency of 283.4 MHz. A recycle delay of 2.5 seconds and 16384 scans were used. Phosphoric acid was used as an external standard. All experiments were performed at room temperature.

Mass spectrometry experiments were performed by directly injecting the ASEA/DIPPMPO sample into a Waters/Synapt Time of Flight mass spectrometer. The sample was directly injected into the mass spectrometer, bypassing the LC, and monitored in both positive and negative ion mode.

Figure 7:
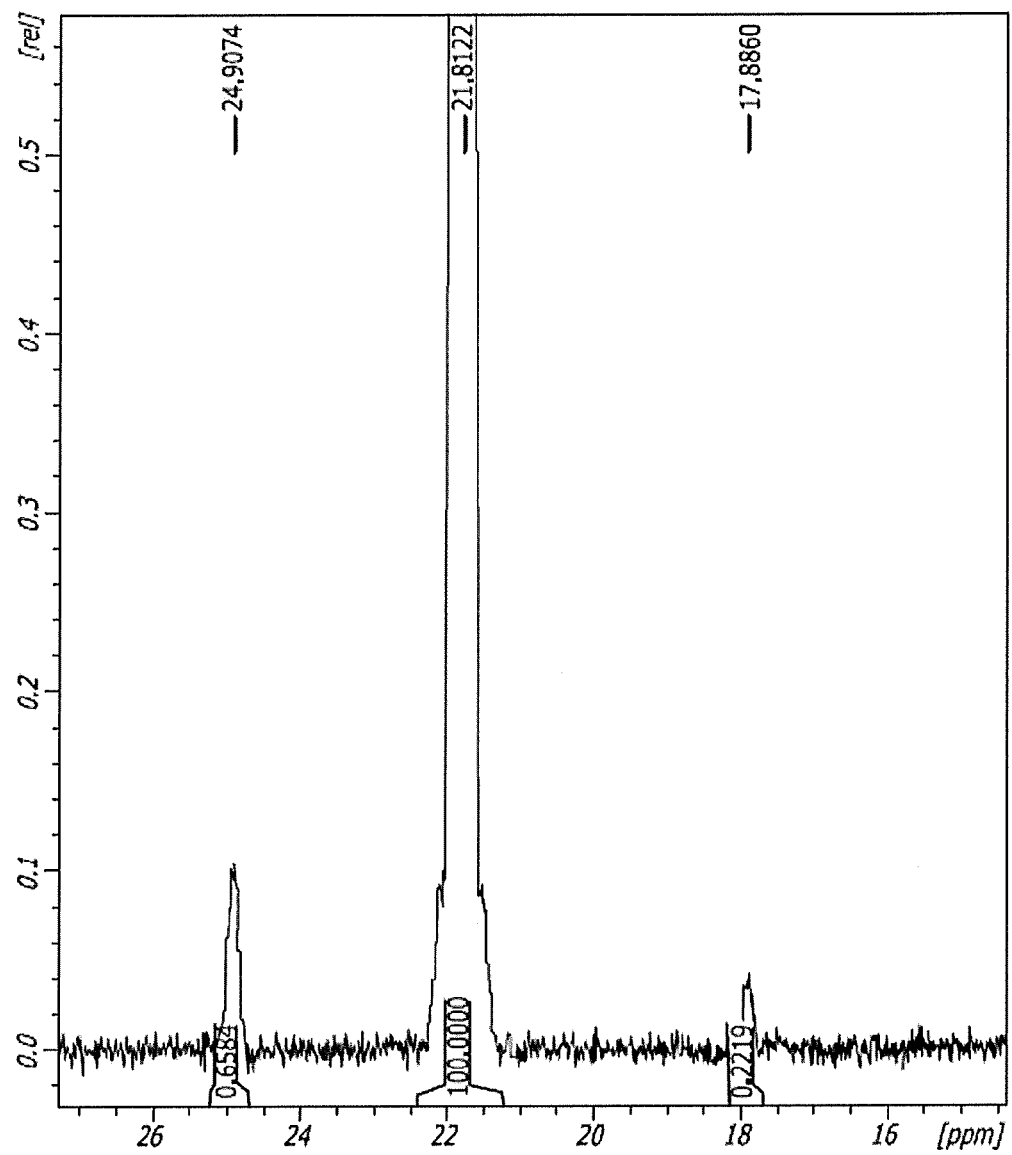
FIG. 7 illustrates a 31P NMR spectrum of DIPPMPO combined with a composition described herein.

$^{31}P$ NMR spectra were collected for DIPPMPO in water, the composition alone, and the composition with DIPPMPO added to it. An external reference of phosphoric acid was used as a chemical shift reference. FIG. 7 illustrates a $^{31}P$ NMR spectrum of DIPPMPO combined with the composition. The peak at 21.8 ppm was determined to be DIPPMPO and is seen in both the spectrum of DIPPMPO with the composition (FIG. 7) and without the composition (not pictured). The peak at 24.9 ppm is most probably DIPPMPO/OH. as determined in other DIPPMPO studies. This peak may be seen in DIPPMPO mixtures both with and without the composition, but is detected at a much greater concentration in the solution with the composition. In the DIPPMPO mixture with the composition, there is another peak at 17.9 ppm. This peak may be from another radical species in the composition such as OOH. or possibly a different radical complex. The approximate concentrations of spin trap complexes in the composition/DIPPMPO solution are as follows:

| Solution | Concentration |
| --- | --- |
| DIPPMPO | 36.6 mM |
| DIPPMPO/OH• | 241 μM |
| DIPPMPO/radical | 94 μM |

Figure 8:
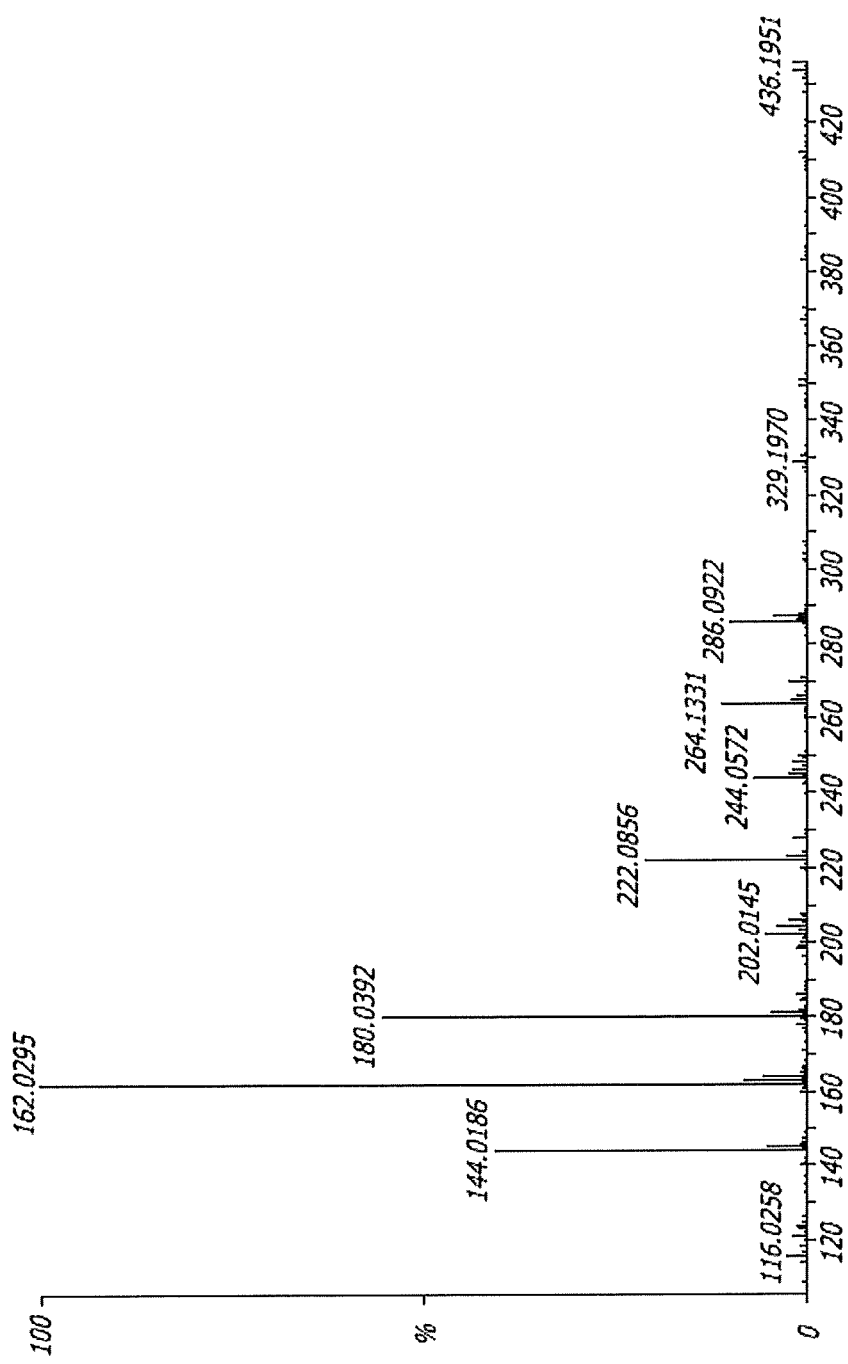
FIG. 8 illustrates a mass spectrum showing a parent peak and fragmentation pattern for DIPPMPO with m/z peaks at 264, 222, and 180.

Mass spectral data was collected in an attempt to determine the composition of the unidentified radical species. The mass spectrum shows a parent peak and fragmentation pattern for DIPPMPO with m/z peaks at 264, 222, and 180, as seen in FIG. 8. FIG. 8 also shows peaks for the DIPPMPO/Na adduct and subsequent fragments at 286, 244, and 202 m/z. Finally, FIG. 8 demonstrates peaks for one DIPPMPO/radical complex with m/z of 329. The negative ion mode mass spectrum also had a corresponding peak at m/z of 327. There are additional peaks at 349, 367, and 302 at a lower intensity as presented in FIG. 8. None of these peaks could be positively confirmed. However, there are possible structures that would result in these mass patterns. One possibility for the peak generated at 329 could be a structure formed from a radical combining with DIPPMPO. Possibilities of this radical species include a nitroxyl-peroxide radical (HNO—HOO.) that may have formed in the beverage as a result of reaction with nitrogen from the air. Another peak at 349 could also be a result of a DIPPMPO/radical combination. Here, a possibility for the radical may be hypochlorite-peroxide (HOCl⁻HOO.). However, the small intensity of this peak and small intensity of the corresponding peak of 347 in the negative ion mode mass spectrum indicate this could be a very low concentration impurity and not a compound present in the ASEA composition.

ICP/MS Analysis

Samples were analyzed on an Agilent 7500 series inductively-coupled plasma mass spectrometer (ICP-MS) in order to confirm the hypochlorite concentration that was determined by NMR. A stock solution of 5% sodium hypochlorite was used to prepare a series of dilutions consisting of 300 ppb, 150 ppb, 75 ppb, 37.5 ppb, 18.75 ppb, 9.375 ppb, 4.6875 ppb, 2.34375 ppb, and 1.171875 ppb in deionized Milli-Q water. These standards were used to establish a standard curve.

Based on NMR hypochlorite concentration data, a series of dilutions was prepared consisting of 164.9835 ppb, 82.49175 ppb, 41.245875 ppb, 20.622937 ppb, 10.311468 ppb, and 5.155734 ppb. These theoretical values were then compared with the values determined by ICP-MS analysis. The instrument parameters were as follows:

| Elements analyzed | $^{35}Cl$, $^{37}Cl$ |
| --- | --- |
| # of points per mass | 20 |
| # of repetitions | 5 |
| Total acquisition time | 68.8 s |
| Uptake speed | 0.50 rps |
| Uptake time | 33 s |
| Stabilization time | 40 s |
| Tune | No Gas |
| Nebulizer flow rate | 1 mL/min |
| Torch power | 1500 W |

The results of the ICP-MS analysis are as follows:

| Dilution | Measured Concentration (ppb) | Concentration by NMR (ppb) |
| --- | --- | --- |
| 1 | 81 | 82 |
| 2 | 28 | 41 |
| 3 | 24 | 21 |
| 4 | 13 | 10 |
| 5 | 8 | 5 |

Dilutions were compared graphically to the ICP-MS signals and fit to a linear equation ($R^2$=0.9522). Assuming linear behavior of the ICP-MS signal, the concentration of hypochlorite in the beverage was measured to be 3.02 ppt. Concentration values were determined by calculating the concentration of dilutions of the initial beverage and estimating the initial beverage hypochlorite concentration to be 3 ppt (as determined from $^{35}Cl$ NMR analysis). The ICP-MS data correlate well with the $^{35}Cl$ NMR data, confirming a hypochlorite concentration of roughly ⅓% (3 ppt). It should be noted that ICP-MS analysis is capable of measuring total chlorine atom concentration in solution, but not specific chlorine species. The NMR data indicate that chlorine predominantly exists as $ClO^-$ in the beverage.

Gas Phase Quadrupole MS
Sample Prep

Three sample groups were prepared in triplicate for the analysis: 1) Milli-Q deionized water 2) the composition, and 3) 5% sodium hypochlorite standard solution. The vials used were 20 mL headspace vials with magnetic crimp caps (GERSTEL). A small stir bar was placed in each vial (VWR) along with 10 mL of sample. The vials were capped, and then placed in a Branson model 5510 sonicator for one hour at 60° C.

The sonicator was set to degas which allowed for any dissolved gasses to be released from the sample into the headspace. After degassing, the samples were placed on a CTC PAL autosampler equipped with a heated agitator and headspace syringe. The agitator was set to 750 rpm and 95° C. and the syringe was set to 75° C. Each vial was placed in the agitator for 20 min prior to injection into the instrument. A headspace volume of 2.5 mL was collected from the vial and injected into the instrument.

Instrument Parameters

The instrument used was an Agilent 7890A GC system coupled to an Agilent 5975C EI/CI single quadrupole mass selective detector (MSD) set up for electron ionization. The GC oven was set to 40° C. with the front inlet and the transfer lines being set to 150° C. and 155° C. respectively. The carrier gas used was helium and it was set to a pressure of 15 PSI.

The MSD was set to single ion mode (SIM) in order to detect the following analytes:

| Analyte | Mass |
| --- | --- |
| Water | 18 |
| Nitrogen | 28 |
| Oxygen | 32 |
| Argon | 40 |
| Carbon Dioxide | 44 |
| Chlorine | 70 |
| Ozone | 48 |

The ionization source temperature was set to 230° C. and the quadrupole temperature was set to 150° C. The electron energy was set to 15 V.

Mass spectrometry data was obtained from analysis of the gas phase headspace of the water, the composition, and hypochlorite solution. The raw area counts obtained from the mass spectrometer were normalized to the area counts of nitrogen in order to eliminate any systematic instrument variation. Both nitrogen and water were used as standards because they were present in equal volumes in the vial with nitrogen occupying the headspace and water being the solvent. It was assumed that the overall volume of water and nitrogen would be the same for each sample after degassing. In order for this assumption to be correct, the ratio of nitrogen to water should be the same for each sample. A cutoff value for the percent relative standard deviation (% RSD) of 5% was used. Across all nine samples, a % RSD of 4.2 was observed. Of note, sample $NaClO^{-3}$ appears to be an outlier, thus, when removed, the % RSD drops to 3.4%.

FIGS. 9-11 illustrate oxygen/nitrogen, chlorine/nitrogen, and ozone/nitrogen ratios. It appears that there were less of these gases released from the composition than from either water or nitrogen. It should be noted that the signals for both ozone and chlorine were very weak. Thus, there is a possibility that these signals may be due to instrument noise and not from the target analytes.

FIG. 12 illustrates the carbon dioxide to nitrogen ratio. It appears that there may have been more carbon dioxide released from the composition than oxygen. However, it is possible that this may be due to background contamination from the atmosphere.

Based on the above, more oxygen was released from both water and sodium hypochlorite than the composition.

EPR

Two different composition samples were prepared for EPR analysis. The composition with nothing added was one sample. The other sample was prepared by adding 31 mg of DIPPMPO to 20 mL of the composition (5.9 mM), vortexing, and placing the sample in a 4° C. refrigerator overnight. Both samples were placed in a small capillary tube which was then inserted into a normal 5 mm EPR tube for analysis.

EPR experiments were performed on a Bruker EMX 10/12 EPR spectrometer. EPR experiments were performed at 9.8 GHz with a centerfield position of 3500 Gauss and a sweepwidth of 100 Gauss. A 20 mW energy pulse was used with modulation frequency of 100 kHz and modulation amplitude of 1G. Experiments used 100 scans. All experiments were performed at room temperature.

Figure 13:
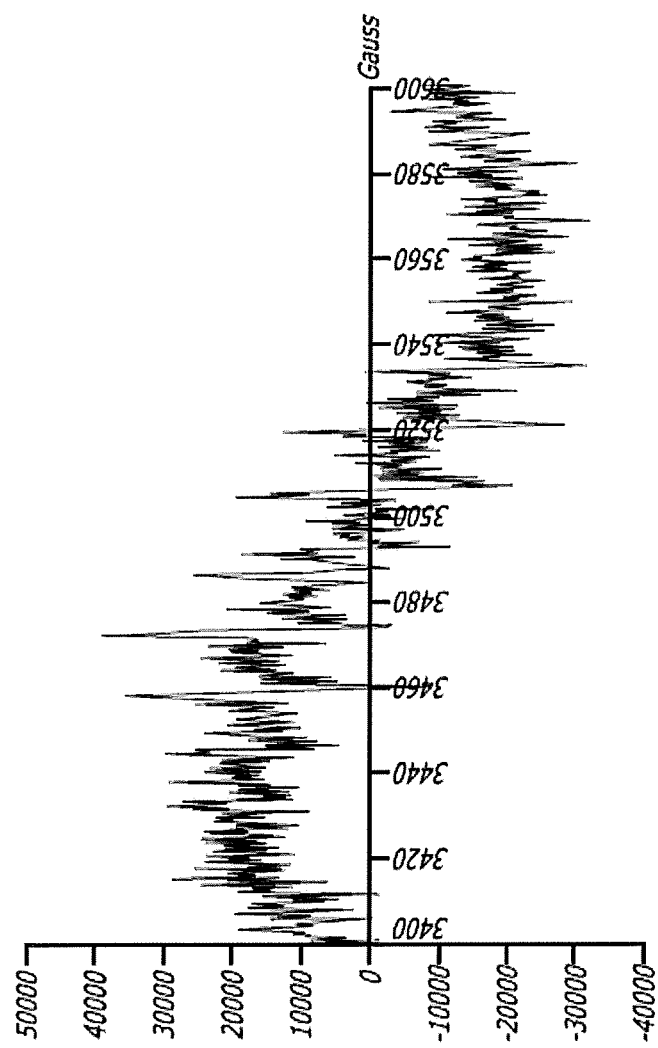
FIG. 13 illustrates an EPR splitting pattern for a free electron.

EPR analysis was performed on the composition with and without DIPPMPO mixed into the solution. FIG. 13 shows the EPR spectrum generated from DIPPMPO mixed with the composition. The composition alone showed no EPR signal after 100 scans (not presented). FIG. 13 illustrates an EPR splitting pattern for a free electron. This electron appears to be split by three different nuclei. The data indicate that this is a characteristic splitting pattern of OH. radical interacting with DMPO (similar to DIPPMPO). This pattern can be described by $^{14}N$ splitting the peak into three equal peaks and $^1H$ three bonds away splitting that pattern into two equal triplets. If these splittings are the same, it leads to a quartet splitting where the two middle peaks are twice as large as the outer peaks. This pattern may be seen in FIG. 13 twice, with the larger peaks at 3457 and 3471 for one quartet and 3504 and 3518 for the other quartet. In this case, the $^{14}N$ splitting and the $^1H$ splitting are both roughly 14G, similar to an OH. radical attaching to DMPO. The two quartet patterns in FIG. 13 are created by an additional splitting of 47G. This splitting is most likely from coupling to $^{31}P$, and similar patterns have been seen previously. The EPR spectrum in FIG. 13 indicates that there is a DIPPMPO/OH. radical species in the solution.

Example 3

Figure 14:
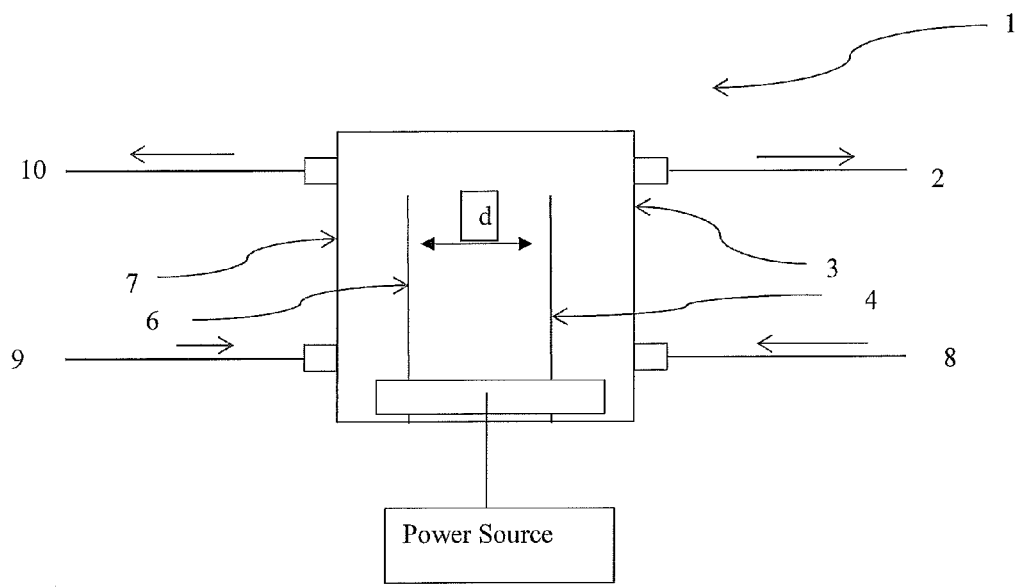
FIG. 14 illustrates an apparatus for electrolyzing fluids wherein no membrane is used.

Water is electrolyzed with an apparatus comprising an anode, a cathode. FIG. 14, illustrates one type of apparatus that can be used. The electrolysis cell 1 comprises an anode 6, and a cathode 4. The anode 6 and cathode 4 were both fashioned as a titanium mesh coated with platinum. The distance between the anode 6 and cathode 4 is shown as d and is less than 1 inch. Sourced salinated water 8 is pumped into a vessel on the cathode side 3 which defines the area in which the cathode 4 and sourced salinated 8 water are brought together. Sourced salinated water 9 is pumped into the vessel on the anode side 7 which defines the area in which the anode 6 and sourced salinated water 9 are brought together. The sourced salinated water 8 and 9 are continuously flowing through the vessel and exiting as electrolyzed water through exits 10 and 2. The cell operated for 1 hour at 40 C using 3 Amps.

Figure 15:
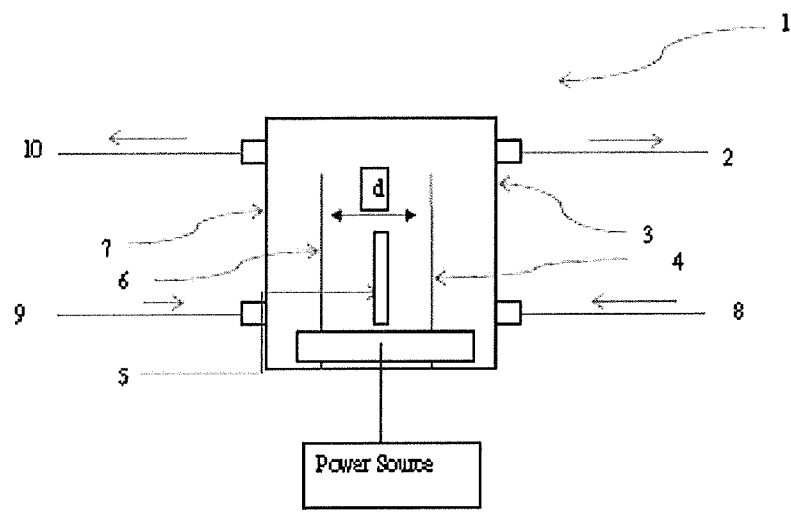
FIG. 15 illustrates an apparatus for electrolyzing fluids wherein a membrane is used.

Referring to FIG. 15, FIG. 15, illustrates another type of apparatus that can be used. The electrolysis cell 1 comprises an anode 6, a cathode 4 and a ion selective membrane 5. The anode 6 and cathode 4 were both fashioned as a titanium mesh coated with platinum. The distance between the anode 6 and cathode 4 is shown as d and is less than 1 inch. Sourced salinated water 8 is pumped into a vessel on the cathode side 3 which defines the area in which the cathode 4 and sourced salinated 8 water are brought together. Sourced salinated water 9 is pumped into the vessel on the anode side 7 which defines the area in which the anode 6 and sourced salinated water 9 are brought together. The sourced salinated water 8 and 9 are continuously flowing through the vessel and exiting as electrolyzed water through exits 10 and 2. The cell operated for 1 hour at 40 C using 3 Amps.

Examples 4-5

Power Sources

Figure 16:
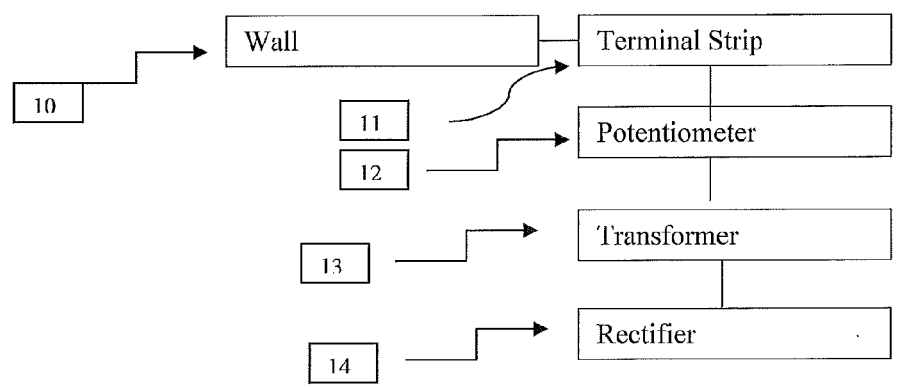
FIG. 16 Illustrates a block diagram of a power source.

FIG. 16 diagrams an example of a power source which can be used in the invention. Electricity comes in from the wall 10 and is met by a terminal strip 11. Terminal strip 11 is in operable communication with a potentiometer 12, and a current transformer 13. Potentiometer 12 is in operable communication with the transformer 13. The transformer 13 is in operable communication with a rectifier 14.

Figure 17:
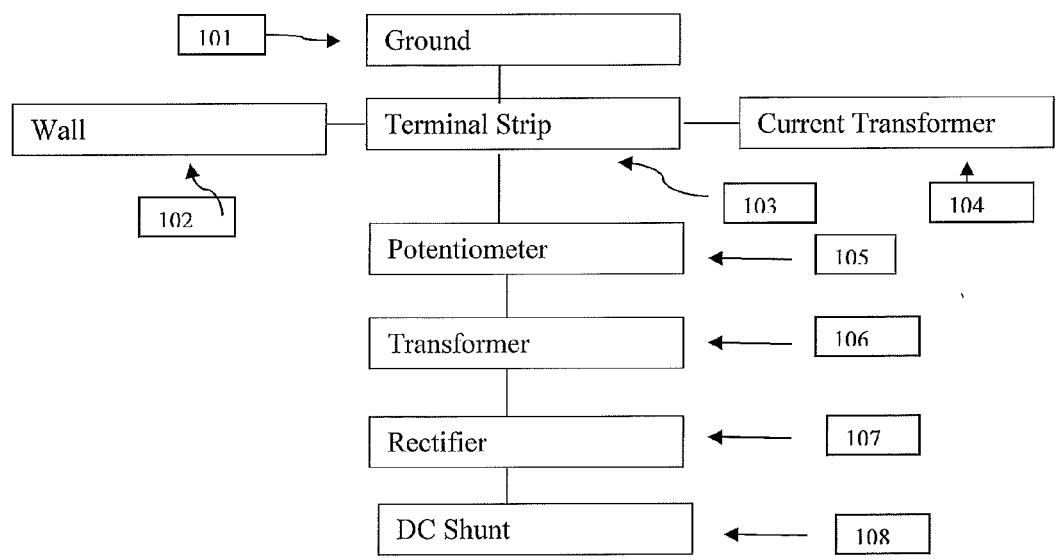
FIG. 17 Illustrates a block diagram of another power source.
Figure 18:
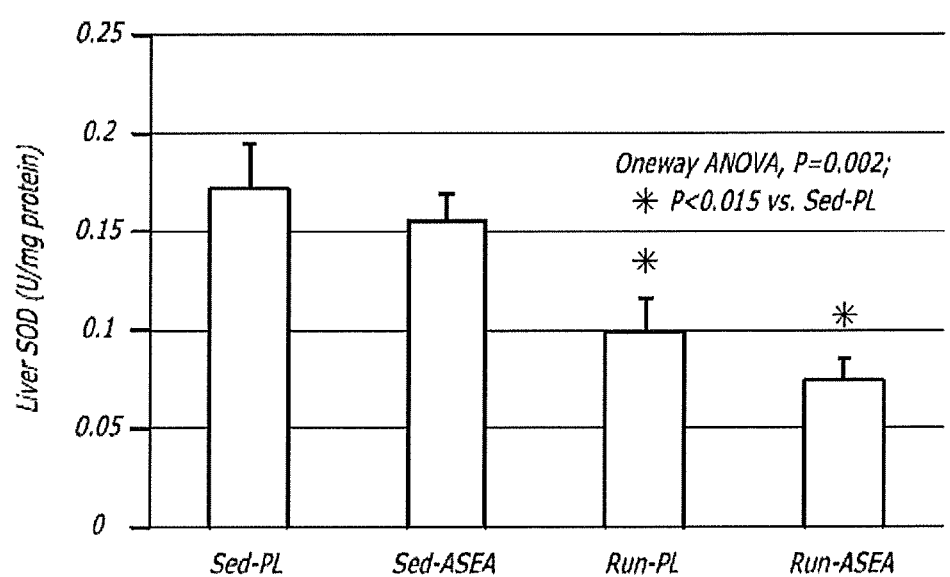
FIG. 18 illustrates different mouse groups versus the amount of liver Superoxide Dismutase (SOD) produced (the composition embodiment used is referred-to as "ASEA").
Figure 19A:
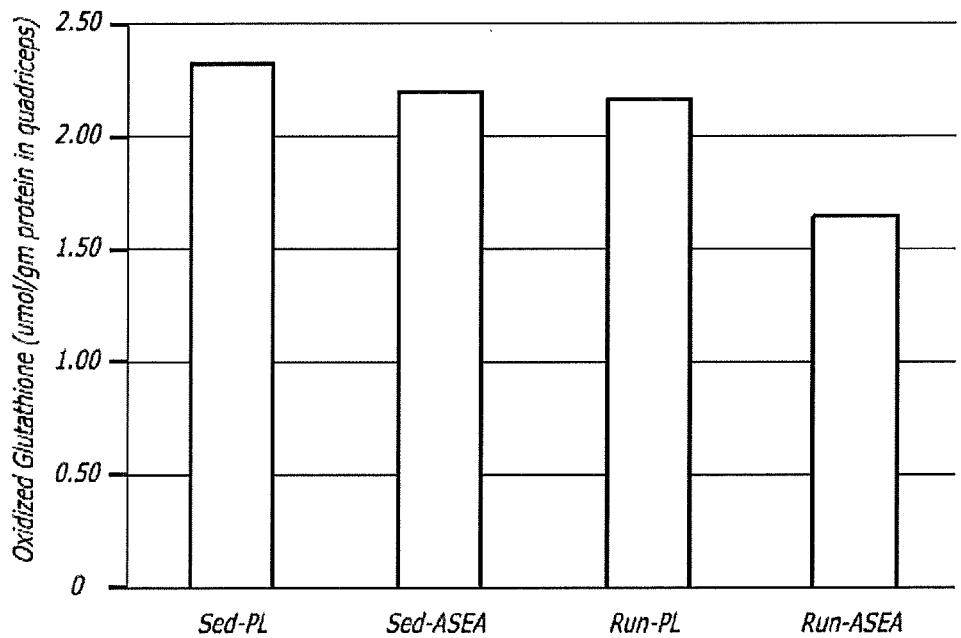
FIGS. 19A and 19B illustrate different mouse groups versus oxidized glutathione (the composition embodiment used is referred-to as "ASEA").
Figure 19B:
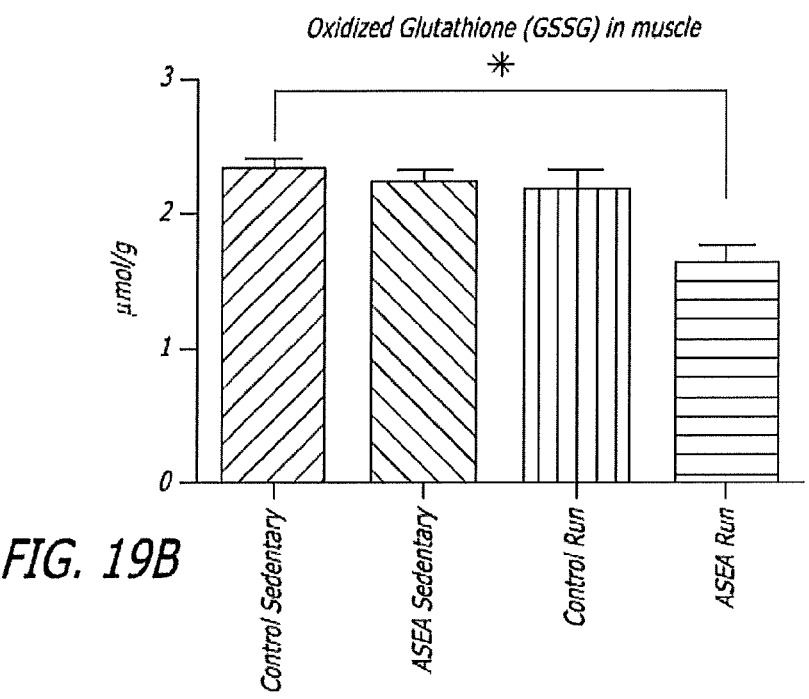
Figure 20:
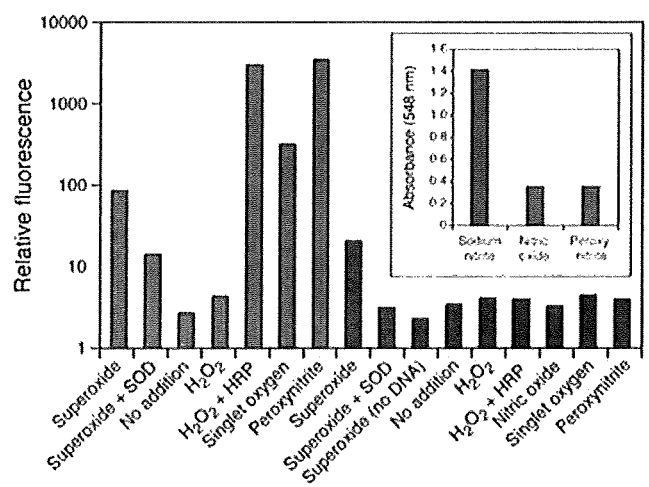
FIG. 20 is a chart of the relative fluorescence of various compositions.
Figure 21:
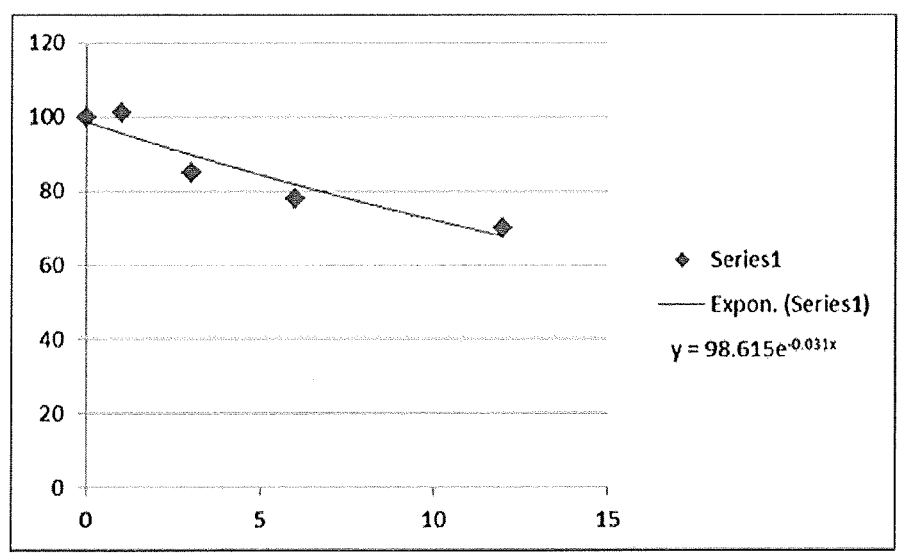
FIG. 21 is a graph of the decay rate of superoxide over a period of 1 year.
Figure 22:
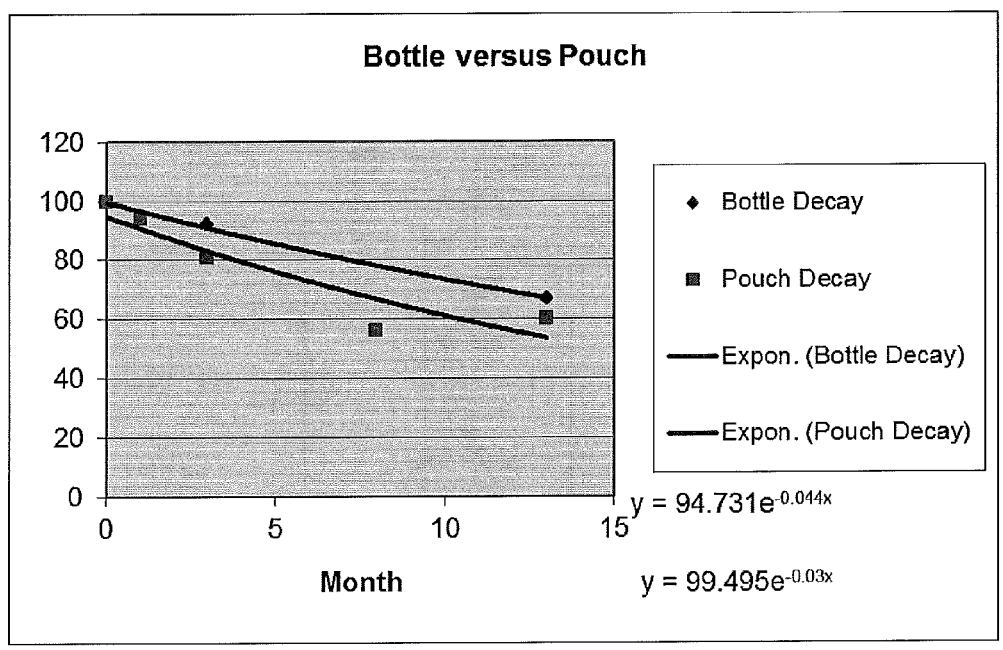
FIG. 22 is a graph showing the comparison of the decay rates of superoxide when the mixture is stored in a bottle and when the mixture is stored in a pouch.

FIG. 17 diagrams an example of a power source which can be used in the invention. Electricity comes in from the wall 102 and is met by a terminal strip 103. Terminal strip 103 is in operable communication with a potentiometer 105, a grounding means 101 and a current transformer 104. Potentiometer 105 is in operable communication with the transformer 106. The transformer 106 is in operable communication with a rectifier 107. Rectifier 107 is in operable communication with a DC shunt 108.

Example 6

In Vitro Bioactivity Study

Described are a variety of results from in vitro experiments, performed at national research institutions, investigating the bioactivity of a composition disclosed herein, when placed in direct physical contact with living cells. Specific investigations include in vitro toxicity and antioxidant efficiencies of the master antioxidants glutathione peroxidase (GPx) and Superoxide Dismutase (SOD) inside living cells and the translocation of two well-studied transcription factors (NF-kB, NRF2) known to regulate toxic response and antioxidant production in human cells. Some preliminary work on concentration dependence was also done as well as cell proliferation, counts associated with induced oxidative stress in human cells.

The objectives of the investigations were (1) to determine if any signs of toxicity (NF-kB activation) are manifest when varying concentrations of a certain redox signaling compound, ASEA, are placed in physical contact with living cells, (2) to determine if such direct contact affects the antioxidant efficacy of glutathione peroxidase (GPx) and superoxide dismutase (SOD) and (3) to determine if such contact activates translocational transcription (NRF2) associated with increased expression of antioxidants in living human endothelial cells and to verify the expression of such transcription factors by Western Blot analysis, (4) to determine the effect of this redox signaling compound on proliferation cell counts of human cells and associated markers (LDH) for cell viability and health, (5) to determine the effects of this redox signaling compound on cells that were stressed with cytokines (Cachexin), radiation and serum starvation.

The immune-supporting composition contains a redox-balanced mixture of RXNs, both reactive oxygen species (ROS) and reduced species (RS), that are involved in a large variety of pathways and receptor-site activity in human cells. For example, when cells are damaged, for any reason (ex. toxins, DNA breaks or infections), the native redox signaling messengers inside the cells can become imbalanced, most often manifest by the accumulation of intracellular oxidants and ROS (oxidative stress). The cell, so affected, will activate defense and repair mechanisms aimed to restore proper redox-signaling homeostasis and proper cellular function. If repair efforts are unsuccessful and normal homeostatic redox balance is not able to be restored, then within a few hours, the excess oxidants and ROS in such cells will facilitate apoptotic processes to internally digest and destroy the dysfunctional cell. Healthy neighboring cells will then divide to replace it. A complete field of science called "redox signaling" has been founded to study such processes, with literally thousands of references available.

It is the nature of certain redox signaling molecules, when unbalanced or isolated, to elicit immediate recognizable toxic responses in exposed living cells; hydrogen peroxide is one example of such a redox signaling molecule. The first-line cellular response to toxic substances involves the translocation of NF-kB into the nucleus as a precursor to the inflammatory response and other defense mechanisms. The movement of NF-kB into the nucleus can be visibly tracked in a living cell under a fluorescence microscope with the aid of fluorescent tag molecules. The observation of nuclear translocation of NF-kB is a sure marker that a toxic response has been initiated. Even low-level toxicity is detectable with this catch-all method; low-level concentrations of hydrogen peroxide, for example, produce an easily distinguishable positive toxic response.

A separate transcription factor, NRF2, moves into the nucleus in response to low-level oxidative stress and facilitates the increased production of antioxidants. Again, by the use of fluorescent tags, the nuclear translocation of NRF2 can be seen in cells under a fluorescence microscope. NRF2 nuclear translocation is a second-line-of-defense mechanism known to increase the production of protective enzymes and antioxidants such as glutathione peroxidase and superoxide dismutase. NRF2 translocation will often accompany low-level NF-kB activation and NF-kB activation (almost) always precedes NRF2 translocation. Substances that exhibit low-level toxicity, such as trace homeopathic toxins, have long been used to activate the NRF2 pathway in order to stimulate these natural defend-repair-replace mechanisms.

Enzymatic efficacy of antioxidants, such as Glutathione Peroxidase (GPx) and Superoxide Dismutase (SOD), can be determined through standardized ELISA tests that measure the time-related reduction of certain oxidants introduced into cell lysates after the living cells have been exposed to the test substance for a given period of time. The reagents of the ELISA test must be chosen as not to interfere or interact with the test substance. Other critical factors such as the time of exposure and concentration dependence must be experimentally determined.

Western Blot methods also exist to experimentally determine the quantities of GPx or SOD in cell lysates. These well-established molecular separation techniques and can be used to directly verify whether the quantity of such antioxidant enzymes has been increased in the sample. Measured antioxidant efficiency, however, remains the best indication of cellular antioxidant defense.

Monitoring cellular proliferation, cell counts and chemical indicators of cellular death are also commonly used to determine cellular viability and gross response to stressors such as radiation, cytokines and toxins. Cachexin, for example, is a potent toxin, a cytokine, that elicits immediate toxic responses and build-up of oxidative stress in exposed cells. Cells, so stressed, exhibit a greater tendency to undergo apoptosis and die, thereby releasing internal proteins (such as LDH) into the surrounding serum.

Normally, when the introduction of such stressors and toxins elicits oxidative stress conditions in the cell cultures, cell counts will fall, cellular proliferation will subside, and serum LDH levels will rise, indicating that cell death is occurring in the culture. Hydrogen peroxide, radiation and serum starvation can also elicit similar responses. Redox signaling messengers, as outlined above, are intimately involved in cellular reception of and response to such stressors; redox messengers are involved in mediating antioxidant production and action to protect the cells, repair mechanisms necessary to fix DNA and structural damage and also in mediating the apoptotic process that results in cell death.

Increasing the concentration of such redox messengers in the serum may serve to augment the efficiency of these normal cellular processes. The exact action of various redox signaling mixtures must be determined experimentally. Independent unpublished studies, involving Mass Spectroscopy, Florescent Spectroscopy and Electron Spin Resonance, have unmistakably verified the existence of several kinds redox signaling molecules in the composition described herein. Well-established redox electrochemistry also validates the existence of such redox signaling molecules. The stability of this redox-balanced mixture is many orders of magnitude greater than expected. The confirmed preservation of unstable moieties in this supplement might be explained by the existence of certain stable molecular complexes, some of them verified by mass spectroscopy that can shield radical interactions. Intellectual property agreements, however, prevent the disclosure of the details.

The following research was conducted on a best efforts basis by a senior researcher at a national laboratory and is designed to assess basic mode-of-action when a composition of the invention is placed into direct contact with human cells:

1. The initial dose range projected for in vitro studies was extrapolated from a 10 mL of a composition of the invention/kg equivalent oral dose from human trials.

2. Glutathione peroxidase (GPx) and superoxide dismutase (SOD) ELISAs were used to determine whether a composition of the invention alters enzymatic activity in murine epidermal (JB6) cells.

3. LDH (non-specific cellular death) levels and cell proliferation rates were determined for various cell types exposed to a composition of the invention.

4. Human microvascular endothelial lung cells (HMVEC-L) were treated with a composition of the invention and cell lysates were analyzed by GSH-Px and SOD ELISAs to determine whether antioxidant enzyme activities are altered.

5. HMVEC-L cells were treated with a phosphate buffered saline solution (PBS) negative control, 5% and 20% concentrations of a composition of the invention and a Cachexin positive control to determine the nuclear translocation activity of the p65 subunit of NF-kB (cytokine transcription) at 30, 60, 90 and 120 min intervals. Fluorescent microscopy techniques were employed to image cellular response.

6. Step (4) was repeated except nuclear translocation activity of P-Jun was determined as an extension/verification of step 4.

7. Two cultures of HMVEC-L cells, one with normal random cell cycles and another with serum starvation were treated with low <1% concentrations of a composition of the invention to determine the nuclear activity of NRF2 (antioxidant transcription) at 30, 60, 90 and 120 minute intervals compared to a negative (PBS) control.

8. A Western Blot analysis was done on extra-nuclear and intra-nuclear fractions, separated by differential centrifugation, of serum starved HMVEC-L cell cultures exposed to <1% of a composition of the invention compared with a positive hydrogen peroxide control to determine phosphorylation events (oxidant action) in the extra-nuclear fraction and NRF2 (antioxidant transcription) in the intra-nuclear fraction at 0, 30, 60, 90 and 120 min intervals.

9. Normal random cell phases of HMVEC-L cells were exposed to radiation and then treated with a composition of the invention. Cell counts were taken to determine survival.

10. The efficacy of Cachexin reception in confluent-phase and normal-phase HMVEC-L cells was determined through changes in extracellular and intracellular LDH activity in cells exposed to various mixtures of Cachexin, PBS and a composition of the invention solutions.

Experimental Methods used to Assess Toxic Response in Primary Human Lung Microvascular Endothelial Cells (HMVEC-L): HMVEC-L cells (catalog# CC-2527) were purchased from Lonza (Walkersville, Md.) as cryopreserved cells (Lot#7F4273). Cells were thawed and maintained according to manufacturer's directions. Cell culture medium (proprietary formulation provided by Lonza) contained epidermal growth factor, hydrocortisone, GA-1000, fetal bovine serum, vasoactive endothelial growth factor, basic fibroblast growth factor, insulin growth factor-1 and ascorbic acid.

HMVEC-L Cell cultures in normal random cell cycles were exposed to high-concentration ASEA in the serum medium, concentrations of 5% and 20%, and analyzed in conjunction with cultures exposed to phosphate buffered saline solution (PBS) as non-toxic negative control and Cachexin (5 ng/mL) as a positive control (highly toxic). At intervals of 0, 30, 60, 90, and 120 minutes, aliquots of cells from each culture were placed under a fluorescent microscope, stained by fluorescent dyes designed to tag the p65 subunit of NF-kB along with a DAPI fluorescent nuclear stain that aids the computer software to find the nuclei. Computer automated imaging techniques were used to determine the relative degree of translocation NF-kB into the nucleus via fluorescent analysis over several cells. As a reminder to the reader, P65 NF-kB translocation is the first-phase non-specific cellular response to toxicity. Thus the movement of the NF-kB into the nucleus, as seen visually in the microscope images, is a sensitive indicator of general toxic response.

Figure 25:
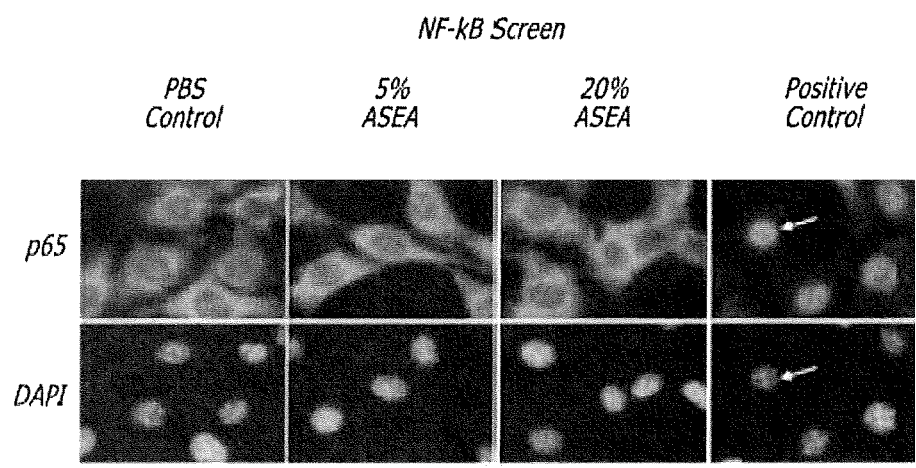
FIG. 25 illustrates cell images for each culture results of HMVEC-L Cells p65 subunit NF-kB screen for toxicity (the composition embodiment used in the protocol is referred-to as "ASEA").

Results of HMVEC-L Cells p65 subunit NF-kB screen for toxicity: Typical cell images are shown below for each culture. Translocation of p65 subunit of NF-kB into the nucleus was not seen in any cell cultures exposed to high-concentration a composition of the invention. Automated analysis confirmed this and indicated no toxic response at 0, 30, 90 and 120 minutes. In contrast, Cachexin exposed cells exhibited an immediate sustained toxic response (FIG. 25).

Cachexin is positive control and induces the translocation of p65 subunit of NF-kB from cytosol into nucleus. DAPI staining shows position of nuclei in these images (see arrow of FIG. 25). A composition of the invention (5 and 20% final v/v) did not induce nuclear translocation of NF-kB at 30, 60 and 120 min time points.

Given this null indication of toxicity after exposure to high concentrations of ASEA, another test was performed to confirm behavior.

Additional Method to Assess Toxic Response of HMVEC-L Cells (P-Jun): A similar methodology as that employed with NF-kB was employed to determine the nuclear translocation of an anti-phospho-Jun (AP-1 P-Jun) antibody index (P-Jun is another toxicity-related redox-responsive transcription factor). HMVEC-L cells were again exposed to high-concentration ASEA. All procedures were similar to the NF-kB analysis except for the substitution of P-Jun fluorescent indicators and automated measurements taken over 100 cells in order to increase sensitivity. An additional naïve (untouched) culture was also analyzed.

Figure 26:
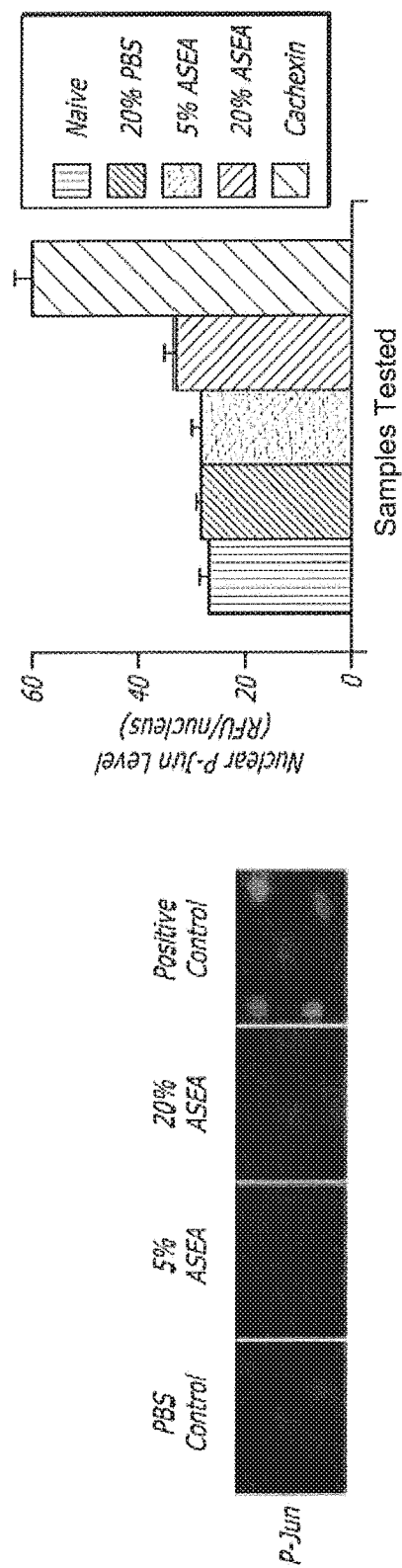
FIG. 26 illustrates results for P-Jun screen for toxicity (the composition embodiment used in the protocol is referred-to as "ASEA").

Results for P-Jun screen for toxicity (FIG. 26): AP-1 index determined using anti-phospho-Jun (P-Jun) antibody. AP-1 is nuclear localized and upon activation, the phosphorylation status of P-Jun is increased. Anti-P-Jun antibody binds to the phosphorylated form reflected as an increase in fluorescence intensity (see Cachexin control). A consistent trend reflecting an increase in P-Jun levels was not observed for cells treated with 5% or 20% ASEA at 30, 60 and 120 min time points, while the Cachexin positive control significantly increased nuclear P-Jun levels at 30 min.

Again no toxic response was observed; there was no significant accumulation of P-Jun in the nuclei of cell cultures exposed to high concentrations of a composition of the invention. Automated analysis indicated no toxic response at 0, 30, 90 and 120 minutes, with a slight but non-significant increase for 20% a composition of the invention at the 30 minute time point; at other time points no increase was detected. In contrast, the Cachexin exposed cells (positive control), as expected exhibited an immediate sustained toxic response.

The results of the P-Jun analysis concurred with the response seen in the NF-kB analysis. For both tests, there was no significant difference between a composition of the invention exposure and that of the negative PBS control for healthy random-phase HMVEC-L cells. This confirmed lack of toxicity was somewhat unexpected for this mixture of redox signaling molecules, considering that some of them, if isolated from the mixture, are known to elicit an immediate response.

Since nuclear translocation of NF-kB and P-Jun are typically the first responders to serum toxicity and are known to initiate the inflammatory response, especially in the ultra-sensitive human endothelial cells, healthy human cells when directly exposed to a composition of the invention, are not expected to exhibit defensive behavior nor initiate inflammatory processes (such as the release of inflammatory cytokines). It is not certain from this data whether exposure would suppress or reverse the inflammatory process.

Blood serum levels of such redox signaling molecules, for all in vivo oral applications, would not exceed serum concentrations of 1% and typically would be less than 0.1%. Serum levels are expected to drop over time due to enzymatic breakdown of the components. Independent in vivo pharmacokinetic studies indicate that the active components in ASEA have approximately a 17 minute half-life in the blood and thus would be effectively cleared from the blood within a few hours. Thus no toxic response is expected due to exposure of healthy human cells at such levels. It has been seen in these in vitro studies that direct exposure of human cells to serum concentrations of up to 20% is still well tolerated. The complete lack of toxicity, comparable to the PBS control, is extremely rare and indicates that despite the reactivity of this mixture, it is well tolerated by human tissues and is native to or compatible with the extracellular environments.

Experimental Methods Used to Determine Antioxidant Efficacy of Glutathione Peroxidase (GPx): Cell cultures of standard murine epidermal cells (JB6) were exposed to various small concentrations of a composition of the invention (less than 1%) and PBS solution for 24 hours. Cell lysates were prepared for measurements of GPx enzymatic activity using a commercially available ELISA kit (GPx activity kit, Cat #900-158) according to directions of the manufacturer (Assay Designs, Ann Arbor, Mich.). Decrease of oxidants due to GPx enzymatic activity was monitored over an 11 minute period of time after a chemical agent (cumene hydroperoxide) initiated the reaction. The decrease of oxidants is an indication of antioxidant efficacy. To determine GPx efficacy at various concentrations of PBS or a composition of the invention, three replications of oxidant residual in the samples were read every 2 min to generate the slope, indicating the decrease in relative fluorescence units (RFU)(oxidant residual) per minute.

Figure 27:
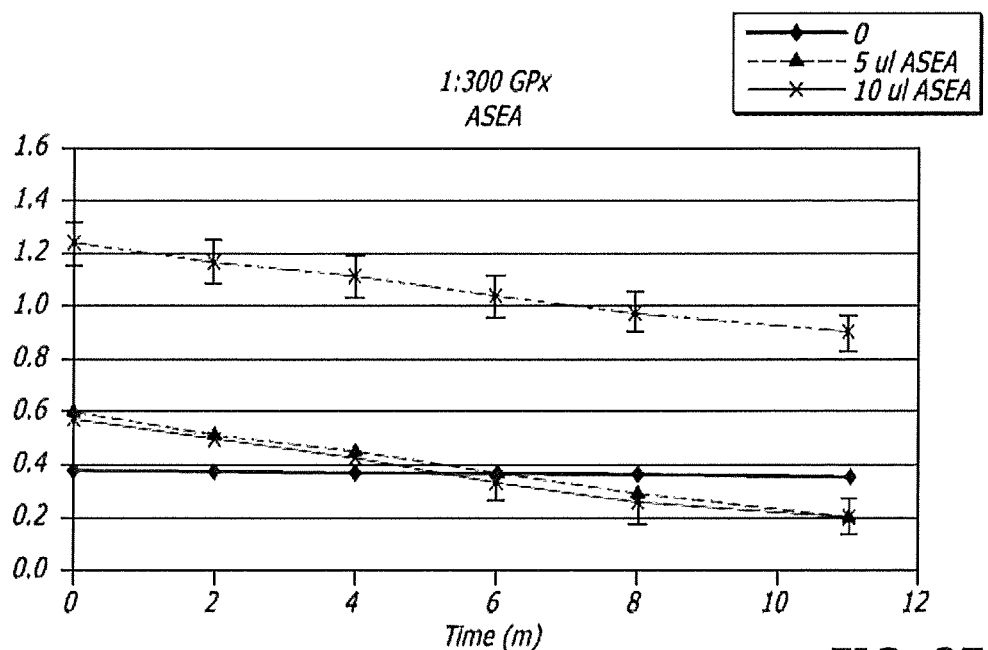
FIG. 27 illustrates a graph showing the reduction of oxidants over an 11 minute interval (RFU units on vertical scale).
Figure 28:
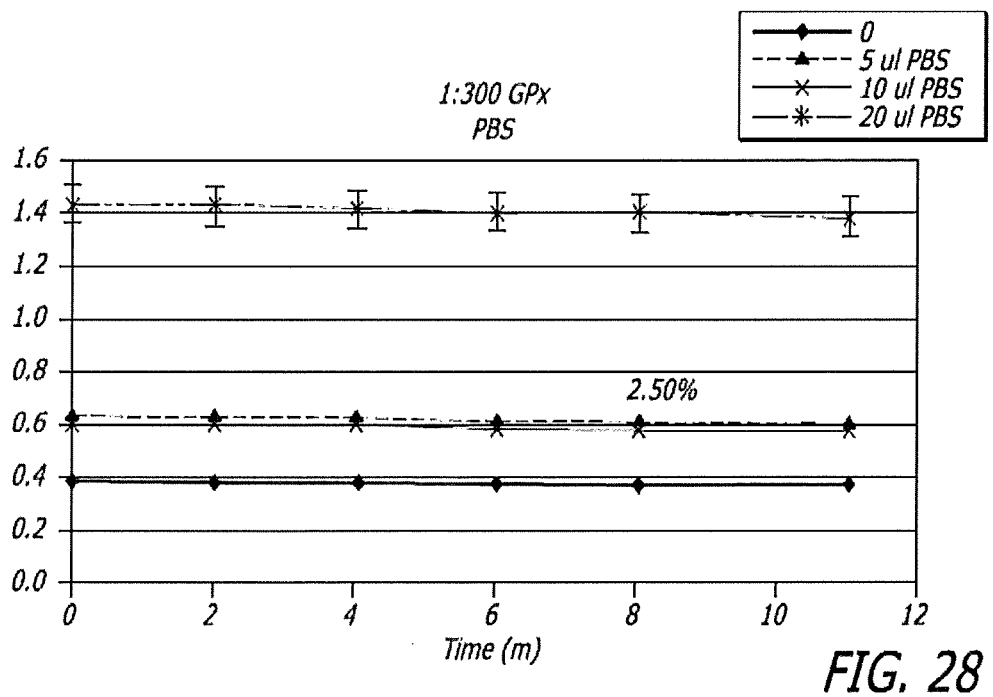
FIG. 28 illustrates a graph showing antioxidant activity over an 11 minute interval (the composition embodiment used in the protocol is referred-to as "ASEA").

Results and Observations for GPx Antioxidant Efficacy Test: After activation, the reduction of oxidants over time was closely linear, as seen in the graphs below (RFU units on vertical scale). A well-defined slope was established over the 11 minute interval (FIG. 27). Antioxidant activity is measured by reduction of oxidants over time (FIG. 28).

A significant increase in antioxidant activity was seen in samples infused with ASEA compared to the PBS control (second graph).

Concentration dependency, however, was not seen between the 5 ul, 10 ul and 20 ul infusions. This suggests that GPx antioxidant activity might saturate at concentrations lower than that represented by the 5 ul infusion. Such considerations will be discussed later.

The table below summarizes the data shown on the preceding graphs.

| Sample Infusion Volume (<1% total volume) | Slope for PBS Control (% reduction/minute) | Slope for ASEA (% reduction/minute) |
| --- | --- | --- |
| 0 ul | 0.1% | 0.1% |
| 5 ul | 0.1% | 3.6% |
| 10 ul | 0.2% | 3.6% |
| 20 ul | 0.3% | 3.7% |

The raw data reflects more than a 10 fold increase in antioxidant activity related to ASEA infusion. Taking into account experimental uncertainties, it is 98% certain that the serum infusion of small concentrations (<1%) of a composition of the invention increased antioxidant efficiencies by at least 800%. Further investigations should be done to confirm this increase and explore concentration dependence for these low-level serum concentrations.

Experimental Methods Used to Determine Antioxidant Efficacy of Superoxide Dismutase (SOD): Human HMVEC-L cells were treated with 10% phosphate buffered saline (PBS; vehicle control), 5% or 10% of a composition of the invention for 24 hr at which time cell lysates were prepared for measurements of SOD activity using a commercially available kit (SOD activity, cat#900-157) according to manufacturer's (Assay Designs, Ann Arbor, Mich.) directions. Cell culture medium was assayed for SOD activity in parallel. Limited trials with smaller concentrations of a composition of the invention <1% and murine epidermal cells were also attempted.

Results of First-Attempt Methods to Determine SOD activity for high serum a composition of the invention concentration: Diluted lysates showed a marginal increase in enzymatic activity associated with treatment with a composition of the invention. Changes in enzymatic activity were marginal in the initial range of 5-10% a composition of the invention (final concentration, v/v). The data represent the first attempt to measure SOD activity using primary HMVEC-L cells treated with a composition of the invention. It is feasible that the lack of SOD activity associated with 5-10% a composition of the invention might be related to non-specific inhibition at high dose. The primary concern is that we have little understanding of the primary human HMVEC-L cell model and cannot determine whether these cells are optimal for investigating antioxidant defense regulation induced by a composition of the invention. For example, ascorbic acid, known to break down certain redox signaling complexes in a composition of the invention, is supplemented into the medium and it is feasible that some modification of the medium formula (such as omission of ascorbic acid for short periods of time defined empirically) could produce more optimal conditions for detecting antioxidant defense regulated by a composition of the invention. Initial efforts to serum-starve these cells, as one approach to increase sensitivity and optimize the model, were unsuccessful and resulted in extensive cell death over 24 hours, indicating that the cells are dependent on the growth factors supplemented in the cell culture medium to maintain cell viability. If we interpret the initial a composition of the invention concentrations (5-10%) to be high (based on inhibition of medium enzymatic activity and cell proliferation), then it is possible that the marginal increase in enzymatic activity associated with cell lysates observed here may not accurately reflect antioxidant defense regulation possibly occurring at lower concentrations. The use of an in vitro model system with a well defined and robust NRF2-regulated antioxidant defense response would help address some of these uncertainties. In retrospect, we have observed that a lower concentration of a composition of the invention (1%) induces the nuclear translocation of the NRF2 transcription factor. In addition, the 24 hr time point was chosen for the initial screen as a general time point for in vitro investigations that would capture transcriptional regulation; however, this time point was not optimal.

Results of Further Investigations into SOD enzymatic activity at low composition of the invention concentrations (<1%): It was found in another investigation that NRF2 nuclear translocation (data and results are in the following sections), took place at low doses of a composition of the invention (less than 1%) and elicited peak SOD antioxidant activity at about 30 to 120 minutes after exposure. Thus when SOD antioxidant activity was measured due to low-concentration composition of the invention exposure at 30 to 120 minute time points, results similar to the GPx enzymatic activity were seen both with murine epidermal (JB6) cells and serum-starved HMVEC-L cells at a time point 90 to 120 minutes. A 500% increase in peak SOD enzymatic activity was estimated over a short 120 minute term, with 95% confidence.

Experimental Methods Used to Determine Nuclear Translocation of NRF2 in HMVEC-L Cells and Western Blot Verification: HMVEC-L cells were again thawed and maintained according to manufacturer's directions. The culture medium contained epidermal growth factor, hydrocortisone, GA-1000, fetal bovine serum, vasoactive endothelial growth factor, basic fibroblast growth factor, insulin growth factor-1 and ascorbic acid in randomly cycling cultures. Ascorbic acid was withheld from serum-starved cultures.

HMVEC-L Cell cultures in both normal random cell cycles and in serum starvation were exposed to high-concentration (5-20%) and low-concentration (1%) ASEA in the serum medium and analyzed in conjunction with cultures exposed only to phosphate buffered saline solution (PBS), as a negative control. At time points of 30, 60, 90, and 120 minutes, aliquots of cells from each of the cultures were placed under a fluorescent microscope, stained by a fluorescent dye designed to tag the NRF2 transcription factor along with the DAPI fluorescent nuclear stain that aids the computer software to find the nuclei. Computer automated imaging techniques were used to determine the relative degree of nuclear accumulation of NRF2 via fluorescent analysis over several cells. NRF2 regulates the transcription of a number of phase II antioxidant defense enzymes and raises the possibility that additional antioxidant defense enzymes, such as glutathione transferase, may be expressed through exposure to ASEA. Thus the accumulation of NRF2 into the nucleus, as seen visually in the microscope images, is an indicator of increased antioxidant expression in the cells.

Figure 29:
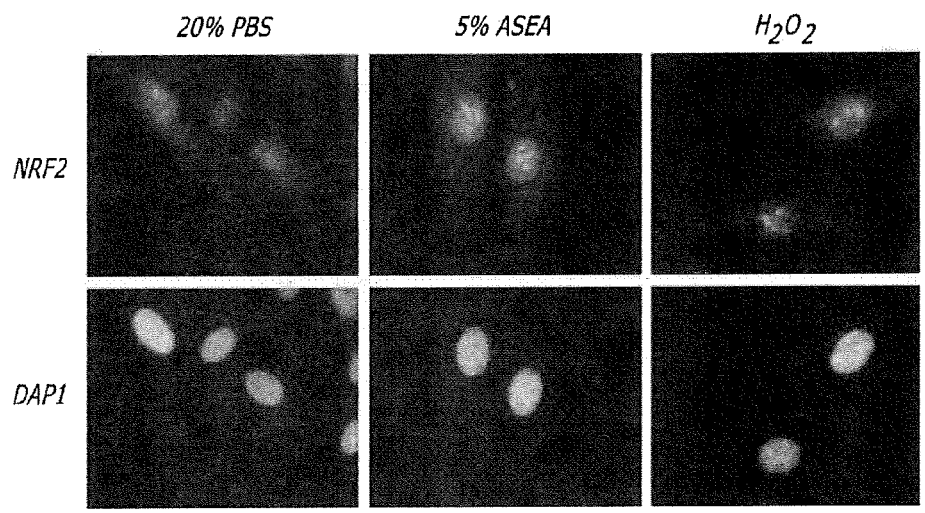
FIG. 29 illustrates nuclear staining patterns for results of HMVEC-L Nuclear Accumulation of NRF2 (the composition embodiment used in the protocol is referred-to as "ASEA").

Results of HMVEC-L Nuclear Accumulation of NRF2: Initial screen of human endothelial cells suggests a subpopulation of cells showed increased nuclear staining pattern (focal) following treatment with high-concentration of a composition of the invention. The positions of nuclei are indicated by DAPI stain in lower panel. Foci appear brighter in a composition of the invention stimulated cells which indicates higher level of NRF2 transcription factor in the nucleus. $H_2O_2$ was used as positive control. This effect was difficult to quantify based on nuclear staining pattern. (FIG. 29).

Figure 30:
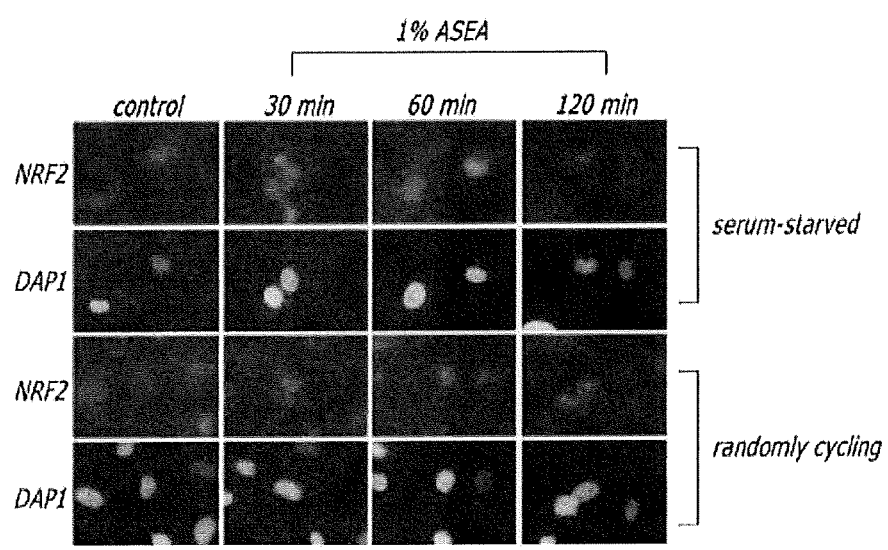
FIG. 30 illustrates serum-starved cell cultures exposed to low-concentration ASEA (a composition disclosed herein).

Typical cell images are shown below for indicated cell cultures exposed to low-concentrations of a composition of the invention. Accumulation of NRF2 into the nucleus was clearly seen in serum-starved cell cultures exposed to low-concentrations of a composition of the invention. Automated analysis revealed strong time-dependent nuclear accumulation of NRF2 in serum-starved cells, relative to the negative control, at the 30 and 60 minute time points (FIG. 30).

The nuclear staining profile was qualitatively different from the cells maintained in optimal growth medium (randomly cycling group). There was weak qualitative nuclear accumulation of NRF2 induced by exposure to a composition of the invention in these cells at 30, 60 and 120 minute time points, and yet the effect was not nearly as pronounced as in the serum-starved cultures. However, serum-starvation induced significant cell death complicating interpretation of the data. The trends appeared weak and require validation by Western Blot.

Experimental Methods for Western Blot Validation of NRF2 Nuclear Accumulation: HMVEC-L were treated with 1% of a composition of the invention, nuclear extracts were separated through centrifugal differentiation from the extra-nuclear cytosol at 30, 60 and 120 min and subjected to Western Blot analysis for NRF2. In the Western blot experiment the extra-nuclear fraction was probed for phosphorylated proteins using a combination of anti-phospho serine, threonine and tyrosine antibodies. Virtually all cellular processes are regulated by posttranslational modifications and protein phosphorylation is a prevalent mechanism. Observable changes in protein phosphorylation can lead to a mechanistic understanding of the cellular processes perturbed by compositions of the invention and provide a defined endpoint to better define dose-dependent regulation of cell function by compositions of the invention in vitro, as well as provide a potential candidate molecular marker that may be used to provide in vitro-in vivo correlates. Hydrogen peroxide ($H_2O_2$) was included as a positive control for oxidant damage.

Figure 31:
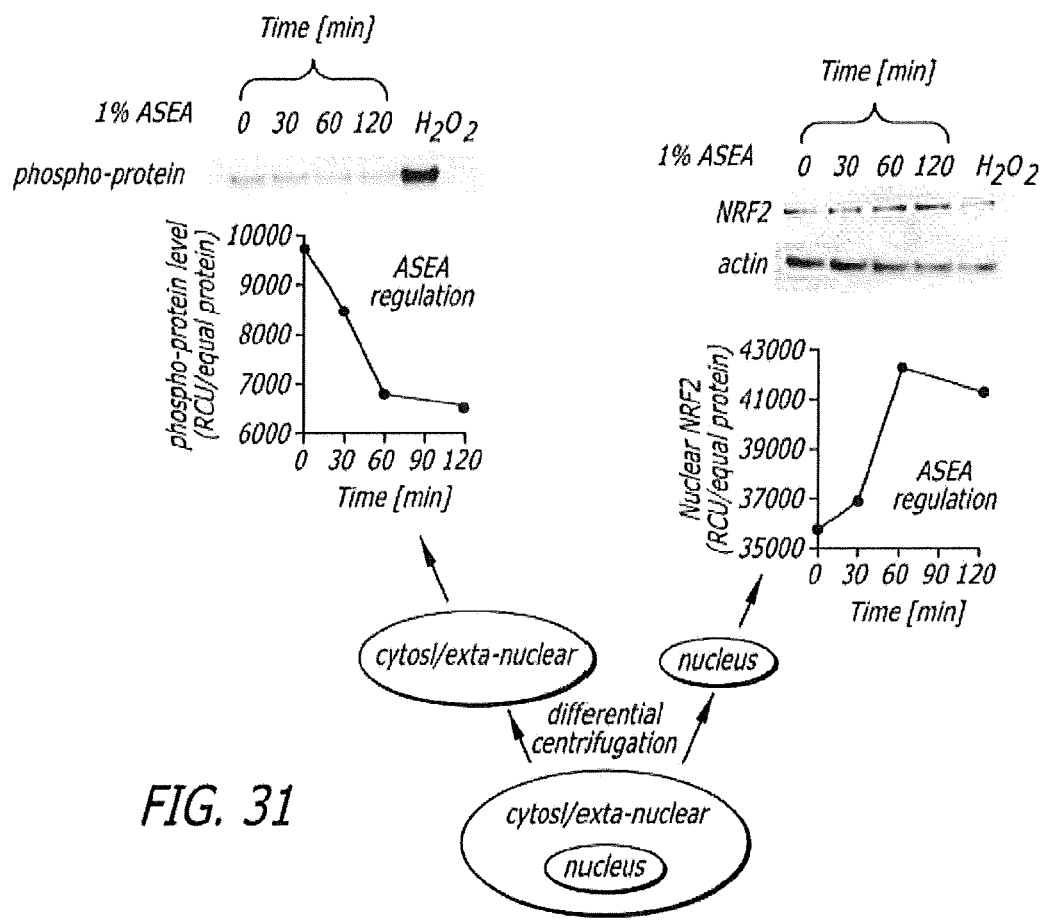
FIG. 31 illustrates a western blot validation of NRF2 nuclear accumulation following ASEA treatment.
Figure 32:
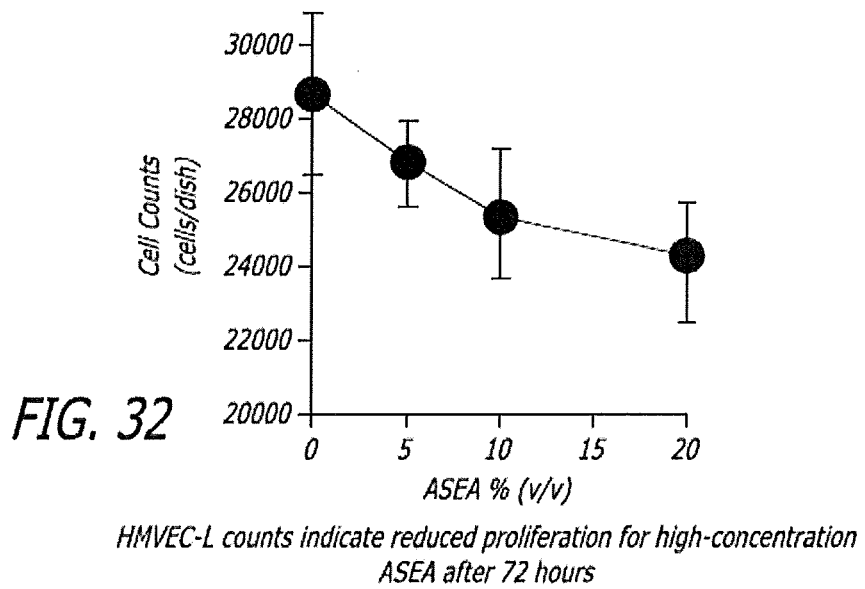
FIG. 32 illustrates results for proliferation of murine and HMVEC-L cells and LDH activity following ASEA treatment.
Figure 33:
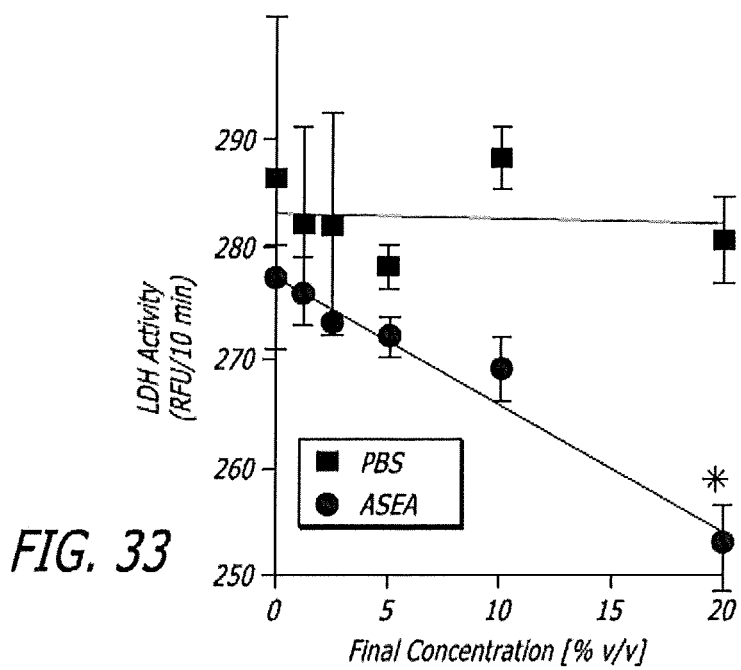
FIG. 33 illustrates further results for proliferation of murine and HMVEC-L cells and LDH activity following ASEA treatment.

Results for Western Blot Validation of NRF2 Nuclear Accumulation: NRF2 levels were increased in a time-dependent fashion in nuclear extracts prepared from HMVEC-L cells treated with 1% ASEA. $H_2O_2$ (30 min) did not increase nuclear NRF2 levels. In contrast, when protein phosphorylation was examined in the extra-nuclear fraction (separated from nuclei by differential centrifugation) we observed a single band by Western blot analysis and this is likely due to the dilution of the extra-nuclear fraction during the cell fractionation process (other phosphorylated proteins are obviously present but are below detection limits under these conditions) or specificity of the anti-phospho-antibodies used was insufficient to detect a broad range of phosphorylated proteins. However, we did observe a marked increase in the phosphorylation of the protein detected following $H_2O_2$ treatment, indicating that this phosphorylation event is highly sensitive to redox regulation or activation of protein kinase/deactivation of protein phosphatase activities subsequent to oxidative damage. Treatment of cells with 1% of a composition of the invention decreased phosphorylation levels associated with this protein in a time-dependent fashion (FIG. 31).

Reductions in phosopho-protein regulation in extra-nuclear fractions were seen along with strong time-dependent NRF2 accumulations in the nuclear fractions, indicating clear time-dependent up-regulation of antioxidant expression.

At this point it is worth mentioning that NRF2 activity has been clearly detected in conjunction with exposure to a low-concentration of a composition of the invention without the normal prior NF-kB activity. This suggests that phase II antioxidant defense mechanisms have been stimulated without the normal prior phase I toxic response. This behavior has no precedent or is extremely rare. It appears from the data that compositions of the invention are able to stimulate antioxidant expression without ever eliciting a prior low-level phase I toxic response.

Experimental Methods to Determine Proliferation of Murine (JB6) Cells and HMVEC-L Cells and LDH Activity with Exposure to ASEA: HMVEC-L cells were treated with 5-20% ASEA for 72 hr and cell number was determined using a Coulter Counter. Control (0 concentration group) was treated with 20% PBS. Serum LDH levels were also measured as an indicator of cell culture viability at 0 to 20% concentration of the compositions of the invention/serum concentrations. Recall that lower serum LDH concentrations indicate less cell membrane failure. Similar experiments were performed for murine (JB6) epidermal cells.

Results for Proliferation of Murine and HMVEC-L cells and LDH activity: The initial in vitro screen indicates that high-concentrations of compositions of the invention in serum may inhibit cell proliferation (for both murine epidermal cells [JB6] and primary human lung microvascular endothelial cells [HMVEC-L]) in the concentration range of 5-20%. In this concentration range we also observed direct inhibition of LDH enzymatic activity. The data are somewhat contradictory as the decreasing cell counts indicate cell death, yet lower serum LDH levels indicate higher cellular membrane integrity. At the highest concentration tested (20% v/v), cell proliferation was inhibited by approximately 20%.

The mechanism behind reduced proliferation cannot be deduced and could be related to interference with growth factor responsiveness or other possible interpretations such as enhanced programmed death (apoptotic response) for damaged cells. It is noteworthy that high serum concentrations of composition of the invention for in vitro enzymatic enhancement studies is not optimal, it is possible that the initial screens underestimated or even missed antioxidant defense (SOD) regulation by a composition of the invention and thus indicate that low-concentration (<1%) compositions of the invention and/or short exposure times should be employed for such purpose.

Further studies were done that investigated the action of stressed cells upon exposure to compositions of the invention; the source of stress resulting from a variety of chemical and environmental stressors. These investigations offer clues for the possible mechanisms.

Experimental Methods to Determine cell viability of HMVEC-L exposed to various mixtures of Cachexin stressor and high-concentration compositions of the invention: HMVEC-L cultures with normal random cell cycles (pS) and cultures approaching confluence (A2), which are generally less sensitive to Cachexin, were infused with escalating concentrations of Cachexin stressor (0-5 ng/mL). These cultures had been pretreated with either a 10% PBS control or 5-10% concentration of a composition of the invention for 24 hours. Two indicators for cell viability were employed. Serum LDH levels were obtained as an indication of membrane integrity and Neutral Red dye was used as an indication of lysosomal integrity. Recall that as cell membranes fail, LDH is released into the serum medium. Lower quantities of LDH indicate higher cell viability. The integrity of lysosomes, necessary for viable cell function, are measured by absorption of Neutral Red dye stain. Higher quantities of Neutral Red absorbance indicate higher cell viability.

Figure 34:
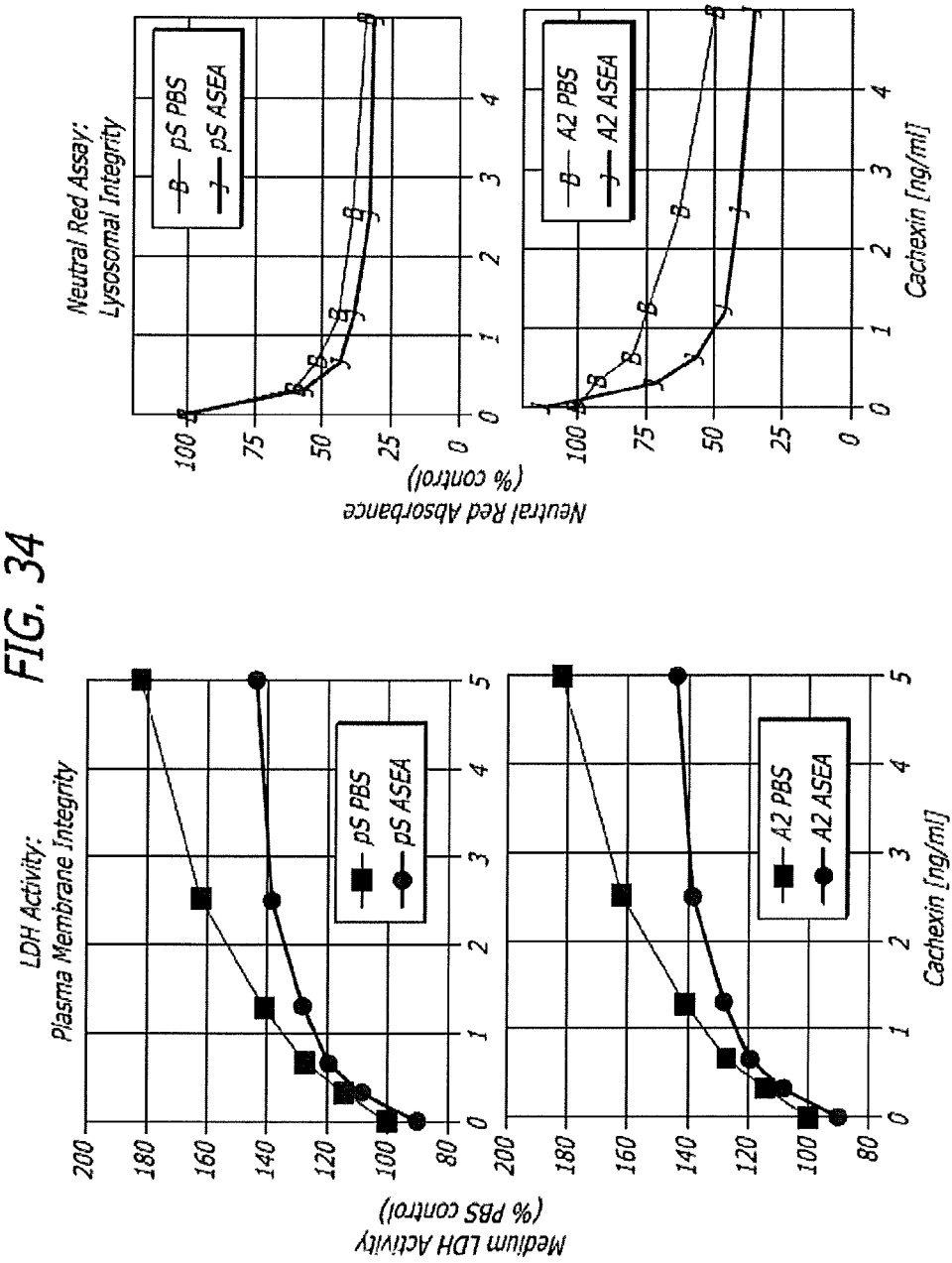
FIG. 34 illustrates results of HMVEC-L viability exposed high-concentration ASEA and to escalating amounts of Cachexin stressor (the composition embodiment used in the protocol is referred-to as "ASEA").

Results of HMVEC-L viability exposed high-concentration composition of the invention and to escalating amounts of Cachexin stressor (FIG. 34): Both confluent (A2) and normal (pS) HMVEC-L cultures exhibited up to 30% improvement (relative to PBS controls) in LDH levels related to exposure to compositions of the invention after acute (up to 5 nm/mL) Cachexin insult. The LDH data suggest that HMVEC-L cells stressed by Cachexin are less likely to die due to cell membrane failure after being exposed to compositions of the invention.

Behavior of lysosomal integrity in HMVEC-L cells as measured by Neutral Red absorption exhibited behavior dependent on cell culture phase. As expected, the confluent (A2) cells in the PBS control were much less sensitive to Cachexin insult than cells in the PBS control normal random phase (pS) culture; this is evidenced in the 5 ng/mL Cachexin data: Lysosomal levels in A2 cells dropped only 50% compared to 70% in the pS culture. Exposure of the normal (pS) cultures to compositions of the invention made little difference in lysosomal integrity under similar Cachexin insult, yet exposure of confluent (A2) cell cultures to ASEA made them much more sensitive to Cachexin insult, regressing to behavior similar to that exhibited by the normal more sensitive (pS) cells.

This is the first evidence presented that suggests that exposure of abnormal (Cachexin-insensitive) HMVEC-L cells to compositions of the invention can make them more sensitive. The data suggest that confluent (A2) cells stressed by Cachexin are more likely to die when exposed to compositions of the invention, these abnormal cells when exposed to ASEA exhibit closer to normal behavior in the presence of Cachexin. This behavior was initially unexpected as the hypothesis of the experiment was that compositions of the invention would help cells protect themselves against toxic insult. As it turns out, it appears that compositions of the invention exposure only helps normal healthy cells to protect themselves against oxidative insult and yet seems not to help cells protect themselves against Cachexin. Exposure to compositions of the invention may even help facilitate the death of the stressed cells that are close to the end of their normal life cycle. Incidentally, the normal role of Cachexin in the tissues is to facilitate the death and replacement of damaged cells.

Experimental methods to determine the compositions of the invention concentration-dependent response of A2 and pS phase HMVEC-L cells to Cachexin insult: HMVEC-L cell cultures, prepared in two phases, in the confluent end-of-life-cycle A2 phase (a phase typically insensitive to Cachexin insult) and in the normal random cycle pS phase were exposed for 24 hours to serum concentrations (v/v of 2.5%, 5%, 10%, 15% and 20%) of either the PBS control or a composition of the invention. Cachexin responsiveness was then determined by monitoring LDH activity in both the intracellular cytosol and in the surrounding growth media. Recall that increased LDH activity in the growth media indicates cell membrane rupture and death (LDH release) and the decrease of intracellular LDH activity indicates loss of cellular integrity. Thus the cell cultures that are responsive to Cachexin insult would experience an increase in medium LDH activity and a decrease in intracellular LDH activity.

LDH activity in untouched cell culture controls were compared to that of cell cultures insulted with 5 ng/mL Cachexin for each composition of the invention concentration considered. The concentration dependence of compositions of the invention was then graphed against LDH activity for each insulted culture and control.

Figure 35:
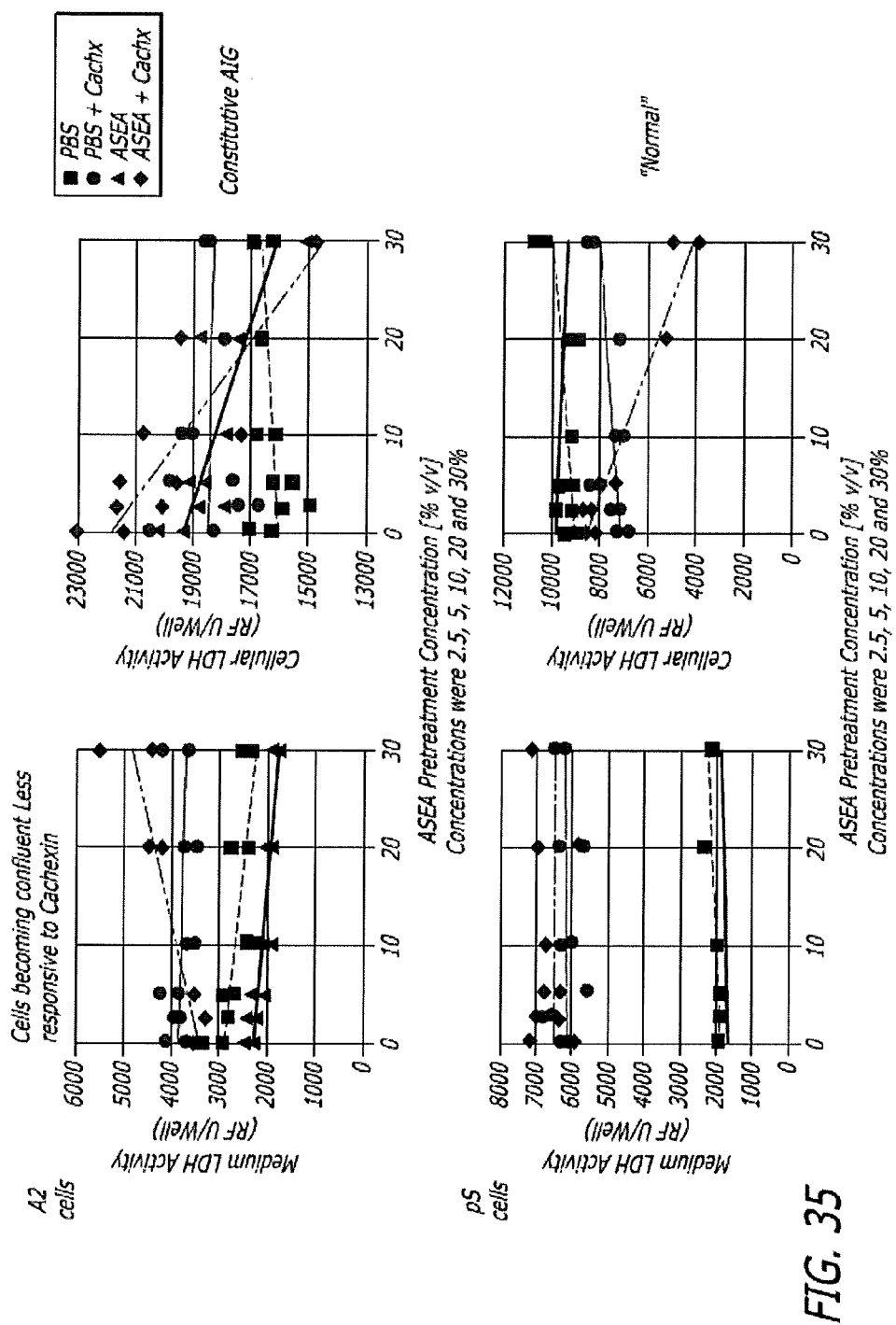
FIG. 35 illustrates results of concentration-dependent response of HMVEC-L cells to Cachexin insult (the composition embodiment used in the protocol is referred-to as "ASEA").

Results of concentration-dependent response of HMVEC-L cells to Cachexin insult (FIG. 35): Relative to the PBS control, the Cachexin response for the normal pS cells was much smaller than expected. Only slight decreases in cell membrane integrity were seen in the PBS control cultures and the intracellular LDH activity remained the same. With exposure to compositions of the invention, by itself, the normal pS cell cultures suffered a slight decrease in overall cellular integrity and increase in cell death. It should be noted that since the large expected response of the control pS cells to Cachexin was not manifest, it is probable that the pS cell cultures used in this investigation were nearing a confluent or non-responsive state.

There was, however, a clear response when Cachexin insult was added to the pS cell cultures exposed to various composition of the invention concentrations, cultures demonstrated a clear loss of intracellular LDH function and integrity. However, the accompanying indication of cell death was not seen. This seems to indicate that the "normal pS" cells were made more sensitive to Cachexin reception by composition of the invention exposure, yet not brought completely to the point of cell death.

The A2 cell culture response was very clear. Composition of the invention exposure, even without Cachexin, seemed to cause loss of intracellular LDH integrity, though it did not affect cell death. However, when Cachexin insult was applied to such A2 cultures, composition of the invention exposure clearly amplified the Cachexin reception rapidly decreasing cellular function and there were also clear indications of concentration-dependent cell death. There is strong evidence that exposure to compositions of the invention increases Cachexin responsiveness in the A2 cell cultures.

The results imply that exposure to compositions of the invention significantly increases Cachexin responsiveness in A2 and borderline pS HMVEC-L cell cultures. Of possible interest, exposure to compositions of the invention alone might decrease integrity of cellular LDH activity in A2 type cells; recall that zero toxic response was detected in randomly cycling cells even under large concentrations, so effects due to toxicity are not expected in normal cells. It appears that exposure to compositions of the invention may tend to accelerate the removal of non-responsive confluent cells. This is evidently true when Cachexin is present. These results might also bear on the observations that exposure to compositions of the invention seemed to diminish cell proliferation in high concentrations. No such trend was tried for low-concentration exposure. Note that it is difficult to discount the possibility that high-concentration effects might simply be artifacts due to the interference of compositions of the invention with the growth medium.

Experimental methods to determine effects of 5-10% composition of the invention exposure to cells stressed by radiation and serum starvation: Murine (JB6) cell cultures were subjected to high-level radiation exposure (X-rays) and, in a separate investigation, cultures were subject to serum starvation of growth factors for 24 hours. The cells were then exposed to 5-10% ASEA exposure as means to determine the effect of composition of the invention exposure on such stressed cells. Cell counts were taken before and after composition of the invention exposure.

Results of effects of 5-10% composition of the invention exposure on radiation and serum-starved murine cells: Quantitative analysis was not compiled for these experiments. Qualitative analysis, however, reveals results that might be of some interest. For the radiation-damaged culture, immediate cell death was observed for more than half of the culture upon exposure to composition of the invention. No further cell-death was seen thereafter. Upon inspection under a microscope, the remaining living cells appeared normal and healthy. It appears that exposure to a composition of the invention may have helped accelerate cell death among the more seriously damaged cells and allowed for the survival of healthy or repairable cells.

For serum-starved cell cultures similar observations were made, except the cell death was not nearly as severe, amounting to less than roughly a 20% loss. Surviving cells appeared to be very robust and viable. Similar losses, however, were also seen in serum-starved cultures that were not exposed to compositions of the invention in later experiments.

A better understanding of the bioactivity of a certain mixture of redox signaling molecules has been determined from in vitro studies involving direct contact of compositions of the invention with viable living HMVEC-L human cells and murine epidermal JB6 cells. Five specific objectives were pursued to determine:

1) In vitro toxicity (based on NF-kB, P-Jun translocation)
2) Effects on antioxidant efficacy (for GPx and SOD)
3) Effects on antioxidant transcriptional activity (NRF2)
4) Effects on cell proliferation and viability (cell counts)
5) Effects on stressed cells (Cachexin, radiation, starvation)

No toxic response was observed for any healthy cell culture in normal random phases (HMVEC-L or JB6) upon exposure to high concentration compositions of the invention (up to 20%) of serum. Two methods were used to determine toxic response, the translocation and accumulation of NF-kB and P-Jun in the nuclei. Both of these methods are known to be sensitive to low-levels of toxicity, as verified by the positive control. A complete lack of toxic indication and/or inflammatory cytokines was observed.

An 800% increase in GPx antioxidant efficacy in HMVEC-L cells was seen after 24 hours exposure from low-concentration composition of the invention (no concentration dependence seen). A transitory increase of up to 500% was seen in SOD antioxidant efficacy between 30 to 90 min. again after exposure to a low-concentration of a composition of the invention (<1%). In both cases, the low concentrations of compositions of the invention were comparable to blood concentrations possible from oral dosing, though data is not available to confirm this. Concentration dependence at very low concentrations might be seen if such was carefully investigated.

Exposure to high-concentration compositions of the invention, in comparison, elicited only a small relative increase in GPx antioxidant efficacy that was not concentration dependent. An increase in SOD efficacy was not seen for either high-concentration compositions of the invention or after long (24 hr) exposures. In subsequent investigations, this information will be used to determine optimal concentrations and time points to study concentration dependence (<0.1% and 0-120 minutes).

Studies examining the nuclear translocation of redox responsive transcription factors suggest that compositions of the invention at a lower concentration (less than 1%) induces a 20-30% increase in the nuclear translocation of the NRF2 transcription factor in HMVEC-L cells that appears to be transient (30-60 min). We also observed that a composition of the invention induced a parallel decrease in the phosphorylation of an extra-nuclear protein whose phosphorylation status is clearly increased in response to hydrogen peroxide treatment, consistent with an antioxidant mode of action.

Serum-starving HMVEC-L cells, as an approach to increase sensitivity, significantly increased the nuclear NRF2 signal induced by composition of the invention (1%). However, serum-starvation induced significant cell death complicating interpretation of the data.

Cellular proliferation for both HMVEC-L and JB6 cell types (determined from cell counts) was inhibited by high concentrations (5-20% v/v) of exposure to compositions of the invention. The HMVEC-L inhibition was clearly concentration dependent, with a 20% loss of cell count at 20% ASEA concentration. In contrast to decreased proliferation, serum LDH levels significantly decreased with compositions of the invention concentration between 5-20%, indicating increased cell membrane integrity. The results seem to indicate that cellular proliferation is decreased while cell membrane viability is increased at high concentrations. The mechanism behind such behavior cannot be deduced from the data, yet further evidence will be seen in the next section.

The response of HMVEC-L cells when stressed with Cachexin depends upon cell phase. Normal randomly cycling HMVEC-L cells (pS) exhibited typical behavior when stressed with Cachexin: exhibiting decrease in cell viability accompanied by cell death. Confluent end-of-life-cycle (A2) and borderline HMVEC-L cells, as expected, were less sensitive to Cachexin insult, exhibiting less pronounced decreases in cell viability and less cell death.

Exposure to compositions of the invention caused no significant change in the response of the normal random cycling pS cells to Cachexin (showing similar loss of cell viability and cell-death). However, A2 cell cultures exposed to a composition of the invention exhibited increased sensitivity to Cachexin, restoring behavior similar to that of normal cells. This behavior was reinforced as concentration dependence was examined. Borderline A2 cells, exhibiting a relatively small Cachexin response, and A2 cells that are normally insensitive to Cachexin insult, exhibited a much stronger response to Cachexin when exposed to compositions of the invention, both in decrease in viability and increased cell death.

It appears that exposure to compositions of the invention causes increased rates of A2 cell death, enhancing the natural reception of Cachexin in such end-of-life-cycle cells. Yet exposure to composition of the invention is not expected to cause any change in normal cell viability.

Cachexin is normally secreted to instigate cell death in damaged or dysfunctional tissues, allowing surrounding healthy cells to divide and fill in voids. Thus, increasing the sensitivity to Cachexin in dysfunctional cells may help accelerate such a process and is not always deleterious.

Acceleration of cell death was also seen in tissues that were stressed with radiation and serum-starvation associated with exposure to compositions of the invention.

The infusion of a certain balanced mixture of redox signaling molecules using compositions of the invention into viable HMVEC-L and JB6 cell cultures has been seen to elicit distinct bioactivity. No indications of toxicity or the expression of inflammatory cytokines were observed and yet there was increased antioxidant and protective enzyme expression (as evidenced by increased nuclear NRF2) and greatly increased efficacy for the two master antioxidants, GPx and SOD. This behavior suggests that infusion with compositions of the invention might tend to induce and enhance oxidative defense mechanisms without inducing toxic or inflammatory responses in such cells. Such action is unprecedented or extremely rare. Normally, low-level toxicity induces slight oxidative stress and inflammatory response which in turn induces oxidative defense and cell repair mechanisms. It would be of interest to determine concentration dependency of this effect with ultra-low-concentration infusions of compositions of the invention.

The induction of cell death in cultures of dysfunctional, stressed or damaged cells by infusion of compositions of the invention should also be explored. Natural healing processes involve a repair or replace mechanism by which marginally damaged cells are repaired, when possible, or undergo apoptosis, programmed death, if they cannot be repaired and then are replaced through mitosis of healthy neighboring cells. It is fairly evident that infusion of composition of the invention, of itself, is not causing direct stress to exposed cells, however, it might tend to increase the efficiency of certain cytokine "death domain" messengers (Cachexin) that are designed to induce cell death in dysfunctional or damaged cells. The nuclear translocation of NRF2 can be considered part of the phase II oxidative defense response which includes expression of antioxidants, DNA repair molecules and other known repair mechanisms.

Apoptosis is part of the replace mechanism when cells have undergone unrepairable damage and must be removed and replaced. Both antioxidant defense and apoptotic mechanisms are central to normal tissue repair and regeneration. Redox signaling is involved in several of the pathways, such as p53 gene expression, that can determine whether a cell undergoes apoptosis or not. Chronic oxidative stress tends to favor cell death. Certainly the presence of Cachexin and other death domain messengers favor cell death. The observation that infusion with compositions of the invention enhances Cachexin reception might indicate that infusion with compositions of the invention also might serve to enhance reception of messengers in the signaling process that determines whether defense, repair or replace mechanisms are activated.

Example 7

Determination of ROS Levels Against a Known Standard

The measurement of concentrations of ROS, particularly a superoxide, inside the solutions has been done by means of a fluoro spectrometer, Nanodrop 3300, and three varieties of fluorescent dyes, R-Phycoerytherin (R-PE), Hydroxyphenyl fluorescein (HPF) and Aminophenyl fluorescein (APF), that are commonly used to determine relative ROS concentrations inside active biological systems and cells. The molecules in these dyes change shape, and therefore fluoresce only when exposed to molecular components in ROS. The resulting change in fluorescence can then be detected by the fluoro spectrometer and can be related to the concentration of ROS present. ROS concentrations in electrolyzed saline solutions (ESS) solutions are verified and detected by either APF or R-PE fluorescent dyes, both of which produce entirely consistent measurements of relative concentrations of ROS in various concentrations and dilutions of ESS solutions. ROS measurements in ESS solutions have been linked using R-PE fluorescent dye, to the reaction of this dye to regulated concentrations of 2/2'-Axobis(2-methylpropionamide)dihidrochloride, a molecule that produces known amounts of ROS. This is not an absolute measurement, but it relates ROS in ESS to amounts of a known producer of ROS.

These fluorescent dyes are often used in combination with a fluorescence microscope to create high-resolution images of the build-up of ROS (oxidative stress) inside individual living cells. These dyes have been shown to specifically be sensitive to concentrations of ROS regardless of complex surrounding chemical environments.

Although APF and R-PE dyes are capable of measuring relative ROS concentrations in ESS solutions, no known absolute standard concentration for stabilized ROS in pure saline solutions exists. Furthermore, discrepancies in the decay time of these fluorescent dyes make measuring standardized amounts of ROS in other solutions incompatible with measuring those found in ESS. This may be due, in part, to the molecular complexes in ESS solutions that keep the ROS concentration stable, effectively shielding the free radicals from readily reacting with the dyes. The standard for ROS concentration in ESS solutions is therefore measured relative to the ROS concentration in a standardized solution that has been used in all of the antimicrobial and toxicity studies to date, both published and unpublished. Methods to measure absolute ROS concentrations in ESS solutions are actively being pursued.

The regulated amounts of ROS, thus measured, inside a variety of the ESS solutions produced by various embodiments of this invention have been shown to be stable, consistent and predictable, sufficient for therapeutic applications.

The development of a phycobiliprotein fluorescence quenching assay for the routine determination of ROS content in ASEA has been successful and is used routinely to monitor production quality for ROS levels. The assay has the following characteristics: ease of use, sensitivity, and quantitation. The assay is linear over a 2 log 10 range of ROS concentrations. For a compositions comprising RXNs, the starting saline was used as a negative control, AAPH (2,2'-Azobis(2-amidinopropane)dihydrochloride which is a standard ROS generating compound) served as a positive control and allowed the generation of a standard curve, and the compositions comprising RXNs or other samples comprised the unknowns.

Figure 23:
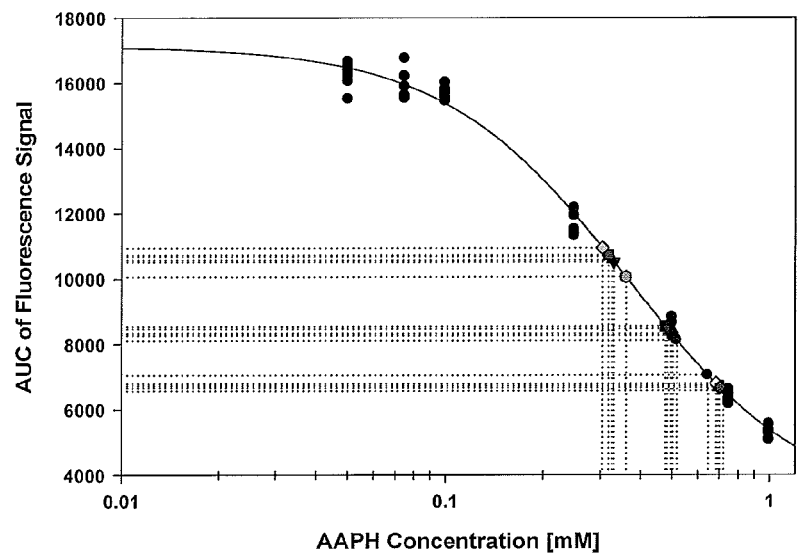
FIG. 23 is a graph of the Expt. 5f07 ROS Assay.

For the purposes of this work, we determined the oxygen radical content of our health benefiting product. In the assay described below, R-Phycoerythrin [an algal protein] is exposed to varying levels of a standard ROS generating compound [AAPH] wherein the level of fluorescence quenching is logarithmically related to ROS content. This provides a standard curve from which to estimate the ROS content of unknown samples. The levels of ROS in the unknown samples are expressed as mM equivalents of AAPH. FIG. 23 shows the concentration of AAPH.

Materials and Methods:

PHYCOERYTHRIN and R-PHYCOERYTHRIN: were purchased from Sigma Chemical Corporation, St. Louis, Mo.

AAPH: 2,2'-azobis(2-amidino-propane)dihydrochloride was purchased from Wako Chemicals USA, Richmond, Va. This compound generates ROS upon contact with water.

FLUORESCENCE READER: an 8 or 16 place fluorescence reader manufactured by Pacific Technologies, Redmond, Wash. was used to detect the fluorescence signal from the phycoerythrins. Temperature was controlled at 37 C during a 12-20 hr. experimental run. The samples were interrogated every 0.5 to 2 min where each sample interrogation was comprised of 1024 lamp flashes from a LED whose emission spectra was appropriate from the excitation spectra of R-Phycoerythrin. Proper cut-off filters were employed to detect the fluorescence emissions of the phycoerythrins.

DATA ANALYSES: All data is captured in real time. The data contained in the worksheet can be manipulated to determine the relative change of fluorescence over the time course of the experiment and subsequently, SigmaPlot Pro v. 7 software [SPSS Software, Chicago, Ill.] is used to determine the area under the curve. Area under the curve [AUC] analysis is appropriate since Cao, Cao et al. Comparison of different analytical methods for assessing total antioxidant capacity of human serum. Clinical Chemistry June 1998 vol. 44 no. 6 1309-1315 which is hereby incorporated by reference in its entirety, and colleagues have demonstrated that in this method both the inhibition time and degree of inhibition of fluorescence by free radicals are considered. The area under the curve [AUC] are plotted against the log 10 mM AAPH concentration to provide a standard curve from which to estimate the levels of ROS in unknown samples.

Detailed Methods

Step a. 300 uL of phosphate buffer, pH 7.0, 100 mM is added to ½" glass vials.

Step b. 15 ug of R-Phycoerythrin in 15 uL of phosphate buffer is added to the materials in Step a. The vials are capped and placed into the wells of the fluorescence reader for 15 min prior to the addition of a saline control, ASEA or AAPH solutions. During this period, fluorescence values are collected from which to calculate a 100% value. This value is then used in subsequent calculations to determine a relative fluorescence signal value for the standard curves.

1 mg of AAPH is added to 1 ml of phosphate buffer and 10-fold dilutions are made to provide at least a 3 log 10 range of AAPH concentrations. Similarly, ASEA solutions are diluted and added to appropriate vials in Step b.

100 uL of the materials in Step a are added to the appropriate vials in Step b. The vials are mixed and replaced into the reader for up to an additional 12 to 20 hrs of evaluation.

RESULTS: As shown in FIG. 23, as the concentration of AAPH decreased from 1.00 mM to 0.050 mM, there was as concomitant increase in the normalized AUC. Buffer control [not shown] revealed that over time there is a spontaneous loss of fluorescence signal, although this loss represents only ~8% of the original signal.

Figure 24:
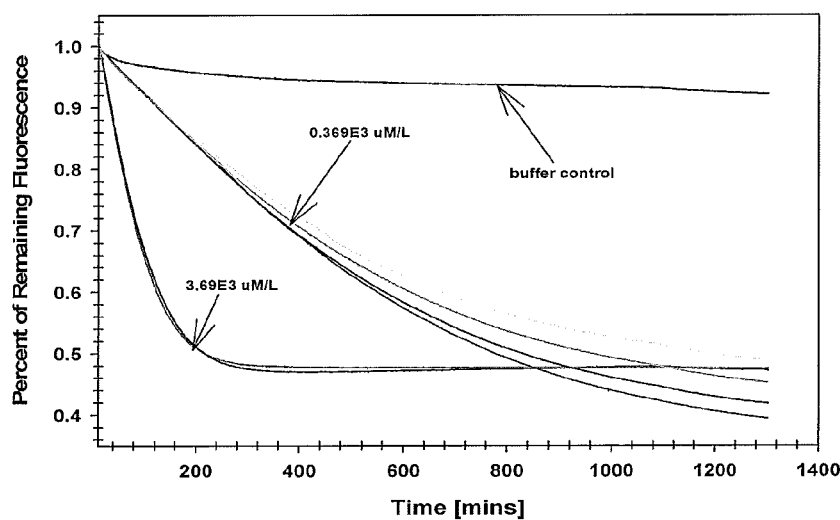
FIG. 24 is a graph of an Intraassay Variation Using Two Levels of AAPH.

The data represented in FIG. 24 shows intra-assay variability of two concentrations of AAPH. Using SigmaStat v 2.01 software, the following mean, Std Deviation and Relative Std Deviation were calculated and are presented in Table 1. The data shows that the variation for each concentration the variation among replicates ranged from ~0.1% to 4% variation [Rel. Std. Dev.]. These data suggest that fluorescence quenching assay is capable of producing small variations among triplicate or quadruplicate samples over a 10-fold range of AAPH concentrations.

TABLE 1

Intraassay Variability

| AAPH Concentration | N | Mean AUC | Std. Dev. | Std. Error | % Rel. Std. Dev. |
|---|---|---|---|---|---|
| | | AUC Values | | | |
| 3.69 mM | 3 | 653 | 1.07 | 0.62 | 0.15 |
| 0.369 mM | 4 | 804 | 31.7 | 15.0 | 3.7 |

Table 2 shows the results of the analyses of ASEA solutions prepared by MDI and filtered through 0.2 u Supor membrane to ensure sterility prior to clinical application. It is clear that the ASEA from different production lots are similar in their ROS content. Statistical analysis supported this observation [p=0.272]. The most important point is the observation that filtration through a 0.2 u Supor membrane does not decrease the ROS content of ASEA.

Table 2. ROS Content of ASEA Filtered and Unfiltered Through 0.2 Supor Membrane

TABLE 2

| Treatment | N | Mean AUC | Std. Dev. | Std. Error | % Rel. Std. Dev. |
|---|---|---|---|---|---|
| Unfiltered | 4 | 589.7 | 65.8 | 32.9 | 5.5 |
| Filtered | 4 | 646.3 | 66.3 | 33.1 | 5.1 |

The levels of variance [Rel. Std. Dev.] reported by us is similar to that reported by Cao and colleagues[i].

In Table 3, data from a typical analysis is illustrated. Saline [negative control] always contained less than 0.1 mM AAPH equivalents of ROS whereas ASEA always contained >1.0 mM ROS.

TABLE 3

ROS Content of ASEA and Saline

| ASEA or Saline Samples | Mean AUC | ROS Content mM AAPH equivalents |
|---|---|---|
| ASEA | 479 | 3.3 |
| ASEA | 543 | 2.2 |
| ASEA | 441 | 4.5 |
| ASEA | 523 | 2.98 |

TABLE 3-continued

ROS Content of ASEA and Saline

| ASEA or Saline Samples | Mean AUC | ROS Content mM AAPH equivalents |
|---|---|---|
| ASEA | 516 | 3.2 |
| Saline | 974 | 0.095 |
| Saline | 956 | 0.075 |

The above shows a known concentration of a standard, AAPH, as 653 and 804 when tested at 3.69 mM and 0.369 mM respectively. A compositions comprising RXNs showed a AUC of between 441-543

The measurement of concentrations of ROS inside the solutions can be done by means of a fluorospectrometer, Nanodrop 3300, and three varieties of fluorescent dyes, R-Phycoerytherin (R-PE), Hydroxyphenyl fluorescein (HPF) and Aminophenyl fluorescein (APF), all of which are commonly used to determine relative ROS concentrations inside active biological systems and cells. The molecules in these dyes change shape, and therefore fluoresce only when exposed to molecular components in ROS. The resulting change in fluorescence can then be detected by the fluorospectrometer and can be related to the concentration of ROS present. ROS concentrations in a compositions comprising RXNs can be verified and detected by either APF or R-PE fluorescent dyes, both of which produce entirely consistent measurements of relative concentrations of ROS in various concentrations and dilutions of RXNs. The ROS measurements in a compositions comprising RXNs have been linked, using R-PE fluorescent dye, to the reaction of this dye to regulated concentrations of 2/2'-Axobis(2-methylpropionamide)dihidrochloride, a molecule that produces known amounts of ROS.

Superoxide Testing

Superoxides were tested with the NanoDrop 3300 and R-PE as the reagent for the tree samples.

The intensity of the fluorescence indicates the amount of ROS in the sample. This dye, R-PE, is toxic, expensive, must be kept refrigerated, degrades in strong blue light, such as a fluorescent bulb, and is time sensitive. The following steps were taken:

The ND-3300 software was called up, the "Other Fluorophores" button was clicked and the "R-PE 50 uM Activated" option was selected.

The ND-3300 was blanked: 2 uL (1 drop) of deionized water was placed using a pipette on the measurement pedestal and the arm was carefully closed. The "Blank" button was clicked and the ND-3300 took a "blank" measurement, thereby calibrating the ND-3300.

The samples were prepared by pipetting 10 ml deionized water into each one of the large (15 ml) test tubes required for the test. One test tube will be required for each sample to be tested.

The test tubes were labeled by cutting out squares of sticky-back label stock, large enough to fit over the mouth of the test tubes, and by writing the number "1", "2" and "3" on the label. The labels were placed covering the mouth of the test tubes to both identify them and to keep the liquids from evaporating.

10 ul of the R-PE fluorescent dye was apportioned into each one of the test tubes by following these steps: turning off the lights, taking the previously prepared R-PE dye test tube out of the refrigerator [this test tube was previously prepared by putting 2 ul of the concentrate from the commercial R-PE vial inside 5 ml deionized water (a phosphate buffer is not needed)]. The prepared test tube was placed in the rack with the others. This dye is toxic and is sensitive to light so these steps should be done quickly, with lab coat, gloves and goggles. With a clean pipette, 10 ul of the prepared R-PE dye was add into each of the test tubes. The R-PE was placed back in the test tube back in the refrigerator.

The test tubes were mixed well using a mixing pipette which was place into each of the test tubes, 2-3 ml were drawn out and then quickly pushed back in, allowing some bubbles to escape to better agitate the contents of the test tubes. This was repeated three to four times for each tube. At this point, it is necessary to have separate mixing pipette heads for each tube. The test tubes were allowed to sit for least 30 min. after mixing.

The initial pre-sample measurements were taken on all of the test tubes: The ND-3300 was blanked using the procedures outlined above. A folded Kimwipe was used to blot the last sample droplet off the lower and upper pedestals before loading a new drop to be analyzed. A descriptive name for the sample was typed into the Sample ID field in the software. 2 ul of test tube #1 was loaded onto the pedestal, the arm was carefully closed and the "measure" button pressed. Three measurements were taken of the sample in test tube #1. This procedure was repeated for the next two samples. Specifically, the Sample ID field was changed to reflect the descriptive name of the sample in the second test tube. And then three (3) measurements were taken from the second test tube also. This step was done until all test tubes were analyzed. When R-PE was activated, the RFU readings shown were between the 100 and 2000.

A compositions comprising RXNs was added to the test tubes: This procedure was carefully timed. The R-PE dye is only accurate for less than 30 minutes after activation and therefore all measurements must be acquired after the same amount of exposure time. 10 ul of a compositions comprising RXNs sample #1 was added to test tube #1 and immediately thereafter a timer was set for three (3) minutes. Then the test tube #1 was mixed with a pipette. This step was repeated for all three samples.

At 6 hrs post addition of the first a compositions comprising RXNs sample to a test tube, measurements were taken from every test tube in the following manner. The ND-3300 was blanked, the pedestals were blotted and the "Sample ID" for test tube #1 was typed in. After three (3) minutes, using a sampling pipette, a 2 ul drop was taken from test tube #1 and place it on the pedestal and the measure button was pressed. This process was repeated until all of the test tubes were measured.

The data was cleaned up by pressing the "Show Report" button so that all of the data that has been taken so far was displayed. The data was then saved and analyzed.

Hypochlorite Testing

Hypochlorites were tested with the NanoDrop 3300 Fluorospectrometer and APF as the reagent.

The ND-3300 software was called up, the "Other Fluorophores" button was clicked and the "APF 50 uM Activated" option was selected.

The ND-3300 was blanked: 2 uL (1 drop) of deionized water was placed using a pipette on the measurement pedestal and the arm was carefully closed. The "Blank" button was clicked and the ND-3300 took a "blank" measurement, thereby calibrating the ND-3300.

The samples were prepared by pipetting 10 ml deionized water into each one of the large (15 ml) test tubes required for the test. One test tube will be required for each sample to be tested.

The test tubes were labeled by cutting out squares of sticky-back label stock, large enough to fit over the mouth of the test tubes, and by writing the number "1", "2" and "3" on the label. The labels were placed covering the mouth of the test tubes to both identify them and to keep the liquids from evaporating.

10 ul of the APF fluorescent dye was apportioned into each of the test tubes by following these steps: turning off the lights, taking the previously prepared APF dye test tube out of the refrigerator [this test tube was previously prepared by putting 2 ul of the concentrate from the commercial APF vial inside 5 ml deionized water (a phosphate buffer is not needed)]. The prepared test tube was placed in the rack with the others. This dye is toxic and is sensitive to light so these steps should be done quickly, with lab coat, gloves and goggles. With a clean pipette, 10 ul of the prepared APF dye was add into each of the test tubes. The APF was placed back in the test tube back in the refrigerator.

The test tubes were mixed well using a mixing pipette which was place into each of the test tubes, 2-3 ml were drawn out and then quickly pushed back in, allowing some bubbles to escape to better agitate the contents of the test tubes. This was repeated three to four times for each tube. At this point, it is necessary to have separate mixing pipette heads for each tube. The test tubes were allowed to sit for least 30 min. after mixing.

The initial pre-sample measurements were taken on all of the test tubes: The ND-3300 was blanked using the procedures outlined above. A folded Kimwipe was used to blot the last sample droplet off the lower and upper pedestals before loading a new drop to be analyzed. A descriptive name for the sample was typed into the Sample ID field in the software. 2 ul of test tube #1 was loaded onto the pedestal, the arm was carefully closed and the "measure" button pressed. Three measurements were taken of the sample in test tube #1. This procedure was repeated for the next two samples. Specifically, the Sample ID field was changed to reflect the descriptive name of the sample in the second test tube. And then three (3) measurements were taken from the second test tube also. This step was done until all test tubes were analyzed. When APF was activated, the RFU readings shown were between the 100 and 2000.

A compositions comprising RXNs was added to the test tubes: This procedure was carefully timed. The APF dye is only accurate for less than 30 minutes after activation and therefore all measurements must be acquired after the same amount of exposure time. 10 ul of a compositions comprising RXNs sample #1 was added to test tube #1 and immediately thereafter a timer was set for three (3) minutes. Then the test tube #1 was mixed with a pipette. This step was repeated for all three samples.

At 30 min. post addition of the first a compositions comprising RXNs sample to a test tube, measurements were taken from every test tube in the following manner. The ND-3300 was blanked, the pedestals were blotted and the "Sample ID" for test tube #1 was typed in. After three (3) minutes, using a sampling pipette, a 2 ul drop was taken from test tube #1 and place it on the pedestal and the measure button was pressed. This process was repeated until all of the test tubes were measured.

Packaging

The packaging process includes any type of packaging that does not contribute to the decay of the superoxides, hydroxyl radicals and OOH* (for example, containers should not contain metal oxides or ions). Pouches and bottles are preferred for ease of portability and acceptability in the market. However, any suitable packaging is applicable. Containers/packaging can be made of for example glass, polyethylene, polypropylene and the like. Table 4 shows the relative percentage of superoxides remaining after a 12 month period when the composition is packaged in a polyethylene bottle.

TABLE 4

1 Year Studies - shows a 3%/month decay rate over a 12 month period from a product made according to Example 1

| Sample ID | RFU | RFU Average per sample | RFU minus control | Standard deviation | % error | % Potency as compared to reference sample |
|---|---|---|---|---|---|---|
| RFU Control | 1743.7 | 1759.033 | | | | |
| Control | 1814.6 | | | | | |
| Control | 1718.8 | | | | | |
| Sample 1 | 985.6 | 986.1667 | 872.8667 | 6.169549 | 0.706815 | 1 |
| Sample 1 | 980.3 | | | | | |
| Sample 1 | 992.6 | | | | | |
| Sample 2 | 1044.8 | 1003.6 | 855.4333 | 35.68151 | 4.171162 | Baseline |
| Sample 2 | 982.7 | | | | | |
| Sample 2 | 983.3 | | | | | |
| Sample 3 | 981.7 | 988.3 | 870.7333 | 16.23915 | 1.864997 | 1.007618 |
| Sample 3 | 1006.8 | | | | | |
| Sample 3 | 976.4 | | | | | |
| Sample 4 | 1132.9 | 1121.133 | 737.9 | 12.56437 | 1.70272 | 0.853903 |
| Sample 4 | 1107.9 | | | | | |
| Sample 4 | 1122.6 | | | | | |
| Sample 5 | 1189.9 | 1182.2 | 676.8333 | 19.99475 | 2.954161 | 0.783236 |
| Sample 5 | 1197.2 | | | | | |
| Sample 5 | 1159.5 | | | | | |
| Sample 6 | 1269.3 | 1256.267 | 602.7667 | 26.47647 | 4.39249 | 0.697526 |
| Sample 6 | 1225.8 | | | | | |
| Sample 6 | 1273.7 | | | | | |

Table 4 provides data for the RFU control, Sample 1 which is a reference sample and Samples 2-6 which were taken at 1 month, 3 months, 6 months and 12 months. Table 4A shows the results as a percentage of remaining superoxides at 0, 1, 3, 6 and 12 months.

TABLE 4A

| Month | % Potency |
|---|---|
| 0 | 100 |
| 1 | 101 |
| 3 | 85 |
| 6 | 78 |
| 12 | 70 |

Table 5 shows the relative percentage of superoxides remaining after a 13 month period when the composition is packaged in a polyethylene bottle and polyethylene pouch.

TABLE 5

13 Month Pouch v. Bottle from products made according to Example 1

| Sample ID | RFU | RFU Average per sample | Standard deviation | % error | RFU minus control | % Potency as compared to reference sample |
|---|---|---|---|---|---|---|
| Control | 1687.9 | | | | | |
| 555 | 946.4 | 940.7667 | 9.157693 | 0.973429 | 1325.273 | 1 |
| 555 | 930.2 | | | | 1370.007 | |
| 555 | 945.7 | | | | | |
| 555-1 | 817.5 | 851.3 | 29.27781 | 3.439188 | 1414.74 | 1.067508 |
| 555-1 | 867.6 | | | | | |
| 555-1 | 868.8 | | | | | |
| 525b | 967.2 | 966.0333 | 10.3992 | 1.076484 | 1300.007 | 0.948905 |
| 525b | 955.1 | | | | | |
| 525b | 975.8 | | | | | |
| 524p | 983.1 | 975.7333 | 17.08576 | 1.751069 | 1290.307 | 0.941825 |
| 524p | 956.2 | | | | | |
| 524p | 987.9 | | | | | |
| 480 | 985.9 | 1006.333 | 19.12337 | 1.900302 | 1259.707 | 0.919489 |
| 480 | 1009.3 | | | | | |
| 480 | 1023.8 | | | | | |
| 479p | 1115.2 | 1153.5 | 45.22975 | 3.921088 | 1112.54 | 0.812069 |
| 479p | 1141.9 | | | | | |
| 479p | 1203.4 | | | | | |

TABLE 5-continued

13 Month Pouch v. Bottle from products made according to Example 1

| Sample ID | RFU | RFU Average per sample | Standard deviation | % error | RFU minus control | % Potency as compared to reference sample |
|---|---|---|---|---|---|---|
| 408p | 1454.2 | 1501.633 | 62.98812 | 4.194641 | 764.4067 | 0.557958 |
| 408p | 1573.1 | | | | | |
| 408p | 1477.6 | | | | | |
| 347p | 1309.4 | 1327.833 | 39.24364 | 2.955464 | 938.2067 | 0.684819 |
| 347p | 1301.2 | | | | | |
| 347p | 1372.9 | | | | | |
| 347p | 1338.1 | | | | | |
| 314 | 1354.4 | 1348.567 | 16.82627 | 1.247715 | 917.4733 | 0.669685 |
| 314 | 1361.7 | | | | | |
| 314 | 1329.6 | | | | | |
| 313p | 1459.3 | 1444.033 | 13.25908 | 0.918198 | 822.0067 | 0.600002 |
| 313p | 1435.4 | | | | | |
| 313p | 1437.4 | | | | | |

The above graph shows a 4.4% decay rate of the superoxide radical for the pouch and a 3% decay rate for the bottle over a 13 month period. Sample 555 is a reference sample, Sample 555-1 is a baseline sample, Sample 525b is a sample taken from a bottle after 1 month, Sample 524p is a sample taken from a pouch after 1 month, Sample 480 is a Sample taken from a bottle after 3 months, Sample 479p is a sample taken from a pouch after 3 months, Sample 408p is a sample taken from a pouch after 8 months, Sample 374p is a sample taken from a pouch after 11 months, Sample 314 is a sample taken from a bottle after 13 months and Sample 313p is a sample taken from a pouch after 13 months. Table 5A is a chart showing the percentage of remaining superoxides at 0, 1, 3, 8, 11 and 13 months in a bottle and a pouch type container.

TABLE 5A

| Month | % Potency | % Potency |
|---|---|---|
| 0 | 100 | 100 |
| 1 | 95 | 94 |
| 3 | 92 | 81 |
| 8 | | 56 |
| 11 | | 68 |
| 13 | 67 | 60 |

Borosilicate Glass

Borosilicate glass, such as those sold under the trade names of Kimax, Pyrex, Endural, Schott, or Refinex for example, are useful for packaging of a compositions comprising RXNs.

The presence of superoxides in a compositions comprising RXNs samples were tested after being stored in borosilicate glass bottles. Sample 397 had been stored for 24 months and Sample 512 had been stored for 20 months. Reference batch 1256 was made the same day as the test was run on all three samples. The Results are shown in Table 6.

TABLE 6 from a product made according to Example 1
Glass Bottle ASEA
Stability

| Sample | RFU | average RFU | Control - average + control loss | |
|---|---|---|---|---|
| 397 | 780.5 | 806.8 | 1193.2 | 93.1169 |
| | 819.5 | | | |
| | 820.4 | | | |
| 512 | 676.7 | 682.4666667 | 1317.533333 | 102.8198 |
| | 682.6 | | | |
| | 688.1 | | | |
| Ref batch 1256 | 754.8 | 718.6 | 1281.4 | 100 |
| | 707.2 | | | |
| | 693.8 | | | |
| Control | 1850 | | | |
| Control after 6 hours | 1700 | | | |
| Control loss due to warmth | 150 | | | |

It can be seen from the Tables that the relative concentrations of superoxides do not appreciably degrade while in the borosilicate bottles. Sample 397 had a decayed about 5% and sample 512 had 0% decay. Therefore, the yearly decay of product is no more than about 2.5% decay per year. This gives an estimated half-life of the superoxides at about 24 years.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of reducing or ameliorating cellular oxidative stress comprising:
    determining a balanced target mixture of reduced species (RS) and reactive oxygen species (ROS) found in a biological system;
    electrochemically replicating the balanced target mixture of reduced species (RS) and reactive oxygen species (ROS) by a method comprising:
        circulating a saline solution within an electrolysis cell comprising an anode and a cathode in which there are no barriers between the electrodes while adjusting temperature, circulation, and salinity of the circulating saline solution at a level to reduce production of chlorates and to regulate relative concentrations of resulting reactive molecules;
        electrolyzing the circulating saline solution to oxidize and reduce the circulating saline solution to produce a concentration and mixture of reduced species (RS) and reactive oxygen species (ROS) that mirrors those present in the target mixture by varying temperature, circulation, power-source modulation, and salinity of the circulating saline solution to form a composition;
    contacting at least one cell of the biological system with the composition; and
    measuring an increase in antioxidant activity in the at least one cell of the biological system.

2. The method of claim 1, wherein the reactive oxygen species (ROS) comprises at least one superoxide.

3. The method of claim 2, wherein the superoxide is $*O_2^-$.

4. The method of claim 1, wherein the composition comprises at least one hypochlorite.

5. The method of claim 1, wherein the composition includes HOCl, NaClO, $O_2$, $H_2$, $H^+$, ClO, $Cl_2$, $H_2O_2$, $O_2^-$, $HO_2$, $Cl^-$, $H^-$, $*OCl$, $O_3$, $*O_2^-$ and $OH^-$.

6. The method of claim 1, further comprising verifying the concentration and presence of reactive oxygen species (ROS) in the composition by using three indicators, R-phycoerythrin (R-PE), aminophenyl fluorescein (APF), and hydroxphenyl fluorescein (HPF) such that:
    1) a 2 µM concentration of R-PE loses 5% to 50% of its fluorescence 6 hours after a 1:1000 dilution of the composition is added;
    2) R-PE measurements indicate the same fluorescence levels as a standard ROS generating solution of 0.2 to 1.0 mM 2,2'-azobis(2-amidino-propane) dihydrochloride (AAPH);
    3) APF measurements indicate the same relative amount as the balanced target mixture; and
    4) HPF measurements indicate a negligibly small reading.

7. The method of claim 1, wherein the composition comprises a pH of between 6.8 and 8.2.

8. The method of claim 1, wherein the composition comprises a total chlorine concentration of less than 35 ppm by weight.

9. The method of claim 1, wherein the temperature is between 4.5 and 5.8° C.

10. A method of reducing or ameliorating cellular oxidative stress comprising:
    preparing a composition by electrolyzing a circulating saline solution within an electrolysis cell comprising an anode and a cathode in which there are no barriers between the electrodes to oxidize and reduce the circulating saline solution to produce a concentration and mixture of reduced species (RS) and reactive oxygen species (ROS) that mirrors those present in a biological system;
    contacting cells in the biological system with the composition to increase antioxidant activity in the cells; and
    measuring an increase in antioxidant activity in the cells;
    wherein varying temperature, circulation, power-source modulation, and salinity of the circulating saline solution reduces production of chlorates and regulates relative concentrations of resulting reactive molecules.

11. The method of claim 10, wherein measuring an increase in antioxidant activity in the cells further comprises measuring an increase in expression of antioxidant enzymes in the cells.

12. The method of claim 11, wherein measuring an increase in antioxidant activity in the cells further comprises measuring translocation of NRF2 to the nuclei of the cells, wherein translocation of NRF2 indicates an increase in expression of antioxidant enzymes in the cells.

13. The method of claim 10, wherein measuring an increase in antioxidant activity in the cells further comprises measuring an increase in enzymatic activity of an antioxidant enzyme.

14. The method of claim 10, wherein measuring an increase in antioxidant activity in the cells further comprises measuring an increase in enzymatic activity of a glutathione peroxidase.

15. The method of claim 10, wherein measuring an increase in antioxidant activity in the cells further comprises measuring an increase in enzymatic activity of a superoxide dismutase.

16. A method of reducing or ameliorating cellular oxidative stress comprising:

determining a balanced target mixture of reduced species (RS) and reactive oxygen species (ROS) found in a biological system;

preparing a composition that mirrors the balanced target mixture of reduced species (RS) and reactive oxygen species (ROS) by electrolyzing a circulating saline solution within an electrolysis cell comprising an anode and a cathode in which there are no barriers between the electrodes to oxidize and reduce the circulating saline solution to produce a concentration and mixture of reduced species (RS) and reactive oxygen species (ROS) that mirrors those present in a biological system;

verifying that the composition does not elicit a toxic response by contacting a first aliquot of test cells with the composition and monitoring translocation of NF-κB to the nuclei of the first aliquot of test cells, wherein no translocation of NF-κB to the nuclei of the first aliquot of test cells indicates that the composition does not elicit a toxic response;

contacting cells of the biological system with the composition; and measuring an increase in antioxidant activity in the cells of the biological system.

17. The method of claim 16 further comprising verifying that the composition does not elicit an inflammatory response by contacting a second aliquot of test cells with the composition and monitoring accumulation of P-Jun to the nuclei of the second aliquot of test cells, wherein no accumulation of P-Jun to the nuclei of the second aliquot of test cells indicates that the composition does not elicit an inflammatory response.

* * * * *